United States Patent
Hirase et al.

(10) Patent No.: US 10,807,061 B2
(45) Date of Patent: Oct. 20, 2020

(54) LIPID MEMBRANE STRUCTURE, LIPID-MEMBRANE-STRUCTURE-IMMOBILIZATION CARRIER, AND METHOD OF FUSING VESICLES

(71) Applicant: TOPPAN PRINTING CO., LTD., Tokyo (JP)

(72) Inventors: Takumi Hirase, Tokyo (JP); Rii Morimura, Tokyo (JP); Masato Nakayama, Tokyo (JP)

(73) Assignee: TOPPAN PRINTING CO., LTD., Tokyo (JP)

(*) Notice: Subject to any disclaimer, the term of this patent is extended or adjusted under 35 U.S.C. 154(b) by 191 days.

(21) Appl. No.: 15/412,908

(22) Filed: Jan. 23, 2017

(65) Prior Publication Data

US 2017/0128904 A1    May 11, 2017

Related U.S. Application Data

(63) Continuation of application No. PCT/JP2015/071118, filed on Jul. 24, 2015.

(30) Foreign Application Priority Data

Jul. 24, 2014   (JP) ................. 2014-150868

(51) Int. Cl.

| | | |
|---|---|---|
| *B01J 13/20* | (2006.01) | |
| *G01N 33/92* | (2006.01) | |
| *B01J 13/00* | (2006.01) | |
| *C09K 11/06* | (2006.01) | |
| *G01N 21/64* | (2006.01) | |
| *G01N 33/58* | (2006.01) | |
| *G01N 21/78* | (2006.01) | |

(52) U.S. Cl.
CPC .............. *B01J 13/20* (2013.01); *B01J 13/00* (2013.01); *C09K 11/06* (2013.01); *G01N 21/6428* (2013.01); *G01N 33/582* (2013.01); *G01N 33/92* (2013.01); *C09K 2211/1088* (2013.01); *G01N 21/78* (2013.01); *G01N 2021/6439* (2013.01)

(58) Field of Classification Search
None
See application file for complete search history.

(56) References Cited

U.S. PATENT DOCUMENTS

| | | | |
|---|---|---|---|
| 5,591,448 A | 1/1997 | Slobodan | |
| 6,899,863 B1 | 5/2005 | Dhellin et al. | |
| 2007/0275480 A1* | 11/2007 | Brander ............ | B82Y 5/00 436/501 |
| 2012/0020878 A1 | 1/2012 | Qi | |
| 2013/0053426 A1 | 2/2013 | Seow et al. | |

FOREIGN PATENT DOCUMENTS

| | | |
|---|---|---|
| JP | 7-241192 | 9/1995 |
| JP | 2002-535665 | 10/2002 |
| JP | 2003-531864 | 10/2003 |
| JP | 2006-34211 | 2/2006 |
| JP | 2008-29952 | 2/2008 |
| JP | 2008-81486 | 4/2008 |
| JP | 2010-517048 | 5/2010 |
| JP | 2010-534480 | 11/2010 |
| JP | 2011-524164 | 9/2011 |
| JP | 2012-524052 | 10/2012 |
| JP | 2013-7698 | 1/2013 |
| JP | 2013-102768 | 5/2013 |
| JP | 2013-516619 | 5/2013 |
| WO | WO 01/82958 A2 | 11/2001 |
| WO | WO 2005/001070 A1 | 1/2005 |
| WO | WO 2008/092164 A2 | 7/2008 |
| WO | WO 2009/015357 A1 | 1/2009 |
| WO | WO 2009/147519 A1 | 12/2009 |
| WO | 2010/085259 A1 | 7/2010 |
| WO | WO 2010/119256 A1 | 10/2010 |
| WO | WO 2011/083145 A1 | 7/2011 |

OTHER PUBLICATIONS

Atsushi et al. (JP 2008/081486 A) (EPO machine translation) (Year: 2008).*
Höfer et al. "A membrane fusion assay based on pore-spanning lipid bilayers." Soft Matter 7.5 (2011): 1644-1647 (Year: 2011).*
International Search Report dated Oct. 27, 2015 in corresponding International Application No. PCT/JP2015/071118.
Office Action dated Jan. 16, 2018 in related Singaporean Patent Application No. 11201700557R, 8 pgs.
Nagatani, N. et al., "Development of a new transformation method using magnetite cationic liposomes and magnetic selection of transformed cells", Biotechnology Techniques, vol. 12, No. 7, Jul. 1998, pp. 525-528.
Kyoung, M. et al., "Studying calcium-triggered vesicle fusion in a single vesicle-vesicle content and lipid-mixing system", Nature Protocols vol. 8, No. 1, Dec. 2012, 16 pgs.
Tarahovsky et al., "Calcium-dependent aggregation and fusion of phosphatidylcholine liposomes induced by complexes of flavonoids with divalent iron," Biochimica et Biophysica Acta 1818 (2012), pp. 695-702.
Connor et al., "pH-sensitive liposomes: Acid-induced liposome fusion," Proceedings of the National Academy of Sciences of the United States of America, vol. 81, Mar. 1984, XP-002419985, pp. 1715-1718.

(Continued)

*Primary Examiner* — Emily A Cordas

(57) ABSTRACT

In methods of separating, moving, and detecting a vesicle of the present invention, either a vesicular-shaped lipid membrane structure containing a membrane-fusogenic lipid capable of being fused with a vesicle having a lipid bilayer membrane, or a lipid-membrane-structure-immobilization carrier, in which a lipid membrane structure containing a membrane-fusogenic lipid capable of being fused with a vesicle having a lipid bilayer membrane is immobilized on a carrier, is brought into contact with a sample containing the vesicle such that membrane fusion occurs between the lipid membrane structure and the vesicle.

7 Claims, 26 Drawing Sheets

(56) References Cited

OTHER PUBLICATIONS

Yang et al., "Effects of Lipid Headgroup and Packing Stress on Poly(Ethylene Glycol)-Induced Phospholipid Vesicle Aggregation and Fusion," Biophsyical Journal, vol. 73, Jul. 1997, pp. 277-282.
Partial Supplementary European Search Report dated Feb. 19, 2018 in corresponding European Patent Application No. 15825151.2, 17 pgs.
Akira Ito et al., "*Application to Regenerative Medicine using Nano Magnetic Fine Particles*"; The Society of Powder Technology, Japan, The Association of Powder Process Industry and Engineering, Japan, The 41$^{st}$ Technical Review Meeting and Text, Jul. 3, 2006, pp. 13-16 (13 pages).
Kamila Pszon-Bartosz et al., Biochemical and Biophysical Research Communications, "*Assessing the efficacy of vesicle fusion with planar membrane arrays using a mitochondrial porin as a reporter*"; 2011, vol. 406, pp. 96 to 100; (5 pages).
Office Action dated Jul. 2, 2019 in Japanese Patent Application No. 2016-535996 (7 pages) (6 pages English Translation).
C. Riviére, et al.; "Internal structure of magnetic endosomes"; The European Physical Journal E; Eur. Phys. J. E 22, 1-10 (2007); DOI: 10.1140/epje/e2007-00014-1; Mar. 3, 2007 (10 pages).
European Office Action dated Feb. 11, 2020 in European Patent Application No. 15825151.2 (8 pages).

* cited by examiner

LIPID MEMBRANE STRUCTURE, LIPID-MEMBRANE-STRUCTURE-IMMOBILIZATION CARRIER, AND METHOD OF FUSING VESICLES

CROSS REFERENCE TO RELATED APPLICATIONS

This application is a continuation application based on a PCT Patent Application No. PCT/JP2015/071118, filed Jul. 24, 2015, whose priority is claimed on Japanese Patent Application No. 2014-150868, filed Jul. 24, 2014, the content of which is hereby incorporated by reference.

BACKGROUND OF THE INVENTION

Field of the Invention

The present invention relates to a lipid membrane structure containing a membrane-fusogenic lipid to be fused (capable of being fused) with a vesicle having a lipid bilayer membrane, a lipid-membrane-structure-immobilization carrier in which the lipid membrane structure is immobilized, and a method of fusing vesicles using the lipid membrane structure and the lipid-membrane-structure-immobilization carrier. The present invention also relates to a method of separating a vesicle, a method of detecting a vesicle, and a method of moving a vesicle by using the fusion of vesicles.

Description of Related Art

Conventionally, regarding the structures covered with a lipid bilayer membrane, such as a membrane vesicle derived from a biological body such as a cell or an organelle and an artificial membrane vesicle, analyses on the contents of these structures, the substances held on the lipid bilayer membrane, and the like are conducted.

In recent years, as an intercellular communication method, a method mediated by an exosome, which is a vesicle having a lipid bilayer membrane, has drawn attention.

The exosome is a membrane vesicle which is known to contain a protein, mRNA, micro RNA (miRNA), DNA, and the like in the inside thereof and can transmit information to a cell at the destination by moving from cell to cell. For example, it is known that in a cell accepting a micro RNA-containing exosome derived from a cancer cell, immune function is activated, or metastatic potential is obtained.

The exosome contains genetic information that a cell releasing the exosome holds, other signaling factors, and a factor which can control functions of other cell accepting the exosome. It is considered that, therefore, the exosome can be used as a new biomarker source for diagnosing diseases.

For example, Patent Document 1 (Japanese Unexamined Patent Application, First Publication No. 2013-102768) and Patent Document 3 (Published Japanese Translation No. 2010-534480 of the PCT International Publication) disclose a method of diagnosing cancer or a harmful pregnancy outcome by analyzing miRNA in an exosome.

Patent Document 2 (Published Japanese Translation No. 2011-524164 of the PCT International Publication) discloses a method of measuring each RNA for determining the efficiency of a treatment using a small interfering RNA (siRNA)/miRNA treatment agent.

Patent Document 4 (Published Japanese Translation No. 2013-516619 of the PCT International Publication) discloses a method of detecting a protein marker which is an index of a risk causing the onset of a cardiovascular event.

Patent Document 5 (Published Japanese Translation No. 2010-517048 of the PCT International Publication) discloses a method of diagnosing an autoantibody production-related disease such as cancer or infertility by measuring a level of immunoreactive autoantibodies.

Patent Document 6 (Japanese Unexamined Patent Application, First Publication No. 2013-7698) discloses a method of detecting an endoplasmic reticulum stress response and a renal disease relating to the response by measuring urinary exosomal aquaporin 1.

The exosome can be separated and prepared from an exosome-containing sample by a separation technique using a density difference such as ultracentrifugation or density gradient ultracentrifugation. Furthermore, the exosome can also be separated by the method described in Patent Document 7 (Published Japanese Translation No. 2003-531864 of the PCT International Publication) or Patent Document 8 (Published Japanese Translation No. 2002-535665 of the PCT International Publication). In addition, a kit of separating and purifying an exosome is commercially available (for example, ExoQuick manufactured by System Biosciences, Inc. or Total Exosome Isolation manufactured by Life Technologies Corporation).

SUMMARY OF THE INVENTION

In a case where an extracellular vesicle is separated from a sample, by separating an extracellular vesicle by a separation technique using a density difference such as ultracentrifugation or a density gradient ultracentrifugation, a separated extracellular vesicle can be prepared. Furthermore, a kit of separating and purifying an extracellular vesicle from a sample in a simple manner is commercially available.

The ultracentrifugation, the density gradient ultracentrifugation, or the like require a complicated operation procedure of separating an extracellular vesicle and takes a long time for separation and purification. Furthermore, the technique cannot avoid the intermixing of foreign substances other than the extracellular vesicle and has a problem with a degree of purification or reproducibility. In addition, the commercially available purification kit which separates an extracellular vesicle in a simple manner has an insufficient degree of purification and lacks reliability.

A technique of separating an extracellular vesicle from a sample by using the bonding between the extracellular vesicle and an antibody is not necessarily effective for a wide variety of extracellular vesicles.

The present invention has been made in consideration of the above circumstances, and objects thereof are to provide a lipid membrane structure and a lipid-membrane-structure-immobilization carrier which enable vesicles to be efficiently fused with each other and to provide a method of fusing vesicles, a method of separating a vesicle, a method of detecting a vesicle, and a method of moving a vesicle that use the lipid membrane structure and the lipid-membrane-structure-immobilization carrier.

A method of separating a vesicle according to a first aspect of the present invention, includes: bringing either a vesicular-shaped lipid membrane structure containing a membrane-fusogenic lipid capable of being fused with a vesicle having a lipid bilayer membrane or a lipid-membrane-structure-immobilization carrier, in which a lipid membrane structure containing a membrane-fusogenic lipid capable of being fused with a vesicle having a lipid bilayer membrane is immobilized on a carrier into contact with a sample having the vesicle such that membrane fusion occurs between the lipid membrane structure and the vesicle.

A fusant obtained by the membrane fusion between the lipid membrane structure and the vesicle may be separated from the sample by using any of external attractive force, size, weight, and affinity.

A method of detecting a vesicle according to a second aspect of the present invention, includes: detecting a fusant generated by the membrane fusion between the lipid membrane structure and the vesicle in the method for separating a vesicle according to the first aspect.

A method of moving a vesicle according to a third aspect of the present invention, includes: bringing a vesicular-shaped lipid membrane structure containing a membrane-fusogenic lipid capable of being fused with a vesicle having a lipid bilayer membrane, and a characteristic-imparting substance into contact with the vesicle such that membrane fusion occurs between the lipid membrane structure and the vesicle; and attracting a fusant generated by the membrane fusion between the lipid membrane structure and the vesicle to a predetermined field by using characteristics imparted or changed by the characteristic-imparting substance contained in the fusant.

The predetermined field may be a recess portion provided on a substrate.

The predetermined field may be a lipid-membrane-structure-immobilization substrate, in which the vesicular-shaped lipid membrane structure containing a membrane-fusogenic lipid capable of being fused with a vesicle having a lipid bilayer membrane is immobilized on a substrate, and the fusant may be fused with the lipid membrane structure immobilized on the substrate.

The recess portion may be provided with a membrane-fusogenic lipid capable of being fused with a vesicle having a lipid bilayer membrane such that an opening portion of the recess portion on a surface of the substrate is closed, and the fusant may be fused with the lipid membrane structure on the substrate.

A method of detecting a vesicle according to a fourth aspect of the present invention includes detecting the fusant in the predetermined field in the method of moving a vesicle according to the third aspect.

A reaction reagent may be disposed in the predetermined field, a reaction may be caused between the reaction reagent and a constituent of the fusant, and the reaction or a reaction product generated by the reaction may be detected.

The predetermined field may be a recess portion formed on a substrate, and the reaction reagent may be contained in the recess portion.

The predetermined field may be a lipid-membrane-structure-immobilization substrate in which a vesicular-shaped lipid membrane structure containing a membrane-fusogenic lipid capable of being fused with a vesicle having a lipid bilayer membrane is immobilized on a substrate, the reaction reagent may be contain in the lipid membrane structure, membrane fusion may be caused between the fusant and the lipid membrane structure, a reaction may be caused between the reaction reagent and a constituent of the vesicle by the membrane fusion between the fusant and the lipid membrane structure, and the reaction or a reaction product generated by the reaction may be detected.

A lipid-membrane-structure-immobilization carrier according to a fifth aspect of the present invention includes a lipid membrane structure containing a membrane-fusogenic lipid capable of being fused with a vesicle having a lipid bilayer membrane, the lipid membrane structure being immobilized on a carrier.

The carrier may be a substrate, a recess portion may be formed on the substrate, and the lipid membrane structure may be contained in the recess portion.

The carrier may be a substrate, a recess portion may be formed on the substrate, and the lipid membrane structure may be immobilized such that an opening portion of the recess portion on a surface of the substrate is closed.

A lipid membrane structure according to a sixth aspect of the present invention includes a membrane-fusogenic lipid capable of being fused with a vesicle having a lipid bilayer membrane.

A method of fusing vesicles according to a seventh aspect of the present invention, includes: bringing either a lipid membrane structure immobilized in the lipid-membrane-structure-immobilization carrier according to the fifth aspect or the lipid membrane structure according to the sixth aspect into contact with the vesicle such that membrane fusion occurs between the lipid membrane structure and the vesicle.

A liquid containing the vesicle may be mixed with an additive inducing membrane fusion such that the lipid membrane structure and the vesicle contact each other.

The lipid membrane structure may contain a membrane fusion-inducing substance.

A method of detecting a vesicle according to an eighth aspect of the present invention, includes bringing a lipid membrane structure containing a membrane-fusogenic lipid capable of being fused with a vesicle having a lipid bilayer membrane into contact with a vesicle immobilization carrier in which a vesicle is immobilized on a carrier such that membrane fusion occurs between the lipid membrane structure and the vesicle; and detecting a fusant generated by the membrane fusion between the lipid membrane structure and the vesicle.

The lipid membrane structure may contain a reaction reagent reacting with a constituent of the vesicle, the lipid membrane structure may be brought into contact with the vesicle such that membrane fusion occurs between the lipid membrane structure and the vesicle, a reaction may be caused between the reaction reagent and a constituent of the vesicle by the membrane fusion between the lipid membrane structure and the vesicle, and the reaction or a reaction product generated by the reaction may be detected.

A method of detecting a vesicle according to a ninth aspect of the present invention, includes: attracting a vesicular-shaped lipid membrane structure containing a membrane-fusogenic lipid capable of being fused with a vesicle having a lipid bilayer membrane, a characteristic-imparting substance, and a reaction reagent to a predetermined field by using characteristics imparted or changed by the characteristic-imparting substance contained in the lipid membrane structure; disposing the vesicle in the predetermined field; bringing the lipid membrane structure into contact with the vesicle in the predetermined field such that membrane fusion occurs between the lipid membrane structure and the vesicle; causing a reaction between the reaction reagent and a constituent of the vesicle by the membrane fusion between the lipid membrane structure and the vesicle; and detecting the reaction or a reaction product generated by the reaction.

Other aspects of the present invention may be as below.

(1) A lipid membrane structure containing a membrane-fusogenic lipid to be fused with a vesicle having a lipid bilayer membrane.

(2) The lipid membrane structure described in (1), in which the vesicle having a lipid bilayer membrane is an extracellular vesicle.

(3) The lipid membrane structure described in (1) or (2) that has a vesicular shape.

(4) The lipid membrane structure described in any one of (1) to (3) further containing a characteristic-imparting substance.

(5) The lipid membrane structure described in any one of (1) to (4) further containing a membrane fusion-inducing substance.

(6) The lipid membrane structure described in any one of (1) to (5) further containing a reaction reagent reacting with a constituent of the vesicle.

(7) A lipid-membrane-structure-immobilization carrier in which the lipid membrane structure described in any one of (1) to (6) is immobilized.

(8) The lipid-membrane-structure-immobilization carrier described in (7), in which the carrier is a substrate, a recess portion is formed on the substrate, and the lipid membrane structure is contained in the recess portion.

(9) The lipid-membrane-structure-immobilization carrier described in (7), in which the carrier is a substrate, a recess portion is formed on the substrate, and the lipid membrane structure is immobilized such that an opening portion of the recess portion on a surface of the substrate is closed.

(10) A method of fusing vesicles, in which either the lipid membrane structure described in any one of (1) to (6) or the lipid membrane structure immobilized in the lipid-membrane-structure-immobilization carrier described in any one of (7) to (9) is brought into contact with the vesicle such that membrane fusion occurs between the lipid membrane structure and the vesicle.

(11) The method of fusing vesicles described in (10), a liquid containing the vesicle is mixed with an additive inducing membrane fusion such that the lipid membrane structure and the vesicle contact each other.

(12) The method of fusing vesicles described in (10) or (11), in which the lipid membrane structure contains a membrane fusion-inducing substance.

(13) A method of separating a vesicle, in which either a vesicular-shaped lipid membrane structure which contains a membrane-fusogenic lipid to be fused with a vesicle having a lipid bilayer membrane or a lipid-membrane-structure-immobilization carrier in which a vesicular-shaped lipid membrane structure containing a membrane-fusogenic lipid to be fused with a vesicle having a lipid bilayer membrane is immobilized on a carrier is brought into contact with a sample containing the vesicle such that membrane fusion occurs between the lipid membrane structure and the vesicle.

(14) The method of separating a vesicle described in (13), in which a fusant obtained by the membrane fusion between the lipid membrane structure and the vesicle is separated from the sample by using any of an external attractive force, size, weight, and affinity.

(15) A method of detecting a vesicle, in which either a lipid membrane structure containing a membrane-fusogenic lipid to be fused with a vesicle having a lipid bilayer membrane or a lipid-membrane-structure-immobilization carrier in which the lipid membrane structure is immobilized on a carrier is brought into contact with the vesicle such that membrane fusion occurs between the lipid membrane structure and the vesicle, and a fusant generated by the membrane fusion between the lipid membrane structure and the vesicle is detected.

(16) A method of detecting a vesicle, in which a lipid membrane structure containing a membrane-fusogenic lipid to be fused with a vesicle having a lipid bilayer membrane is brought into contact with a vesicle immobilization carrier in which a vesicle is immobilized on a carrier such that membrane fusion occurs between the lipid membrane structure and the vesicle, and a fusant generated by the membrane fusion between the lipid membrane structure and the vesicle is detected.

(17) The method of detecting a vesicle described in (15) or (16), in which the lipid membrane structure contains a reaction reagent reacting with a constituent of the vesicle, the lipid membrane structure and the vesicle are brought into contact with each other such that membrane fusion occurs between the lipid membrane structure and the vesicle, a reaction is caused between the reaction reagent and a constituent of the vesicle by the membrane fusion between the lipid membrane structure and the vesicle, and the reaction or a reaction product generated by the reaction is detected.

(18) A method of moving a vesicle, in which a vesicular-shaped lipid membrane structure containing a membrane-fusogenic lipid to be fused with a vesicle having a lipid bilayer membrane, and a characteristic-imparting substance is brought into contact with the vesicle such that membrane fusion occurs between the lipid membrane structure and the vesicle, and by using characteristics imparted or changed by the characteristic-imparting substance contained in a fusant generated by the membrane fusion between the lipid membrane structure and the vesicle, the fusant is attracted to a predetermined field.

(19) The method of moving a vesicle described in (18), in which the predetermined field is a recess portion provided in a substrate.

(20) The method of moving a vesicle described in (18) or (19), in which the predetermined field is a lipid-membrane-structure-immobilization carrier in which the vesicular-shaped lipid membrane structure containing a membrane-fusogenic lipid to be fused with a vesicle having a lipid bilayer membrane is immobilized on a substrate, and the fusant is fused with the lipid membrane structure immobilized on the substrate.

(21) The method of moving a vesicle described in (19), in which the recess portion is provided with the membrane-fusogenic lipid to be fused with a vesicle having a lipid bilayer membrane such that an opening portion of the recess portion on a surface of the substrate is closed, and the fusant is fused with the lipid membrane structure on the substrate.

(22) A method of detecting a vesicle, in which a vesicular-shaped lipid membrane structure containing a membrane-fusogenic lipid to be fused with a vesicle having a lipid bilayer membrane, and a characteristic-imparting substance is brought into contact with the vesicle such that membrane fusion occurs between the lipid membrane structure and the vesicle; by using characteristics imparted or changed by the characteristic-imparting substance contained in a fusant generated by the membrane fusion between the lipid membrane structure and the vesicle, the fusant is attracted to a predetermined field; and the fusant is detected in the predetermined field.

(23) The method of detecting a vesicle described in (22), in which a reaction reagent is disposed in the predetermined field, a reaction is caused between the reaction reagent and a constituent of the fusant, and the reaction or a reaction product generated by the reaction is detected.

(24) The method of detecting a vesicle described in (23), in which the predetermined field is a recess portion formed on the substrate, and the reaction reagent is contained in the recess portion.

(25) The method of detecting a vesicle described in (23) or (24), in which the predetermined field is a lipid-membrane-structure-immobilization substrate in which a vesicular-shaped lipid membrane structure containing a membrane-fusogenic lipid to be fused with a vesicle having a lipid bilayer membrane is immobilized on a substrate, the reaction reagent is contained in the lipid membrane structure, membrane fusion is caused between the fusant and the lipid membrane structure, a reaction is caused between the reaction reagent and a constituent of the vesicle by the membrane fusion between the fusant and the lipid membrane structure, and the reaction or a reaction product generated by the reaction is detected.

(26) A method of detecting a vesicle, in which a vesicular-shaped lipid membrane structure containing a membrane-fusogenic lipid to be fused with a vesicle having a lipid bilayer membrane, and a characteristic-imparting substance is attracted to a predetermined field by using characteristics imparted or changed by the characteristic-imparting substance contained in the lipid membrane structure, the vesicle is disposed in the predetermined field, the lipid membrane structure and the vesicle are brought into contact with each other in the predetermined field such that membrane fusion occurs between the lipid membrane structure and the vesicle, a reaction is caused between the reaction reagent and a constituent of the vesicle by the membrane fusion between the lipid membrane structure and the vesicle, and the reaction or a reaction product generated by the reaction is detected.

(27) A method of evaluating a vesicle, includes: forming either a first complex composed of a first vesicle having a first immobilization substance and a first subject vesicle having a first detection substance different from the first immobilization substance or a second complex composed of a second vesicle having a second detection substance and a second subject vesicle having a second immobilization substance different from the second detection substance, immobilizing the first complex to a carrier by using the first immobilization substance or the second complex to a carrier by using the second immobilization substance, and detecting the first detection substance or the second detection substance.

(28) The method of evaluating a vesicle described in (27), in which in all of the first vesicle, the second vesicle, the first subject vesicle, and the second subject vesicle are a lipid bilayer membrane.

(29) The method of evaluating a vesicle described in (27) or (28), in which the first complex formed of the first vesicle and the first subject vesicle and the second complex formed of the second vesicle and the second subject vesicle are artificially fused with each other.

(30) The method of evaluating a vesicle described in any one of (27) to (29), in which a liquid containing the first vesicle is mixed with a first additive inducing membrane fusion such that the first vesicle and the first subject vesicle contact each other, and a liquid containing the second vesicle is mixed with a second additive inducing membrane fusion such that the second vesicle and the second subject vesicle contact each other.

(31) The method of evaluating a vesicle described in any one of (27) to (30), in which at least one of the first vesicle and the second vesicle contains a membrane fusion-inducing substance.

(32) The method of evaluating a vesicle described in any one of (27) to (31), in which the carrier has a substance, which is specifically bonded to at least one of the first immobilization substance and the second immobilization substance, on a surface of the carrier, and the carrier is at least any one of a substrate, a film, a magnetic bead, a silica bead, a glass bead, and a polymer.

(33) The method of evaluating a vesicle described in any one of (27) to (32), in which at least one of the first detection substance and the second detection substance is 1 or more types of substance selected from the group consisting of a fluorescent substance, a colorimetric substance, a luminous substance, an oxidation-reduction substance, an antigen, a nucleic acid, and an enzyme.

(34) The method of evaluating a vesicle described in (33), including a substance reacting with at least one of the first detection substance and the second detection substance.

(35) The method of evaluating a vesicle described in (34), in which the substance reacting with at least one of the first detection substance and the second detection substance is 1 or more types of substance selected from the group consisting of a matrix, a chemiluminescent substance, an oxidation-reduction substance, and an antibody.

(36) The method of evaluating a vesicle described in any one of (27) to (32), in which at least one of the first detection substance and the second detection substance is selected from 2 types of fluorescent substance having a wavelength range in which fluorescence intensity increases before and after membrane fusion.

By using the lipid membrane structure or the lipid-membrane-structure-immobilization carrier according to the aforementioned aspects of the present invention, it is possible to efficiently fuse, separate, detect, and move extracellular vesicles in a simple manner. Furthermore, according to the method of fusing vesicles, the method of separating a vesicle, the method of detecting a vesicle, and the method of moving a vesicle according to the aforementioned aspects of the present invention, it is possible to efficiently fuse, separate, detect, and move extracellular vesicles in a simple manner.

DETAILED DESCRIPTION OF THE INVENTION

<<Lipid Membrane Structure>>

Figure 1:
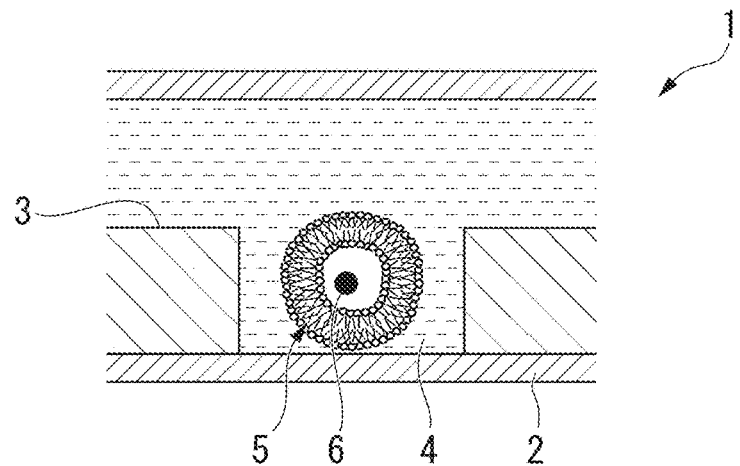
FIG. 1 is a view schematically showing a lipid-membrane-structure-immobilization carrier according to a second embodiment.

The lipid membrane structure according to the first embodiment of the present invention contains a membrane-fusogenic lipid to be fused (capable of being fused) with a vesicle having a lipid bilayer membrane.

The lipid membrane structure has a lipid membrane in which a lipid membrane structure to be fused with a vesicle is formed in 1 or more layers.

It is preferable that, in the lipid membrane structure, a lipid bilayer composed of 2 layers of lipid membrane overlapping each other be formed. The lipid bilayer is represented by the cell membrane of a cell. The membrane fusogenicity of the lipid membrane structure may be a property of the lipid contained in the lipid membrane structure or a property of the entire lipid membrane.

Examples of the lipid forming the lipid membrane of the lipid membrane structure include a phospholipid, a glycolipid, a sterol, a saturated or unsaturated fatty acid, and the like.

Examples of the phospholipid include phosphatidylcholine such as dioleoylphosphatidylcholine, dipalmitoylphosphatidylcholine, or dilauroylphosphatidylcholine; phosphatidylglycerol such as dioleoylphosphatidylglycerol, dipalmitoylphosphatidylglycerol, or dilauroylphosphatidylglycerol; phosphatidylethanolamine such as dioleoylphosphatidylethanolamine, dipalmitoylphosphatidylethanolamine, or dilauroylphosphatidylethanolamine; phosphatidylserine such as dioleoylphosphatidylserine, dipalmitoylphosphatidylserine, or dilauroylphosphatidylserine; phosphatidic acid, phosphatidylinositol, cardiolipin, sphingomyelin, egg yolk lecithin, soybean lecithin, the above phospholipids that are hydrogenated, and the like.

Examples of the glycolipid include glyceroglycolipid such as sulfoxyribosyl glyceride, diglycosyl diglyceride, or digalactosyl diglyceride; sphyngoglycolipid such as galactosyl cerebroside, lactosyl cerebroside, or ganglioside; and the like.

Examples of the sterol include an animal-derived sterol such as cholesterol, cholesterol succinate, or lanosterol; a plant-derived sterol such as stigmasterol, sitosterol, or campesterol; and a microorganism-derived sterol such as zymosterol or ergosterol.

Examples of the saturated or unsaturated fatty acid include a saturated or unsaturated fatty acid having 12 to 20 carbon atoms, such as palmitic acid, oleic acid, or stearic acid.

Although the membrane fusion between a lipid bilayer membrane and a lipid membrane is a phenomenon that occurs spontaneously, it is preferable that the lipid membrane undergo a change of the membrane structure due to an external stimulus such as pH, temperature, charge, or light and cause membrane fusion.

The lipid membrane relating to the lipid membrane structure according to the present invention may contain any substance in addition to the lipid forming the lipid membrane, as long as the formation of the lipid membrane is not hindered. Examples of such a substance include a membrane stabilizer, a charged substance, a membrane protein, and the like. If the lipid membrane contains these substances, the membrane stability can be improved, or the charge of the membrane can be controlled.

Examples of the membrane stabilizer include a sterol, a glycerin, or a fatty acid ester thereof, and the like.

Specific examples of the sterol are the same as described above. Examples of the fatty acid ester of glycerin include triolein, trioctanoin, and the like.

Examples of the charged substance that imparts a positive charge include a saturated or unsaturated aliphatic amine such as stearylamine or oleylamine; a saturated or unsaturated cationic synthetic lipid such as dioleyl trimethylammonium propane; and the like.

Examples of the charged substance that imparts a negative charge include phosphatidic acid, phosphatidylserine, phosphatidylinositol, and the like.

Examples of the membrane protein include a peripheral membrane protein, integral membrane protein, and the like.

The vesicle having a lipid bilayer membrane has the shape of a vesicle formed of a lipid bilayer membrane. The vesicle may be an artificially made vesicle or a natural vesicle. Examples of the natural vesicle include a cell having a lipid bilayer membrane, a unicellular organism, a microorganism, a fungus, a bacterium, a virus, an organelle, a vacuole, a membrane vesicle, a vesicle, a transport vesicle, an aggregate of these, and the like. Examples of the artificially made vesicle having a lipid bilayer membrane include a liposome, a vesicle obtained by pulverizing a natural vesicle and making again a vesicular-shaped vesicle, and the like. The vesicle having a lipid bilayer membrane may be a vesicle derived from a vesicle having a lipid bilayer membrane. As will be described later, the vesicle having a lipid bilayer membrane includes a fusant composed of a vesicle having a lipid bilayer membrane and the lipid membrane structure according to the present embodiment.

The vesicle having a lipid bilayer membrane is preferably an extracellular vesicle. The extracellular vesicle is a cell which exists outside a cell and is preferably secreted from a cell. Examples of the cell secreted to the outside of a cell include a vesicle, a microvesicle, a nanovesicle, a secretory vesicle, an exosome, and the like.

In the present embodiment and the specification of the present application, the extracellular vesicle includes a vesicle derived from an extracellular vesicle. Examples of the vesicle derived from an extracellular vesicle include a complex generated by the membrane fusion that occurs between an extracellular vesicle and other vesicles having a lipid bilayer membrane, and a vesicle cut off from an extracellular vesicle. Herein, other vesicles having a lipid bilayer membrane include the lipid membrane structure according to the present embodiment.

The extracellular vesicle fused with the aforementioned lipid membrane structure is preferably an exosome. It is known that the exosome contains a protein, mRNA, micro RNA (miRNA), DNA, and the like and can transmit information to a cell at the destination by moving from cell to cell.

The lipid membrane structure can be, as a lipid membrane, for example, a self-supported membrane, a membrane on an interface such as an aqueous solution, an oil, or a highly concentrated solution, or a membrane on a substrate such as a metal, glass, or plastic.

The shape of the lipid membrane structure is not particularly limited, and examples thereof include a sheet-shaped lipid membrane in which a lipid to be fused with the vesicle having a lipid bilayer membrane is formed in at least 1 or more planar layers. The lipid membrane structure preferably has a sheet shape or a vesicular shape, and more preferably has a vesicular shape.

For example, in a case where a lipid having a lipid bilayer membrane has a hydrophilic portion and a hydrophobic portion, the lipid bilayer membrane existing in an aqueous solution is arrayed such that the hydrophilic portion is disposed on the surface of the lipid bilayer membrane and the hydrophobic portion is disposed in the inside of the lipid bilayer membrane. At this time, if the layer is vesicular, the layer does not have an end portion in which the hydrophobic portion becomes the surface of the lipid bilayer membrane. Accordingly, compared to a sheet-shaped layer, the vesicular layer can more stably exist in a liquid. Therefore, because a vesicular-shaped lipid membrane structure can stably exist in a solvent, the lipid membrane structure more preferably has a vesicular shape. Because the vesicular-shaped lipid membrane structure can stably exist in a solvent, mobility thereof is also excellent. Accordingly, the vesicular-shaped lipid membrane structure has more opportunities to contact with the vesicle having a lipid bilayer membrane such that fusion occurs, and hence the efficiency of fusion between the lipid membrane structure and the vesicle can be improved. Furthermore, if the lipid membrane structure has a vesicular shape, a substance can be held in the vesicle.

When the lipid membrane structure has a vesicular shape, a maximum diameter as a size of the vesicular-shaped lipid membrane structure is preferably 10 nm to 100 μm, and more preferably 50 nm to 10 μm. When the maximum diameter as a size of the vesicular-shaped lipid membrane structure is 50 nm to 10 μm, the maximum diameter is more preferably 50 nm to 500 nm or 1 μm to 10 μm.

Examples of a suitable combination of the lipid membrane structure and the vesicle having a lipid bilayer membrane to be fused with the lipid membrane structure include a combination in which the vesicle having a lipid bilayer membrane is an extracellular vesicle, and the lipid membrane structure is an artificial vesicle.

Examples of the suitable combination also include a combination in which the vesicle having a lipid bilayer membrane is a vesicle derived from a vesicle having a lipid bilayer membrane and a fusant of an extracellular vesicle and an artificial vesicle, and the lipid membrane structure is an artificial vesicle.

It is preferable that the lipid membrane structure contain a characteristic-imparting substance. The state where the lipid membrane structure contains a characteristic-imparting substance includes a state where the characteristic-imparting substance is contained in the lipid membrane of the lipid membrane structure, a state where the characteristic-imparting substance is anchored on the outside of the lipid membrane of the lipid membrane structure, and, in a case where the lipid membrane structure is vesicular, a state where the characteristic-imparting substance is contained in the lipid membrane structure.

The characteristic-imparting substance is a substance that imparts characteristics to a vesicle which can be fused with the lipid membrane structure. Furthermore, the characteristic-imparting substance is a substance which adds new characteristics to a vesicle fused with the lipid membrane structure or changes a level of existing characteristics of the vesicle. Examples of the characteristics imparted by the characteristic-imparting substance include weight, size, affinity with a certain substance, charge, magnetism, and a combination of these. In some cases, all of the weight, size, affinity with a certain substance, charge, and magnetism exemplified above can be considered as the existing characteristics of the vesicle which can be fused with the lipid membrane structure. Therefore, it can be said that due to the characteristic-imparting substance, a level of these characteristics is changed. Among the above, the affinity and magnetism easily become new characteristics different from the existing characteristics of the vesicle which can be fused with the lipid membrane structure. Therefore, as characteristics imparted by the characteristic-imparting substance, affinity and magnetism are more preferable.

Examples of the characteristic-imparting substance more specifically include a metal compound, a magnetic substance, a charged substance, and an affinity substance.

The metal compound includes 1 or more metal substances or metal particles having any shape. It is preferable that a specific gravity of the metal compound be greater than that of a vesicle which can be fused with the lipid membrane structure. As the metal compound, metal colloid particles such as gold colloid are preferable. As a metal colloid other than gold colloid particles, for example, fine particles of various magnetic metals are used.

The magnetic substance includes 1 or more magnetic substances or magnetizable particles having any shape and is attracted by magnetic force-generating means. As the magnetic substance, ferrite particles such as magnetite are preferable. As a magnetic substance other than ferrite, for example, fine particles of various magnetic metals or various magnetic compounds are used.

Examples of the charged substance include a charged lipid, a peptide, a protein, a nucleic acid, a polymer, and the like.

The affinity substance is a substance capable of being bonded to and desorbed from a certain substance. Examples thereof include an affinity tag such as a His-tag and a protein such as an antibody.

The characteristic-imparting substance can impart the characteristics of the characteristic-imparting substance to a vesicle capable of being fused with the lipid membrane structure. Therefore, by using the imparted characteristics, it is possible to separate, detect, and move the vesicle.

It is preferable that the lipid membrane structure contain a membrane fusion-inducing substance. The state where the lipid membrane structure contains a membrane fusion-inducing substance includes a state where the membrane fusion-inducing substance is contained in the lipid membrane of the lipid membrane structure, a state were the membrane fusion-inducing substance is anchored on the outside of the lipid membrane of the lipid membrane structure, and, in a case where the lipid membrane structure is vesicular, a state where the membrane fusion-inducing substance contains the characteristic-imparting substance in the inside of the membrane fusion-inducing substance. From the viewpoint of inducing membrane fusion, it is preferable that the membrane fusion-inducing substance exist on the surface of the lipid membrane structure. That is, it is preferable that the membrane fusion-inducing substance be contained in the lipid membrane of the lipid membrane structure.

Inducing membrane fusion includes inducing and accelerating membrane fusion between the lipid membrane structure and a vesicle, and increasing the frequency of the membrane fusion.

The membrane fusion-inducing substance is, for example, a membrane-permeable peptide, a membrane-fusogenic polymer, a virus-derived protein, or a stimulus-sensitive peptide or polymer.

Examples of the membrane-permeable peptide include polyarginine, polylysine, polyhistidine, and the like. Examples of the membrane-fusogenic polymer include polyethylene glycol, polypropylene glycol, and the like. Examples of the virus-derived protein include a HA protein and the like. Examples of the stimulus-sensitive peptide include a GALA peptide, a KALA peptide, and the like. Examples of the stimulus-sensitive polymer include poly-N-isopropylacrylamide and the like.

By the membrane fusion-inducing substance, it is possible to improve the efficiency of membrane fusion during the membrane fusion between an extracellular vesicle and an artificial vesicle.

It is preferable that the lipid membrane structure contain a reaction reagent reacting with a constituent of a vesicle.

The state where the lipid membrane structure contains a reaction reagent includes a state where the reaction reagent is contained in the lipid membrane of the lipid membrane structure, a state where the reaction reagent is anchored on the outside of the lipid membrane of the lipid membrane structure, and, in a case where the lipid membrane structure is vesicular, a state where the reaction reagent is contained in the lipid membrane structure.

The constituent of a vesicle includes a component constituting the lipid membrane of the vesicle and contents of the vesicle.

The reaction reagent is, for example, a reagent for biochemical analysis such as a reagent for nucleic acid analysis or a reagent for protein analysis. The reagent for nucleic acid analysis is, for example, an Invader reaction reagent, and the reagent for protein analysis is, for example, an immunoassay reagent.

If the lipid membrane structure contains a reaction reagent reacting with the constituent of a vesicle, it is possible to detect the existence of the vesicle and the existence of the content or constituent of the vesicle.

<<Lipid-Membrane-Structure-Immobilization Carrier>>

In the lipid-membrane-structure-immobilization carrier according to the second to fourth embodiments of the present invention, the lipid membrane structure according to the first embodiment is immobilized. The lipid membrane structure according to the second to fourth embodiments is the same as the lipid membrane structure described in the first embodiment, and hence the description thereof will not be repeated.

The carrier is not particularly limited as long as the lipid membrane structure can be immobilized thereon. The carrier may have a plate shape or a particle shape. Examples of materials constituting the carrier include glass, porous glass, an organic compound, a polymer compound, a resin, gel, a metal, a semiconductor, an inorganic compound, a mixture of an organic compound and an inorganic compound, and the like.

As the resin, a resin used in a container for a biochemical reaction or the like is preferable. Examples thereof include polypropylene, polystyrene, polycarbonate, and the like.

In a case where the carrier is likely to hinder the reaction, it is preferable to prepare a carrier by coating the surface of the carrier with a resin or the like which does not hinder the reaction.

The carrier can also be used as a substrate, which will be described later.

The lipid-membrane-structure-immobilization carrier may further include external attractive force-generating means such as electrophoretic force-generating means or magnetic force-generating means. Examples of the electrophoretic force-generating means include an electrophoresis device, an electric field-applying device, an electrode, and the like. Examples of the magnetic force-generating means include a magnetic force-generating device, a permanent magnet such as magnetite, ferrite, neodymium, an electromagnet, and the like.

If the lipid-membrane-structure-immobilization carrier includes the external attractive force-generating means, it is possible to control the behavior of a lipid membrane structure, a vesicle, and a fusant of the lipid membrane structure and the vesicle. Accordingly, the lipid membrane structure and a vesicle to be fused with the lipid membrane structure can be fused with each other with higher efficiency.

The lipid-membrane-structure-immobilization carrier may further include a reaction reagent reacting with a constituent of a vesicle. Examples of the reaction reagent include the same reagents as those described above as the reagents that can be contained in the lipid membrane structure.

If the lipid-membrane-structure-immobilization carrier contains the reaction reagent, it is possible to detect the existence of a vesicle that has undergone membrane fusion with the lipid membrane structure relating to the lipid-membrane-immobilization carrier, and the existence of the content or constituent of a vesicle.

Second Embodiment

In the lipid-membrane-structure-immobilization carrier according to the second embodiment of the present invention, the aforementioned carrier is a substrate, a recess portion is formed on the substrate, and a vesicular-shaped lipid membrane structure containing a membrane-fusogenic lipid to be fused with a vesicle having a lipid bilayer membrane is contained in the recess portion. The lipid-membrane-structure-immobilization carrier may have a plurality of recess portions containing the lipid membrane structure.

FIG. 1 is a schematic view showing a lipid-membrane-structure-immobilization substrate 1 according to the present embodiment. A substrate 2 is a plate-shaped member in which a recess portion 4 is formed on a surface 3. An artificial vesicle 5 (vesicular-shaped lipid membrane structure) is contained in the recess portion 4 and is immobilized on the bottom surface of the recess portion 4. Examples of methods of immobilizing the artificial vesicle 5 include physical adsorption by hydrophobic interaction, electrostatic adsorption by electrostatic interaction, chemical adsorption by chemical bonding, and the like. The artificial vesicle 5 contains a reaction reagent 6 reacting with a constituent of a vesicle to be fused with the artificial vesicle 5.

Third Embodiment

In the lipid-membrane-structure-immobilization carrier according to the third embodiment of the present invention, the aforementioned carrier is a substrate, and a sheet-shaped lipid membrane structure is immobilized on the substrate.

Figure 2:
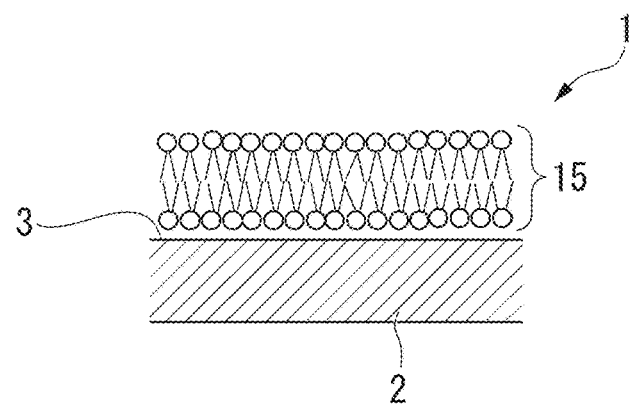
FIG. 2 is a view schematically showing a lipid-membrane-structure-immobilization carrier according to a third embodiment.

FIG. 2 is a schematic view showing the lipid-membrane-structure-immobilization substrate 1 of the present embodiment. A fused membrane 15 (sheet-shaped lipid membrane structure) is immobilized on the surface 3 of the substrate 2.

Fourth Embodiment

In the lipid-membrane-structure-immobilization carrier according to the fourth embodiment of the present invention, the aforementioned carrier is a substrate, a recess portion is formed on the substrate, and a lipid membrane structure containing a membrane-fusogenic lipid to be fused with a vesicle having a lipid bilayer membrane is immobilized such that an opening portion of the recess portion on a surface of the substrate surface is closed. The substrate in the lipid-membrane-structure-immobilization carrier according to the fourth embodiment includes external attractive force-generating means (external attractive force-generating device) on a side (position) opposite to a side on which the lipid membrane structure is positioned on the substrate.

Figure 3:
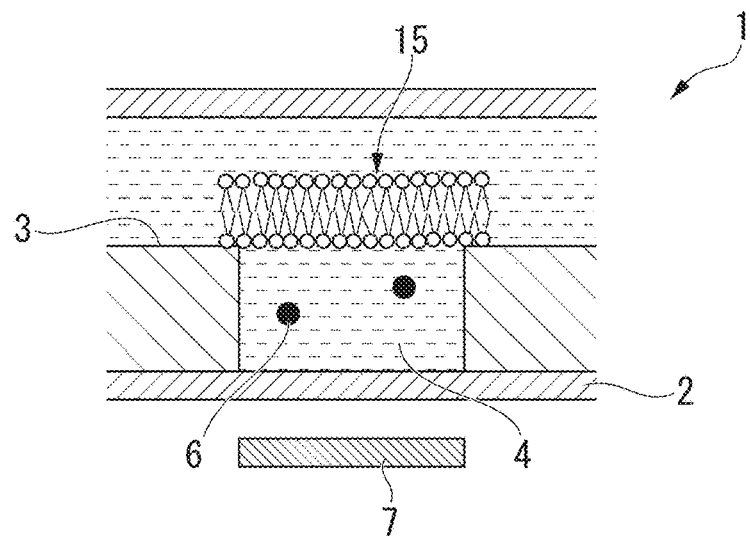
FIG. 3 is a view schematically showing a lipid-membrane-structure-immobilization carrier according to a fourth embodiment.

FIG. 3 is a schematic view showing the lipid-membrane-structure-immobilization substrate 1 according to the present embodiment. The substrate 2 is a plate-shaped member in which the recess portion 4 is formed on the surface 3. The fused membrane 15 (sheet-shaped lipid membrane structure) is immobilized such that an opening portion of the recess portion 4 on the substrate surface 3 is closed. The reaction reagent 6 is contained in the recess portion 4 closed with the fused membrane 15. The substrate includes a magnetic force-generating device 7 (external attractive force-generating means) on a surface opposite to a surface on which the lipid membrane structure of the substrate 2 is positioned. The lipid-membrane-structure-immobilization carrier may have a plurality of recess portions in which the lipid membrane structures are immobilized.

<<Method of Fusing Vesicles>>

The method of fusing vesicles according to the fifth to seventh embodiments of the present invention is a method of bringing either the lipid membrane structure according to the aforementioned embodiment or the lipid membrane structure immobilized on the lipid-membrane-structure-immobilization carrier according to the aforementioned embodiment into contact with the aforementioned vesicle such that membrane fusion occurs between the lipid membrane structure and the vesicle. As the lipid membrane structure and the lipid-membrane-structure-immobilization carrier, the same ones as described above in <<Lipid membrane structure (first embodiment)>> and <<Lipid-membrane-structure-immobilization carrier (second to fourth embodiments)>> can be exemplified.

Particularly, a lipid membrane structure containing a membrane fusion-inducing substance and a lipid-membrane-structure-immobilization carrier in which a lipid membrane structure containing a membrane fusion-inducing substance is immobilized on a carrier can be exemplified as suitable ones.

Fifth Embodiment

Figure 4:
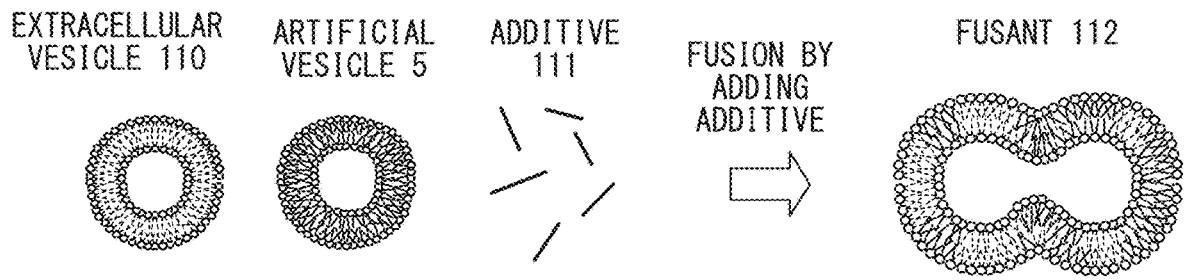
FIG. 4 is a view for illustrating a method of fusing vesicles according to a fifth embodiment.

In the method of fusing vesicles according to the fifth embodiment of the present invention, a liquid containing an extracellular vesicle (vesicle) 110 is mixed with an additive 111 inducing membrane fusion, thereby bringing the artificial vesicle (lipid membrane structure) 5 and the vesicle 110 into contact with each other (FIG. 4).

Inducing membrane fusion includes inducing and accelerating the membrane fusion between the lipid membrane structure and the vesicle, and increasing the frequency of the membrane fusion.

As the liquid containing a vesicle, it is possible to use any material which can contain a vesicle, such as bio-derived sample solutions such as blood, serum, and urine and solutions prepared from these.

The liquid containing the vesicle 110 and the additive 111 may be mixed in advance before the lipid membrane structure 5 and the vesicle 110 are brought into contact with each other, mixed while the lipid membrane structure 5 and the vesicle 110 are being brought into contact with each other, or mixed after the lipid membrane structure 5 and the vesicle 110 are brought into contact with each other.

In a case where the liquid containing the vesicle 110 is mixed with the additive 111 before the lipid membrane structure 5 and the vesicle 110 are brought into contact with each other, for example, a serum containing the extracellular vesicle 110 is mixed with the additive 111 so as to obtain a mixed liquid of the serum and the additive 111, and then the mixed liquid is added to a solution containing the artificial vesicle 5. Likewise, a bio-derived serum is mixed with the additive 111 so as to obtain a mixed liquid of the serum and the additive 111, and then the mixed liquid is brought into contact with an artificial-vesicle-immobilization substrate 201.

In a case where the liquid containing the vesicle 110 is mixed with the additive 111 after the lipid membrane structure 5 and the vesicle 110 are brought into contact with each other, for example, a bio-derived serum and a solution containing the artificial vesicle 5 are mixed together so as to obtain a mixed liquid of the serum and the solution containing the artificial vesicle 5, and then the additive 111 is added to the mixed liquid. Likewise, a bio-derived serum is brought into contact with the artificial-vesicle-immobilization substrate 201, and then the additive 111 is added to the serum contacting with the artificial-vesicle-immobilization substrate 201.

In the present embodiment, an artificial-vesicle-immobilization substrate 1 can also be used.

Examples of the additive 111 include a pH adjuster, a surfactant, a metal compound, and the like.

Examples of the pH adjuster include various buffer solutions. Examples of the surfactant include TRITON®, TWEEN®, and the like.

Examples of the metal compound include a calcium-containing compound (for example, calcium chloride), a magnesium-containing compound, and the like.

By adding the additive 111 to a field of fusion between the extracellular vesicle 110 and the artificial vesicle 5, it is possible to arbitrarily control the membrane fusion.

Sixth Embodiment

Figure 5:
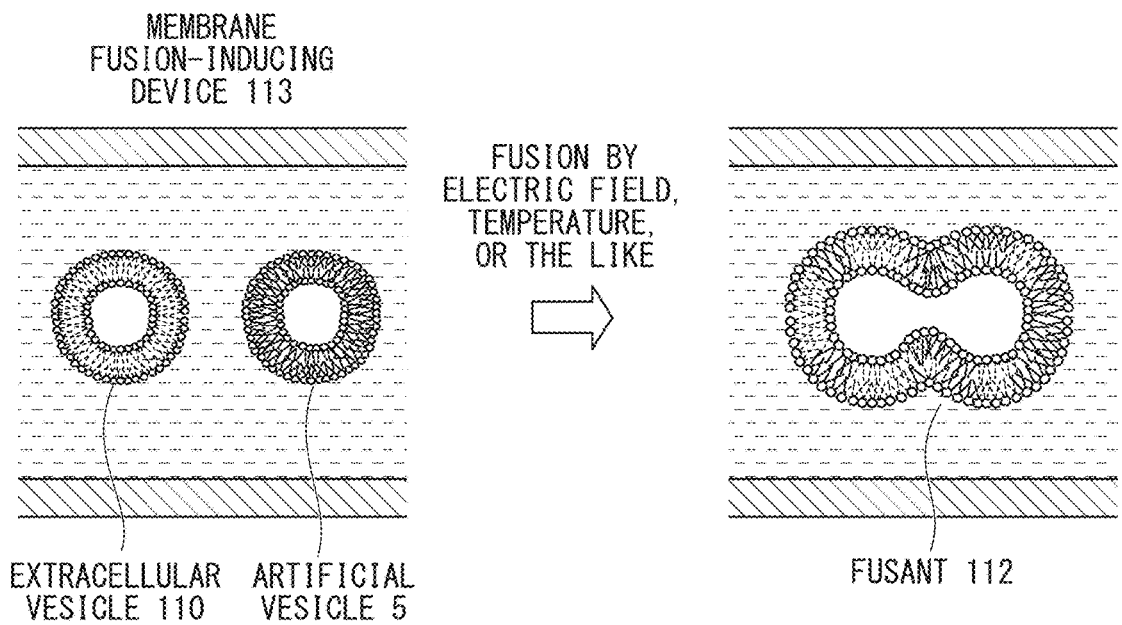
FIG. 5 is a view for illustrating a method of fusing vesicles according to a sixth embodiment.

In the method of fusing vesicles of the sixth embodiment of the present invention, in order to cause membrane fusion between the vesicle 110 and the artificial vesicle 5, a membrane fusion-inducing device 113 is used (FIG. 5). The membrane fusion-inducing device 113 is, for example, an electric field-applying device, a heating device, or the like.

Inducing membrane fusion includes inducing and accelerating the membrane fusion between the lipid membrane structure 5 and the vesicle 110, and increasing the frequency of the membrane fusion.

By arbitrarily changing the membrane structure by using the membrane fusion-inducing device 113, it is possible to control the timing of the membrane fusion, the vesicle that will undergo membrane fusion, the efficiency of the membrane fusion, and the like.

Seventh Embodiment

Figure 6:
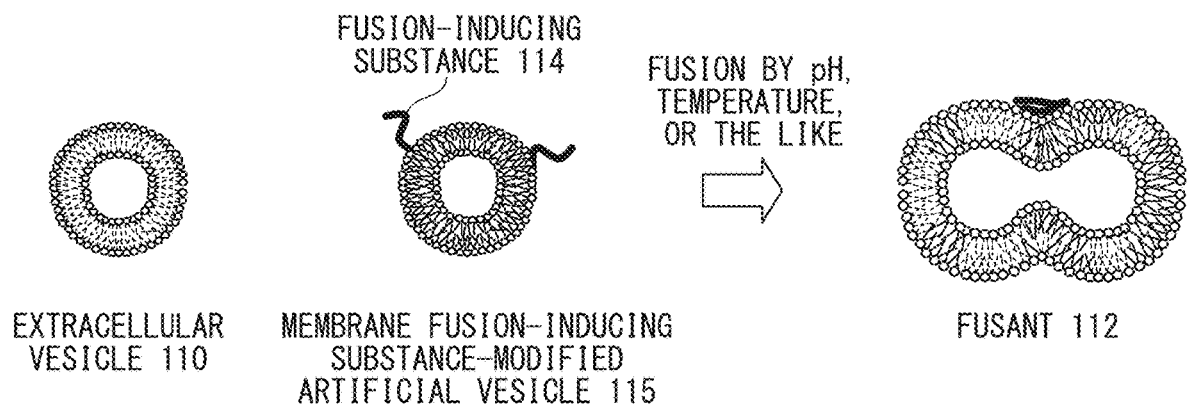
FIG. 6 is a view for illustrating a method of fusing vesicles according to a seventh embodiment.

In the seventh embodiment of the present invention, in order to cause membrane fusion between the extracellular vesicle 110 and the artificial vesicle, the artificial vesicle 115 modified with a membrane fusion-inducing substance 114 is used (FIG. 6). Examples of the membrane fusion-inducing substance 114 include a membrane-permeable peptide, a membrane-fusogenic polymer, a virus-derived protein, a stimulus-sensitive peptide or polymer, and the like.

By the membrane fusion-inducing substance 114, it is possible to improve the membrane fusion efficiency during the membrane fusion between the extracellular vesicle 110 and the artificial vesicle.

<<Method of Separating a Vesicle>>

In the method of separating a vesicle according to the eighth to thirteenth embodiments of the present invention, either a vesicular-shaped lipid membrane structure, which contains a membrane-fusogenic lipid to be fused with a vesicle having a lipid bilayer membrane, or a lipid-membrane-structure-immobilization carrier, in which a vesicular-shaped lipid membrane structure containing a membrane-fusogenic lipid to be fused with a vesicle having a lipid bilayer membrane is immobilized on a carrier is brought into contact with a sample containing the vesicle such that membrane fusion occurs between the lipid membrane structure and the vesicle.

The method of separating a vesicle in the present embodiment and the specification of the present application is a method of separating a vesicle from a sample containing a vesicle. As the sample containing a vesicle, for example, it is possible to use any materials that are likely to contain a vesicle, such as bio-derived sample solutions such as blood, serum, and urine and solutions prepared from these.

As the lipid membrane structure and the lipid-membrane-structure-immobilization carrier relating to the method of separating a vesicle according to the present embodiment, the same ones as described above in <<Lipid membrane structure (first embodiment)>> and <<Lipid-membrane-structure-immobilization carrier (second to fourth embodiments)>> can be exemplified. Particularly, a lipid membrane structure containing a characteristic-imparting substance and a lipid-membrane-structure-immobilization carrier in which a lipid membrane structure containing a characteristic-imparting substance is immobilized can be exemplified as suitable ones.

For the membrane fusion between the lipid membrane structure and the vesicle relating to the method of separating a vesicle according to the present embodiment, it is possible to suitably use the method described above in <<Method of fusing vesicles (fifth to seventh embodiments)>>.

The separated vesicle can be recovered as a fusant of the lipid membrane structure and the vesicle.

Eighth Embodiment

Figure 7:
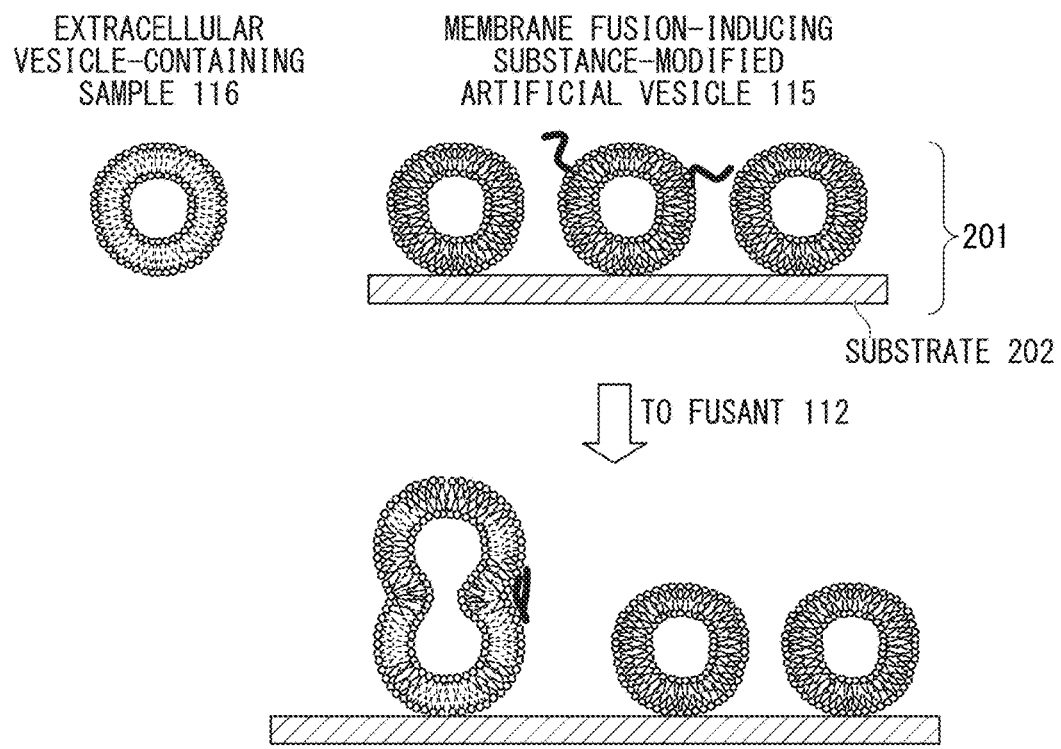
FIG. 7 is a view for illustrating a method of separating a vesicle according to an eighth embodiment.

The method of separating a vesicle according to the eighth embodiment of the present invention is a method of bringing the artificial-vesicle-immobilization substrate 201, in which an artificial vesicle (lipid membrane structure) is immobilized on the substrate 202, into contact with a sample 116 containing the extracellular vesicle (vesicle) 110 such that membrane fusion occurs between the artificial vesicle and the extracellular vesicle 110 (FIG. 7). As shown in FIG. 7, the artificial vesicle 115 may contain the membrane fusion-inducing substance 114.

By bringing the extracellular vesicle 110 contained in the sample 116 into contact with the artificial vesicle 115 such that membrane fusion occurs between the extracellular vesicle 110 and the artificial vesicle 115, it is possible to rapidly separate the extracellular vesicle 110 contained in the sample 116 in a simple manner.

The artificial-vesicle-immobilization substrate 201 is obtained by immobilizing an artificial vesicle by using a substrate 202 not having a recess portion 4 of the lipid-membrane-structure-immobilization carrier 1 shown in FIG. 1.

Furthermore, it is possible to make a differentiation between the extracellular vesicle 110 not being fused with the artificial vesicle 115 and a fusant 112 obtained by the fusion between the extracellular vesicle 110 and the artificial vesicle 115.

In the present embodiment, a case where the artificial-vesicle-immobilization substrate 201 and the sample 116 are brought into contact with each other is exemplified. However, even in a case where an artificial vesicle which is not immobilized on a carrier such as a substrate is brought into contact with the sample 116, due to the fusion between the artificial vesicle and the extracellular vesicle 110, for example, the size of the extracellular vesicle 110 can be increased. Therefore, in this case, the vesicle separation efficiency can be further improved than in a case where a conventional method of separating a vesicle is used. In addition, the method of separating a vesicle according to the present embodiment can be used in combination with the conventional method of separating a vesicle. For example, the method of separating a vesicle according to the present embodiment can also be used as a pre-treatment method of the conventional method of separating a vesicle.

Examples of the conventional method of separating a vesicle that is suitable for being used in combination with the method of separating a vesicle according to the present embodiment include ultracentrifugation, density gradient ultracentrifugation, filtration centrifugation, and the like.

In the method of separating a vesicle according to the present embodiment, the fusant 112 obtained by causing membrane fusion between the lipid membrane structure and the vesicle may be separated from the sample 116 by using any of external attractive force, size, weight, and affinity.

Ninth Embodiment

The method of separating a vesicle according to the ninth embodiment of the present invention is a method of bringing an artificial vesicle (lipid membrane structure) into contact with a sample containing the extracellular vesicle (vesicle) 110 such that membrane fusion occurs between the artificial vesicle and the extracellular vesicle 110, and separating the fusant 112 obtained by the membrane fusion from the sample by using weight.

In the present embodiment, in order to efficiently separate the fusant 112 of the extracellular vesicle 110 and the artificial vesicle, an artificial vesicle 118 containing a metal compound 117 or the like is used. Examples of the metal compound 117 include the same ones as described as the characteristic-imparting substance in <<Lipid membrane structure (first embodiment)>>.

Figure 8:
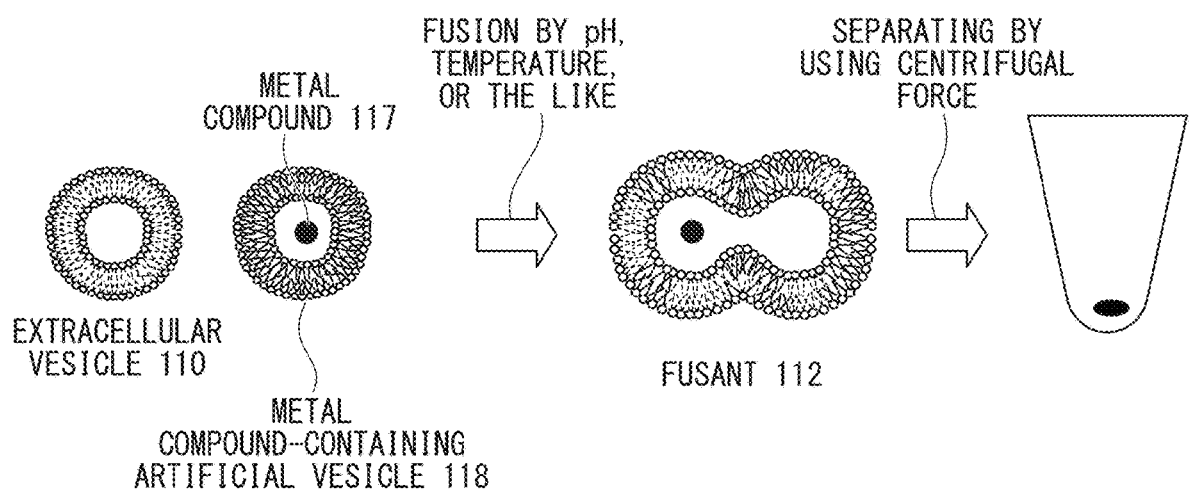
FIG. 8 is a view for illustrating a method of separating a vesicle according to a ninth embodiment.

FIG. 8 is a schematic view illustrating the method of separating a vesicle according to the present embodiment. The artificial vesicle contains the metal compound 117. A solution containing a metal compound-containing artificial vesicle 118 is mixed with a sample solution containing the extracellular vesicle 110 such that the metal compound-containing artificial vesicle 118 and the extracellular vesicle 110 contact each other, thereby obtaining the fusant 112. At this time, membrane fusion may be induced by controlling a pH, a temperature, and the like.

In the present embodiment, in order to separate the fusant 112, which is obtained by the membrane fusion between the extracellular vesicle 110 and the artificial vesicle 118 containing the metal compound 117, from the sample, centrifugal force-generating means is used. As the centrifugal force-generating means, a centrifuge or the like is preferable. The fusant 112 can be more easily separated from the sample by the centrifugal force-generating means.

According to the method of separating a vesicle of the present embodiment, it is possible to make a differentiation between the extracellular vesicle 110 not being fused with the artificial vesicle and the fusant 112 obtained by the fusion between the extracellular vesicle 110 and the artificial vesicle.

Tenth Embodiment

The method of separating a vesicle according to the tenth embodiment of the present invention is a method of bringing an artificial vesicle (lipid membrane structure) into contact with a sample containing the extracellular vesicle (vesicle) 110 such that membrane fusion occurs between the artificial vesicle and the extracellular vesicle 110, and separating the fusant 112 obtained by the membrane fusion from the sample by using a charge (external attraction force).

In the present embodiment, in order to efficiently separate the fusant 112 of the extracellular vesicle 110 and the artificial vesicle, an artificial vesicle 120 modified with a charged substance 119 is used. The charged substance 119 is the same as the charged substance described above as the characteristic-imparting substance in <<Lipid membrane structure (first embodiment)>>.

Figure 9:
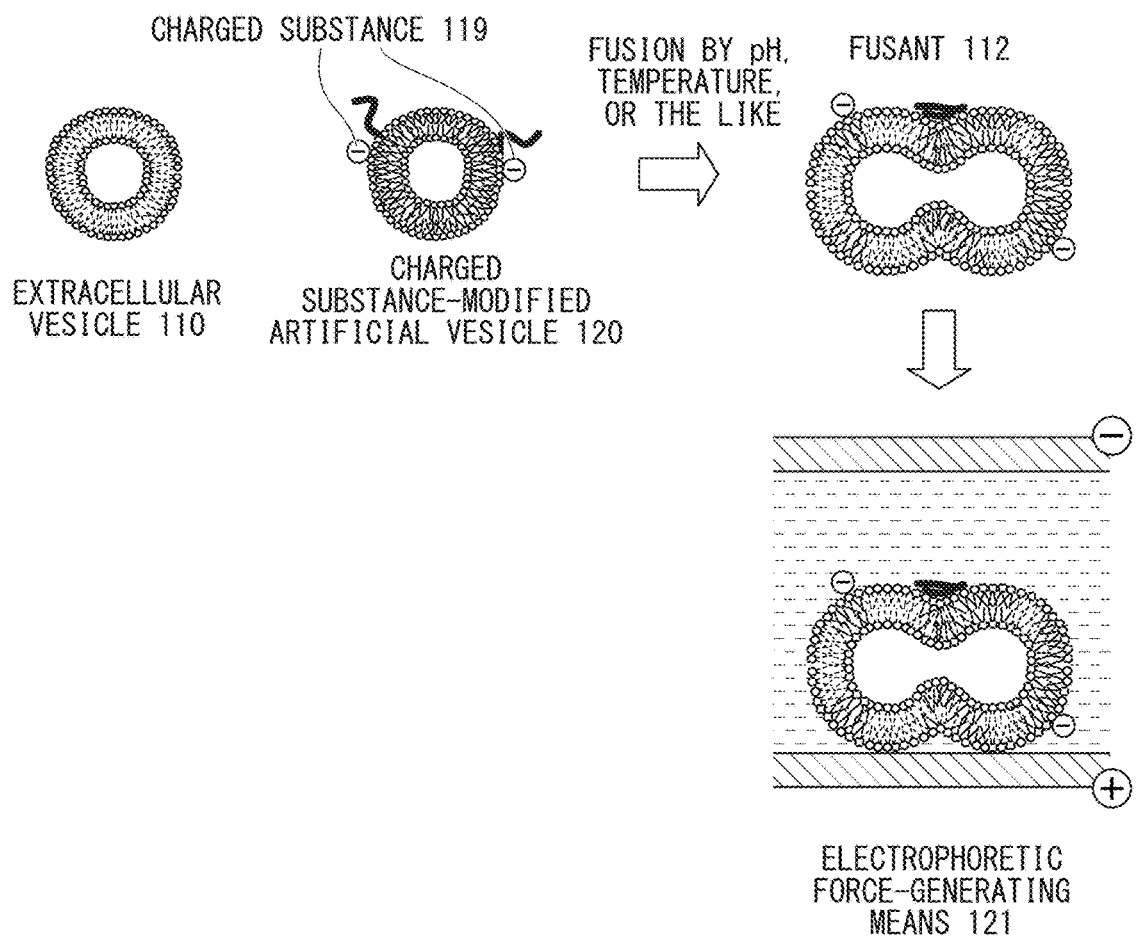
FIG. 9 is a view for illustrating a method of separating a vesicle according to a tenth embodiment.

FIG. 9 is a schematic view illustrating the method of separating a vesicle according to the present embodiment. The artificial vesicle is modified with the charged substance 119. A solution containing the charged substance-modified artificial vesicle 120 is mixed with a sample solution containing the extracellular vesicle 110 such that the charged substance-modified artificial vesicle 120 and the extracellular vesicle 110 contact each other, thereby obtaining the fusant 112. At this time, membrane fusion may be induced by controlling the pH, temperature, and the like.

In the present embodiment, in order to separate the fusant 112, which is obtained by the fusion between the extracellular vesicle 110 and the artificial vesicle modified with the charged substance 119, from the sample, electrophoretic force-generating means 121 is used. The electrophoretic force-generating means 121 is, for example, an electrophoresis device or an electric field-applying device. The behavior of the fusant 112 can be controlled by the electrophoretic force-generating means 121. For example, because the artificial vesicle 120 shown in FIG. 9 is modified with the charged substance 119 that is negatively charged, the characteristics of the fusant 112 have changed such that the fusant 112 is easily attracted to a positive electrode side, and the fusant 112 can be more easily separated from the sample.

According to the method of separating a vesicle of the present embodiment, it is also possible to make a differentiation between the extracellular vesicle 110 not being fused with the artificial vesicle and the fusant 112 obtained by the fusion between the extracellular vesicle 110 and the artificial vesicle.

Eleventh Embodiment

The method of separating a vesicle according to the eleventh embodiment of the present invention is a method of bringing an artificial vesicle (lipid membrane structure) 5 into contact with a sample containing the extracellular vesicle (vesicle) 110 such that membrane fusion occurs between the artificial vesicle 5 and the extracellular vesicle 110, and separating the fusant 112 obtained by the membrane fusion from the sample by using size.

In the present embodiment, in order to efficiently separate the fusant 112 of the extracellular vesicle 110 and the artificial vesicle 5, an artificial vesicle 5 that enables size exclusion is used. The artificial vesicle that enables size exclusion is preferably an artificial vesicle 5 having a size larger than the size of a foreign substance such as a protein in the sample, and more preferably an artificial vesicle having a size larger than the size of the extracellular vesicle 110.

Figure 10:
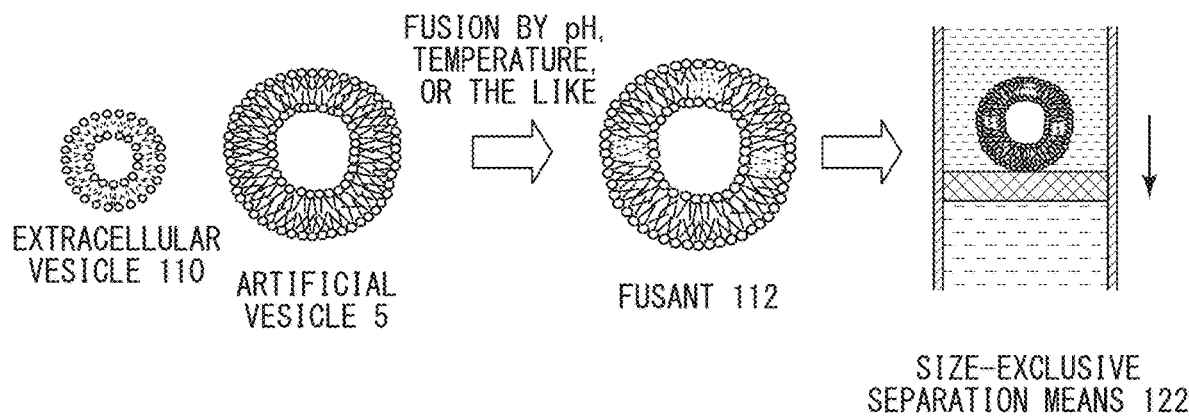
FIG. 10 is a view for illustrating a method of separating a vesicle according to an eleventh embodiment.

FIG. 10 is a schematic view illustrating the method of separating a vesicle according to the present embodiment. The artificial vesicle 5 has a size larger than the size of the extracellular vesicle 110. A solution containing the artificial vesicle 5 is mixed with a sample solution containing the extracellular vesicle 110 such that the artificial vesicle 5 and the extracellular vesicle 110 contact each other, thereby obtaining the fusant 112. At this time, membrane fusion may be induced by controlling the pH, temperature, and the like.

In the present embodiment, in order to separate the fusant 112 of the extracellular vesicle 110 and the artificial vesicle 5 that enables size exclusion, size-exclusive separation means 122 is used. The size-exclusive separation means 122 is, for example, a column. The fusant 112 can be easily separated from the sample by the size-exclusive separation means 122.

According to the method of separating a vesicle of the present embodiment, it is also possible to make a differentiation between the extracellular vesicle 110 not being fused with the artificial vesicle 5 and the fusant 112 obtained by the fusion between the extracellular vesicle 110 and the artificial vesicle 5.

Twelfth Embodiment

The method of separating a vesicle according to the twelfth embodiment of the present invention is a method of bringing an artificial vesicle (lipid membrane structure) into contact with a sample containing the extracellular vesicle (vesicle) 110 such that membrane fusion occurs between the artificial vesicle and the extracellular vesicle 110, and separating the fusant 112 obtained by the membrane fusion from the sample by using affinity.

In the present embodiment, in order to separate the fusant 112 of the extracellular vesicle 110 and the artificial vesicle, an artificial vesicle 124 modified with an affinity substance 123 is used. The affinity substance 123 is a substance capable of being bonded to a specific substance and preferably a substance capable of being bonded to and desorbed from a specific substance. The affinity substance 123 is the same as those described above as the characteristic-imparting substance in <<Lipid membrane structure (first embodiment)>>.

Figure 11:
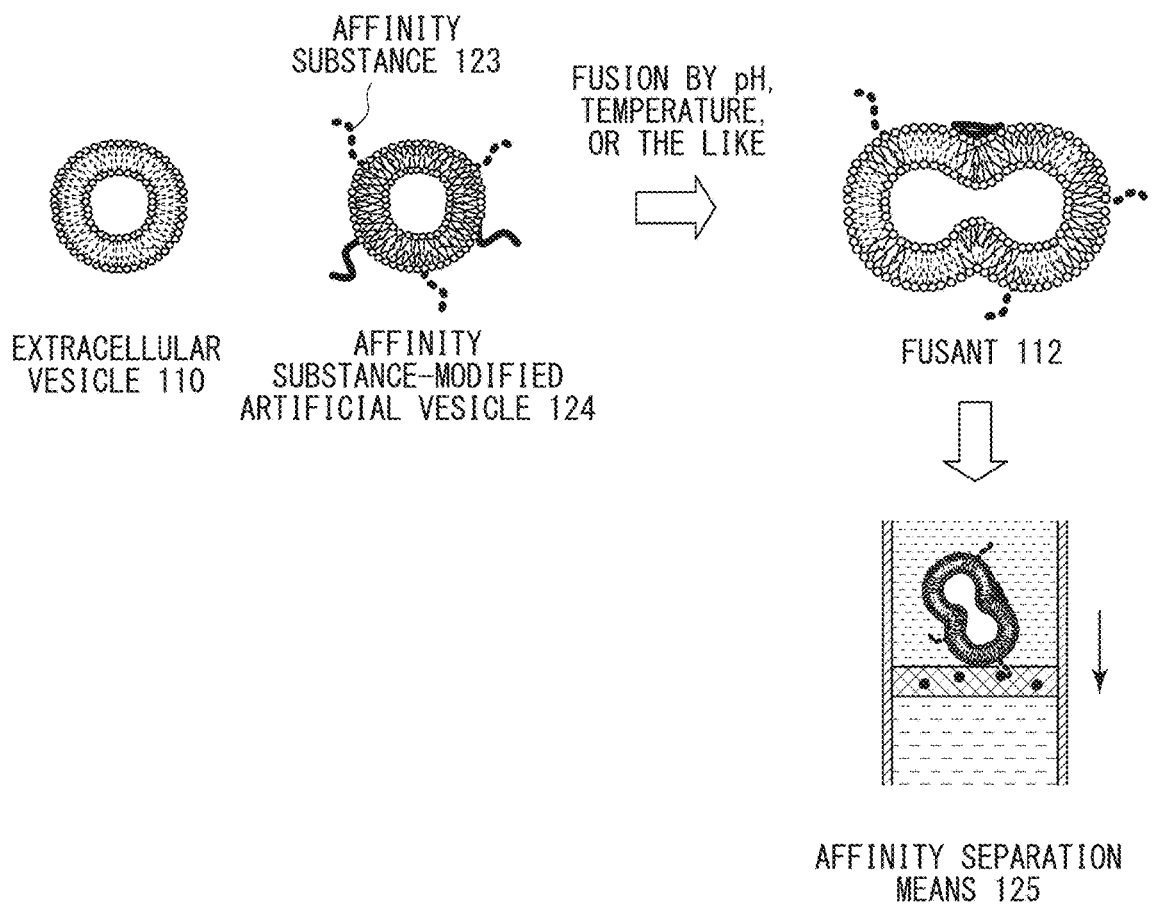
FIG. 11 is a view for illustrating a method of separating a vesicle according to a twelfth embodiment.

FIG. 11 is a schematic view illustrating the method of separating a vesicle of the present embodiment. The artificial vesicle is modified with the affinity substance 123. A solution containing the charged substance-modified artificial vesicle 120 is mixed with a sample solution containing the extracellular vesicle 110 such that the charged substance-modified artificial vesicle 120 and the extracellular vesicle 110 contact each other, thereby obtaining the fusant 112 modified with the affinity substance 123. At this time, membrane fusion may be induced by controlling a pH, a temperature, and the like.

In the present embodiment, in order to separate a fusant 112, which is obtained by the fusion between of the extracellular vesicle 110 and the artificial vesicle 124 modified with the affinity substance 123, from the sample, affinity separation means 125 is used. As the affinity separation means 125, a column including a substance capable being bonded to the affinity substance 123 or the like is preferable. By using the affinity separation means 125, the fusant 112 can be easily separated and recovered from the sample.

According to the method of separating a vesicle of the present embodiment, it is also possible to make a differentiation between the extracellular vesicle 110 not being fused with the artificial vesicle and the fusant 112 obtained by the fusion between the extracellular vesicle 110 and the artificial vesicle.

Thirteenth Embodiment

The method of separating a vesicle according to the thirteenth embodiment of the present invention is a method of bringing an artificial vesicle (lipid membrane structure) into contact with a sample containing the extracellular vesicle (vesicle) 110 such that membrane fusion occurs between the artificial vesicle and the extracellular vesicle 110, and separating the fusant 112 obtained by the membrane fusion from the sample by using magnetic force (external attractive force).

In the present embodiment, in order to efficiently separate the fusant 112 of the extracellular vesicle 110 and the artificial vesicle, an artificial vesicle 127 containing a magnetic substance 126 is used. The magnetic substance 126 is the same as the magnetic substance described above as the characteristic-imparting substance in <<Lipid membrane structure (first embodiment)>>.

Figure 12:
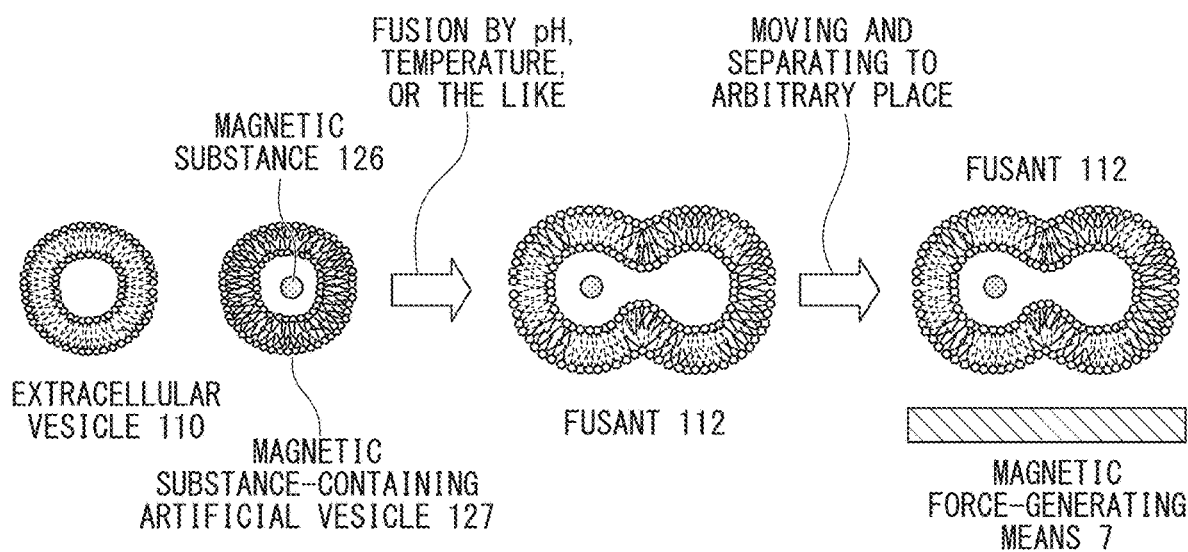
FIG. 12 is a view for illustrating a method of separating a vesicle according to a thirteenth embodiment.

FIG. 12 is a schematic view illustrating the method of separating a vesicle of the present embodiment. The artificial vesicle contains the magnetic substance 126. A solution containing the magnetic substance-containing artificial vesicle 127 is mixed with a sample solution containing the extracellular vesicle 110 such that the magnetic substance-containing artificial vesicle 127 and the extracellular vesicle 110 contact each other, thereby obtaining the fusant 112. At this time, membrane fusion may be induced by controlling a pH, a temperature, and the like.

In the present embodiment, in order to separate the fusant 112, which is obtained by the membrane fusion between the extracellular vesicle 110 and the artificial vesicle containing the magnetic substance 126, from the sample, magnetic force-generating means 7 is used. The magnetic force-generating means 7 is a permanent magnet or an electromagnet. By the magnetic force-generating means 7, the fusant 112 can be more easily separated from the sample.

According to the method of separating a vesicle of the present embodiment, it is also possible to make a differentiation between the extracellular vesicle 110 not being fused with the artificial vesicle and the fusant 112 obtained by the fusion between the extracellular vesicle 110 and the artificial vesicle.

<<Method of Detecting a Vesicle—I>>

In the method of separating a vesicle according to the fourteenth to seventeenth embodiments of the present invention, examples of the lipid membrane structure and the lipid-membrane-structure-immobilization carrier include the same ones as described above in <<Lipid membrane structure (first embodiment)>> and <<Lipid-membrane-structure-immobilization carrier (second to fourth embodiments)>>. Particularly, a lipid membrane structure which contains a reaction reagent and a lipid-membrane-structure-immobilization carrier in which a lipid membrane structure containing a reaction reagent is immobilized can be exemplified as suitable ones.

For the membrane fusion between the lipid membrane structure and the vesicle in the method of separating a vesicle according to the present embodiment, it is possible to suitably use the method described above in <<Method of fusing vesicles (fifth to seventh embodiments)>>.

Fourteenth Embodiment

In the method of detecting a vesicle according to the fourteenth embodiment of the present invention, a lipid membrane structure, which contains a membrane-fusogenic lipid to be fused with a vesicle having a lipid bilayer membrane, is brought into contact with the vesicle such that membrane fusion occurs between the lipid membrane structure and the vesicle, and the fusant 112 generated by the membrane fusion between the lipid membrane structure and the vesicle is detected.

Figure 13:
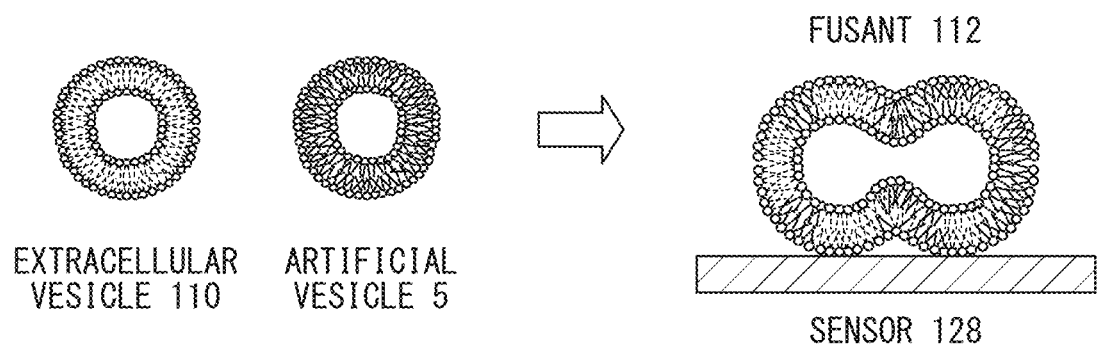
FIG. 13 is a view for illustrating a method of detecting a vesicle according to a fourteenth embodiment.

FIG. 13 is a schematic view illustrating the method of detecting a vesicle according to the present embodiment. A solution containing the artificial vesicle 5 is mixed with a sample solution containing the extracellular vesicle 110 such that the artificial vesicle 5 and the extracellular vesicle 110 contact each other and the fusant 112 is obtained, and then the fusant 112 is detected by detection means 128. The detection means 128 is, for example, a sensor using surface plasmon resonance (SPR) or a quartz crystal microbalance (QCM).

By detecting the extracellular vesicle 110 as the fusant 112, even a very small vesicle, which is not easily detected by the conventional method, can be detected, and the detection efficiency can be improved.

Fifteenth Embodiment

In the method of detecting a vesicle according to the fifteenth embodiment of the present invention, the lipid membrane structure 5, which contains a membrane-fusogenic lipid to be fused with a vesicle having a lipid bilayer membrane, is brought into contact with a vesicle immobilization carrier in which the vesicle 110 is immobilized on a carrier such that membrane fusion occurs between the lipid membrane structure and the vesicle, and the fusant 112 generated by the membrane fusion between the lipid membrane structure 5 and the vesicle 110 is detected.

Figure 14:
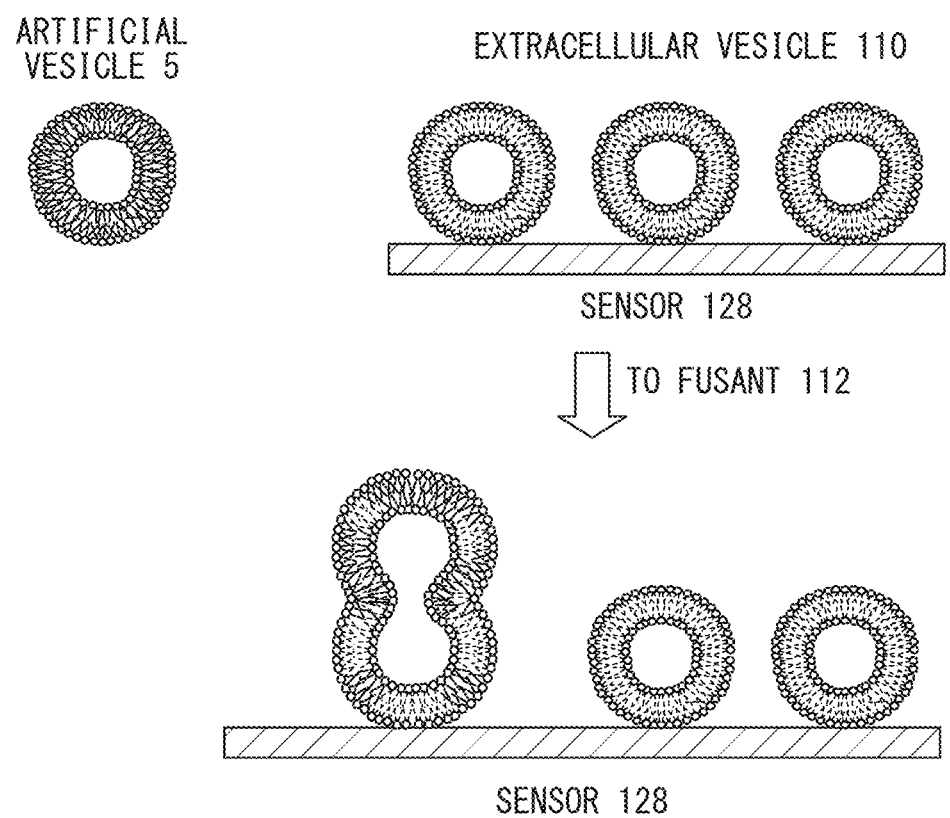
FIG. 14 is a view for illustrating a method of detecting a vesicle according to a fifteenth embodiment.

FIG. 14 is a schematic view illustrating the method of detecting a vesicle of the present embodiment. The solution containing the artificial vesicle 5 is brought into contact with an extracellular-vesicle-immobilization substrate 301 in which the extracellular vesicle 110 is immobilized on a substrate. The substrate includes the detection means 128. On the substrate, the fusant 112 of the artificial vesicle 5 and the extracellular vesicle 110 is obtained, and the fusant 112 is detected by the detection means 128. The detection means 128 is, for example, a sensor using surface plasmon resonance (SPR) or a quartz crystal microbalance (QCM).

The extracellular-vesicle-immobilization substrate 301 in which the extracellular vesicle 110 is immobilized may be obtained by a conventionally known method or obtained as a substrate, on which the vesicle (fusant) 112 derived from the extracellular vesicle 110 is immobilized, by using the method of separating a vesicle according to the embodiment described above. Examples of the substrate obtained by the embodiment described above include an extracellular-vesicle-immobilization substrate (fusant immobilization substrate) obtained by, as shown in the eighth embodiment of <<Method of separating vesicle>>, bringing the artificial-vesicle-immobilization substrate 201, in which the artificial vesicle (lipid membrane structure) 5 is immobilized on a substrate, into contact with a sample containing the extracellular vesicle (vesicle) 110 such that membrane fusion occurs between the lipid membrane structure 5 and the extracellular vesicle 110.

In this way, the extracellular vesicle 110 can be detected as the fusant 112, and the detection efficiency of the extracellular vesicle 110 can be improved.

Sixteenth Embodiment

In the method of detecting a vesicle according to the sixteenth embodiment of the present invention, the lipid membrane structure 5 contains the reaction reagent 6 reacting with a constituent of the extracellular vesicle 110, the lipid membrane structure 5 is brought into contact with the extracellular vesicle 110 such that membrane fusion occurs between the lipid membrane structure 5 and the extracellular vesicle 110, a reaction is caused between the reaction reagent 6 and the constituent of the extracellular vesicle 110 by the membrane fusion between the lipid membrane structure 5 and the extracellular vesicle 110, and the reaction or a reaction product generated by the reaction is detected.

Figure 15:
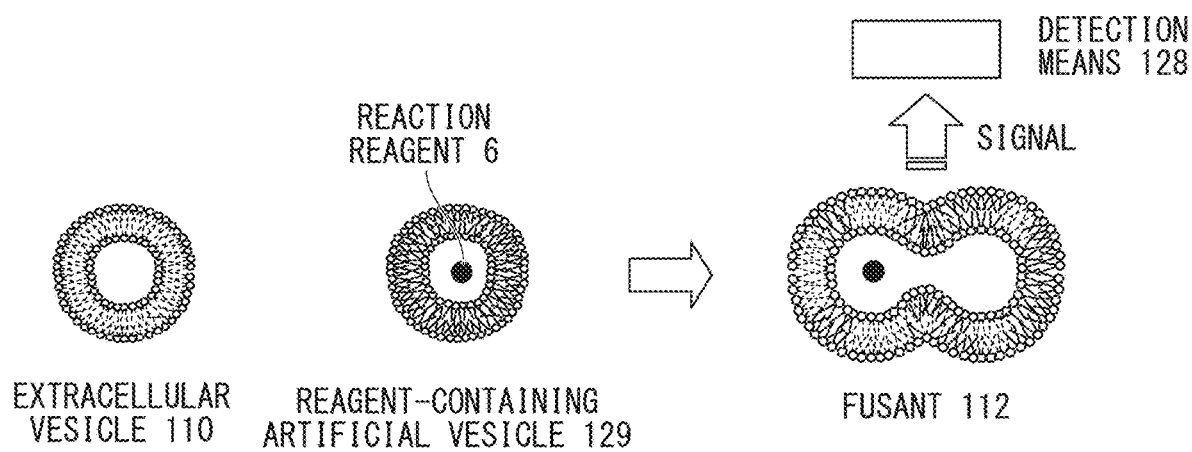
FIG. 15 is a view for illustrating a method of detecting a vesicle according to a sixteenth embodiment.

FIG. 15 is a schematic view illustrating the method of detecting a vesicle according to the present embodiment. A solution containing a reaction reagent-containing artificial vesicle 129 is mixed with a sample solution containing the extracellular vesicle 110 such that the reaction reagent-containing artificial vesicle 129 and the extracellular vesicle 110 contact each other, thereby obtaining the fusant 112. Then, the fusant 112 is detected by the detection means 128. Because the reaction reagent 6 reacts with the constituent of the extracellular vesicle 110, only after the extracellular vesicle 110 and the reaction reagent-containing artificial vesicle 129 form the fusant 112, the reaction occurs. Therefore, it is possible to detect only the fusant 112 of the extracellular vesicle 110 and the reaction reagent-containing artificial vesicle 129.

The reaction reagent 6 is the same as the reagent described above in <<Lipid membrane structure (first embodiment)>>. By reacting with the content or constituent of the extracellular vesicle 110, the reaction reagent 6 generates a signal. The generated signal is, for example, coloration, fluorescence, or an oxidation-reduction potential. The signal may be detected using the detection means 128 suitable for each signal. Examples of the detection means 128 include a CCD camera, a flow cytometer, and the like. Furthermore, by the detected signal, it is also possible to detect the fusant 112 by using a separation device such as a cell sorter.

Seventeenth Embodiment

Figure 16:
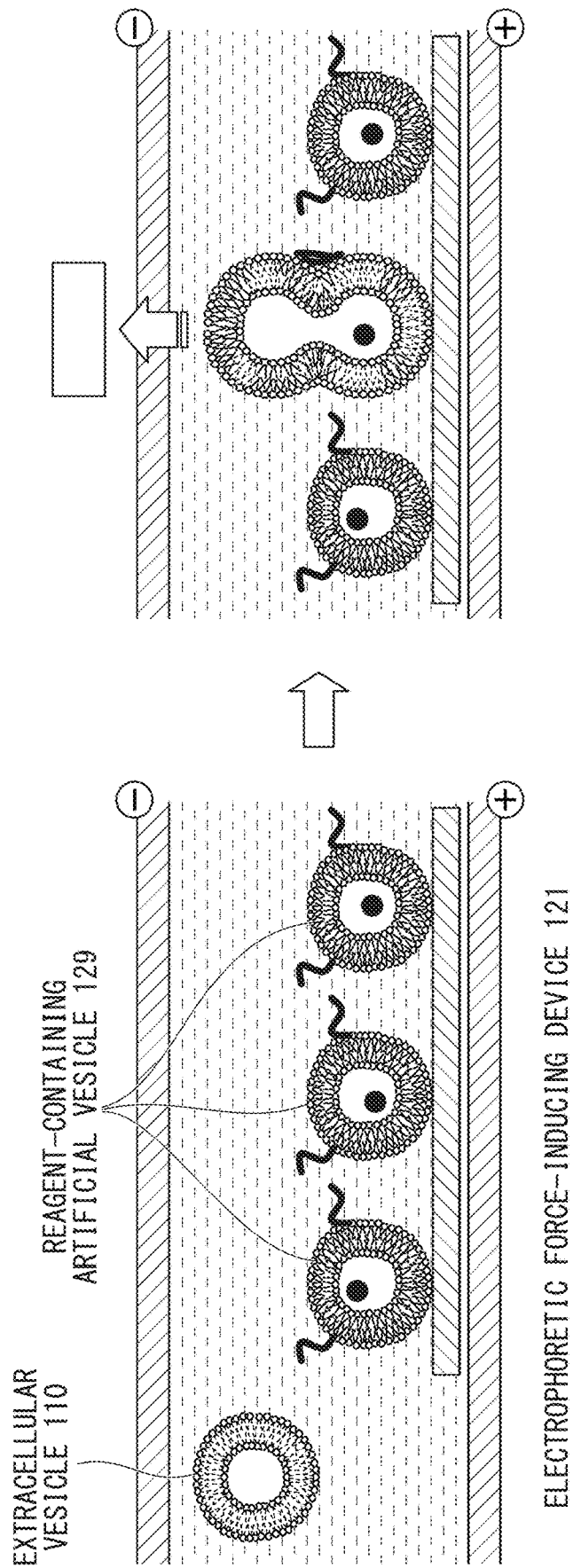
FIG. 16 is a view for illustrating a method of detecting a vesicle according to a seventeenth embodiment.

The method of detecting a vesicle according to the seventeenth embodiment of the present invention is a modification example of the method of detecting a vesicle according to the sixteenth embodiment. FIG. 16 is a schematic view illustrating the method of detecting a vesicle according to the present embodiment. The reaction reagent-containing artificial vesicle 129 is immobilized on a substrate. In the present embodiment, the electrophoretic force-generating means 121 is also used. As shown in FIG. 16, because the extracellular vesicle 110 is negatively charged, by disposing a positive electrode on the substrate side, it is possible to attract the extracellular vesicle 110 to the substrate. By using the electrophoretic force-generating means (electrophoresis device) 121, the efficiency of fusion between the reaction reagent-containing artificial vesicle 129 and the extracellular vesicle 110 can be improved. Furthermore, it is possible to shorten the time taken for the step of detecting the signal generated by the reaction between the constituent of the extracellular vesicle 110 and the reaction reagent 6, and to improve the detection efficiency.

<<Method of Moving Vesicle>>

In the method of moving a vesicle according to the eighteenth and nineteenth embodiments of the present invention, a vesicular lipid membrane structure, which contains a membrane-fusogenic lipid to be fused with a vesicle having a lipid bilayer membrane and a characteristic-imparting substance, is brought into contact with the vesicle such that membrane fusion occurs between the lipid membrane structure and the vesicle, and by using characteristics imparted or changed by the characteristic-imparting substance contained in a fusant generated by the membrane fusion between the lipid membrane structure and the vesicle, the fusant is attracted to a predetermined field.

As the lipid membrane structure in the method of moving a vesicle according to the present embodiment, the same lipid membrane structure as described above in <<Lipid membrane structure (first embodiment)>> can be exemplified. Particularly, a vesicular-shaped lipid membrane structure containing a characteristic-imparting substance can be exemplified as suitable one.

For the membrane fusion between the lipid membrane structure and the vesicle in the method of moving a vesicle according to the present embodiment, it is possible to suitably use the method described above in <<Method of fusing vesicles (fifth to seventh embodiments)>>.

The method of moving a vesicle according to the present embodiment can be performed in any liquid containing a vesicle. By being performed in a sample solution containing a vesicle, the method of moving a vesicle according to the present embodiment can function as the method of separating a vesicle from the sample.

Examples of the aforementioned predetermined field include a detection portion which includes detection means of detecting a vesicle (fusant) derived from a vesicle, a recovery portion which is for recovering a fusant, a reaction portion which is for fusing a lipid membrane structure with a vesicle, and the like. The shape of the predetermined field is not particularly limited, and examples thereof include a recess portion provided on a substrate. The recess portion is, for example, a reaction well.

The aforementioned predetermined field may include the lipid membrane structure according to the first embodiment.

For example, the predetermined field may be a lipid-membrane-structure-immobilization substrate in which a vesicular-shaped lipid membrane structure, which contains a membrane-fusogenic lipid to be fused with a vesicle having a lipid bilayer membrane, is immobilized on a substrate, and the aforementioned fusant may be fused with the lipid membrane structure immobilized on the substrate.

Alternatively, the predetermined field may be a recess portion provided on a substrate, the recess portion may be provided with a membrane-fusogenic lipid to be fused with a vesicle having a lipid bilayer membrane such that an opening portion of the recess portion on a surface of the substrate is closed, and the fusant may be fused with the lipid membrane structure on the substrate.

Eighteenth Embodiment

In the method of moving a vesicle according to the eighteenth embodiment of the present invention, a vesicular-shaped lipid membrane structure, which contains a membrane-fusogenic lipid to be fused with a vesicle having a lipid bilayer membrane and a characteristic-imparting substance, is brought into contact with the vesicle such that membrane fusion occurs between the lipid membrane structure and the vesicle, and by using characteristics imparted or changed by the characteristic-imparting substance contained in the fusant 112 generated by the membrane fusion between the lipid membrane structure and the vesicle, the fusant 112 is attracted to a predetermined field. The predetermined field is a recess portion provided on a substrate.

Figure 17:
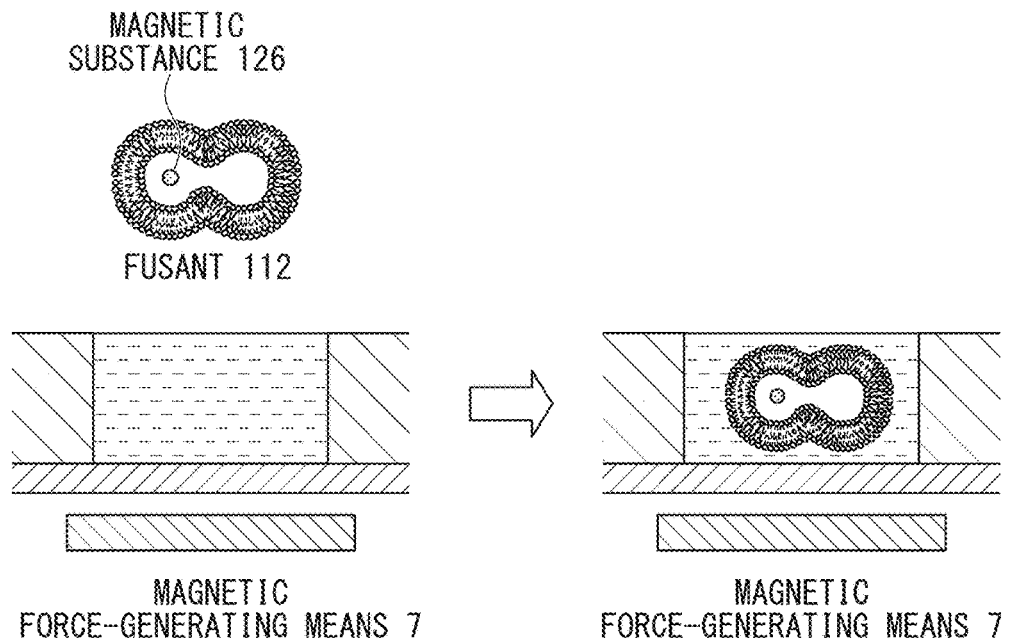
FIG. 17 is a view for illustrating a method of moving a vesicle according to an eighteenth embodiment.

FIG. 17 is a schematic view illustrating the method of moving a vesicle of the present embodiment. A solution containing the magnetic substance-containing artificial vesicle 127 is mixed with a sample solution containing the extracellular vesicle 110 such that the magnetic substance-containing artificial vesicle 127 and the extracellular vesicle 110 contact each other, thereby obtaining the fusant 112. A field to which the fusant 112 is to be moved is a recess portion provided on a substrate.

In the recess portion, magnetic force-generating means (magnetic force-generating member or a magnetic force-generating device) 7 is disposed. Then, by using the magnetic force-generating means 7, the fusant 112 containing the magnetic substance 126 is attracted. The magnetic force-generating means 7 is, for example, a permanent magnet or an electromagnet. By the magnetic force-generating means 7, the behavior of the artificial vesicle can be controlled, and the artificial vesicle can be moved and separated to an arbitrary field from the sample solution containing the extracellular vesicle 110.

Nineteenth Embodiment

Although the magnetic force-generating means 7 is used in the eighteenth embodiment, in the nineteenth embodiment of the present invention, the electrophoretic force-generating means (electrophoresis device) 121 can be used instead of the magnetic force-generating means 7.

Figure 18:
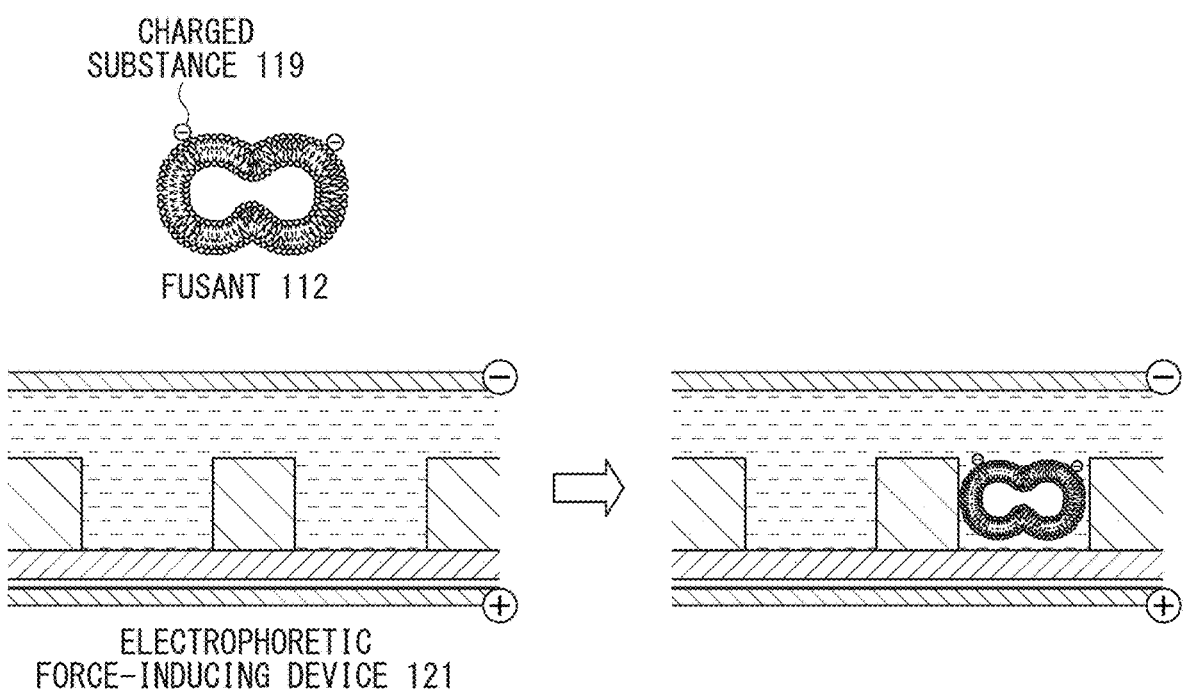
FIG. 18 is a view for illustrating a method of moving a vesicle according to a nineteenth embodiment.

FIG. 18 is a schematic view illustrating the method of moving a vesicle of the present embodiment. The artificial vesicle is modified with the charged substance 119. By the electrophoretic force-generating means 121, the behavior of the artificial vesicle can be controlled, and the artificial vesicle can be moved and separated to the recess portion provided on the substrate from a sample such as a solution containing the extracellular vesicle 110.

<<Method of Detecting Vesicle—II>>

The method of detecting a vesicle according to the twentieth to twenty-third embodiments of the present invention described herein is a method which is a combination of the method exemplified above in <<Method of detecting vesicle—I (fourteenth to seventeenth embodiments)>> and the <<Method of moving vesicle (eighteenth and nineteenth embodiments)>> described above. Herein, membrane fusion is not essential for causing a reaction between a reaction reagent and constituent of a vesicle.

Twentieth Embodiment

The method of detecting a vesicle according to the twentieth embodiment of the present invention is a method of detecting a vesicle using a method of moving a vesicle in which a vesicular-shaped lipid membrane structure, which contains a membrane-fusogenic lipid to be fused with a vesicle having a lipid bilayer membrane and a characteristic-imparting substance, is brought into contact with the vesicle such that membrane fusion occurs between the lipid membrane structure and the vesicle, and by using characteristics imparted or changed by the characteristic-imparting substance contained in the fusant 112 generated by the membrane fusion between the lipid membrane structure and the vesicle, the fusant 112 is attracted to a predetermined field. The fusant 112 is detected in the predetermined field.

The reaction reagent 6 may be disposed in the predetermined field. It is possible to exemplify an aspect in which the predetermined field is a recess portion formed on a substrate, and reaction reagent 6 is contained in the recess portion.

Figure 19:
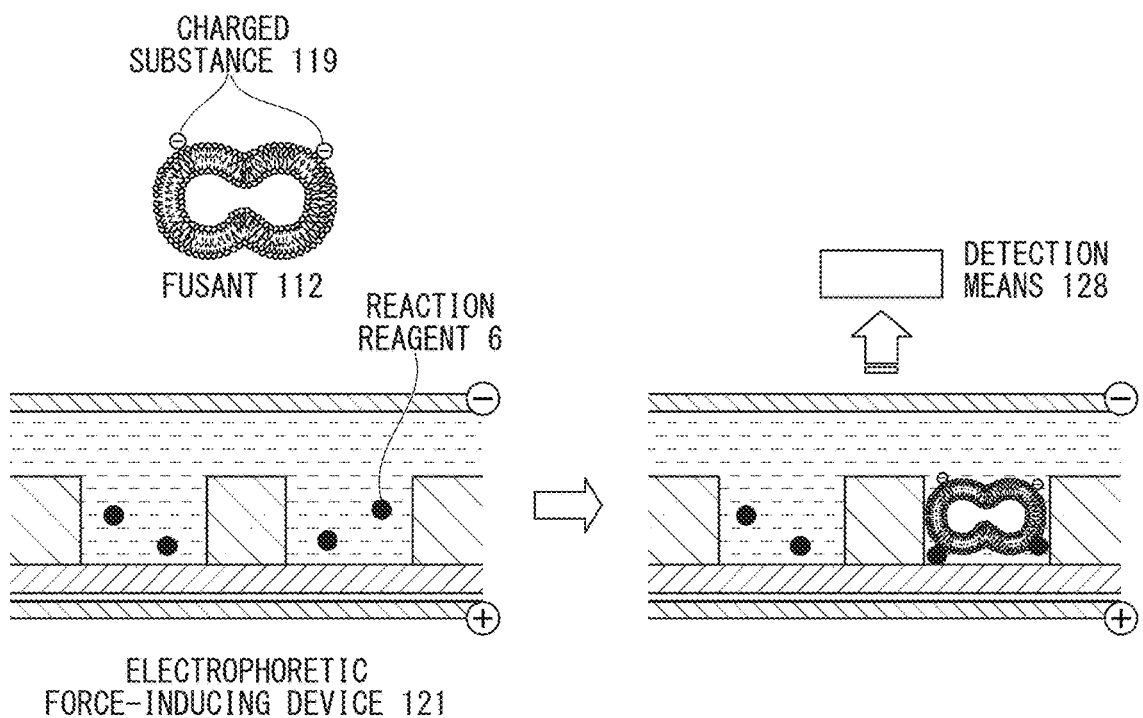
FIG. 19 is a view for illustrating a method of detecting a vesicle according to a twentieth embodiment.

FIG. 19 is a schematic view illustrating the method of detecting a vesicle of the present embodiment. A solution containing the charged substance-modified artificial vesicle 120 is mixed with a sample solution containing the extracellular vesicle 110 such that the charged substance-modified artificial vesicle 120 and the extracellular vesicle 110 contact each other, thereby obtaining the fusant 112. The field to which the fusant 112 is to be moved is the recess portion provided on the substrate. The electrophoretic force-generating means (electrophoresis device) 121 is disposed in the recess portion, and the recess portion contains the reaction reagent 6. Then, by using the electrophoretic force-generating means 121, the fusant 112 modified with the charged substance 119 is attracted.

A reaction is caused between the reaction reagent 6 and the constituent of the vesicle, and the reaction or a reaction product generated by the reaction is detected. In the present embodiment, examples of the constituent of the vesicle reacting with the reaction reagent 6 include a membrane protein of the extracellular vesicle 110.

The reaction reagent 6 may be contained in the lipid membrane structure 1 according to the first embodiment.

Figure 20:
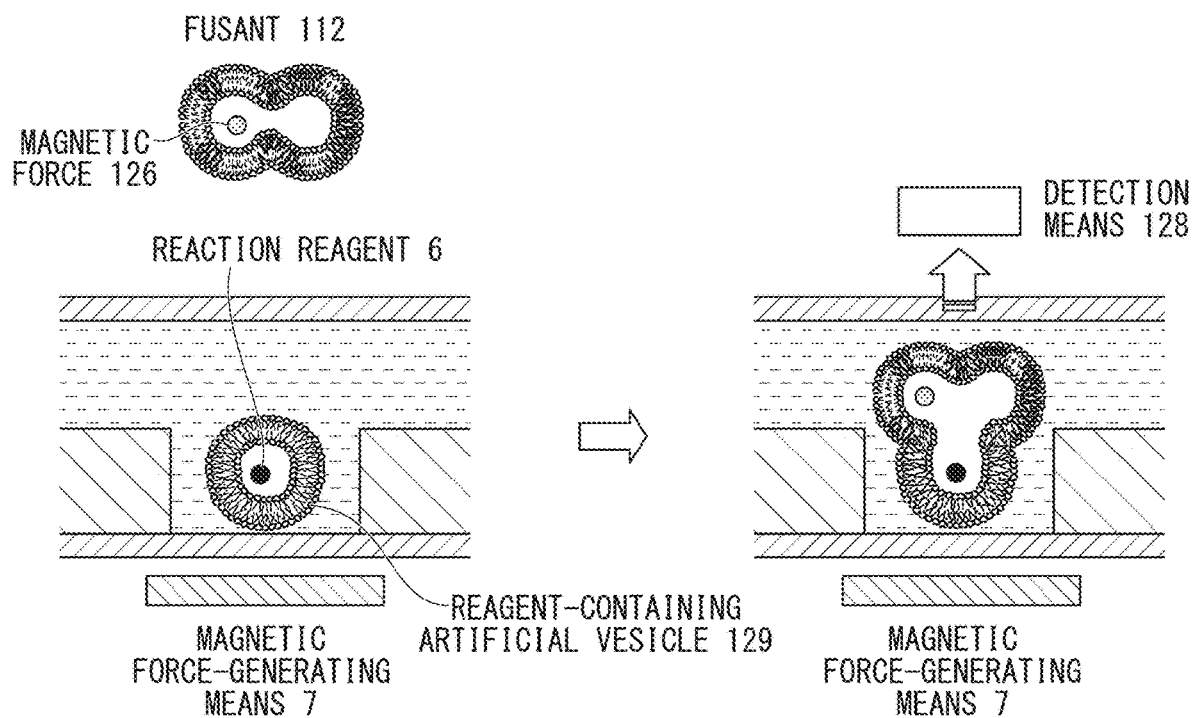
FIG. 20 is a view for illustrating a modification example of the method of detecting a vesicle according to the twentieth embodiment.

FIG. 20 is a schematic view illustrating a modification example of the method of detecting a vesicle of the twentieth embodiment. A solution containing the magnetic substance-containing artificial vesicle 127 is mixed with a sample solution containing the extracellular vesicle 110 such that the magnetic substance-containing artificial vesicle 127 and the extracellular vesicle 110 contact each other, thereby obtaining the fusant 112. The field to which the fusant 112 is to be moved is a recess portion provided on a substrate. The magnetic force-generating means 7 is disposed in the recess portion, and the recess portion contains the artificial vesicle 129 containing the reaction reagent 6. Then, by using the magnetic force-generating means (magnetic force-generating member or magnetic force-generating device) 7, the fusant 112 containing the magnetic substance 126 is attracted. The magnetic force-generating means 7 is, for example, a permanent magnet or an electromagnet. By fusing the fusant 112 with the artificial vesicle 129 on the substrate, a reaction is caused between the reaction reagent 6 and a constituent of the extracellular vesicle 110, and the reaction or a reaction product generated by the reaction is detected.

Twenty-First Embodiment

In the method of detecting a vesicle according to the twenty-first embodiment of the present invention, a membrane-fusogenic lipid to be fused with a vesicle having a lipid bilayer membrane is provided such that an opening portion of the recess portion, which is formed on the substrate in the twentieth embodiment, on a surface of the substrate is closed, and an artificial vesicle is fused with a lipid membrane structure on the substrate such that a reaction occurs between the reaction reagent and the constituent of the vesicle, and the reaction or a reaction product generated by the reaction is detected.

Figure 21:
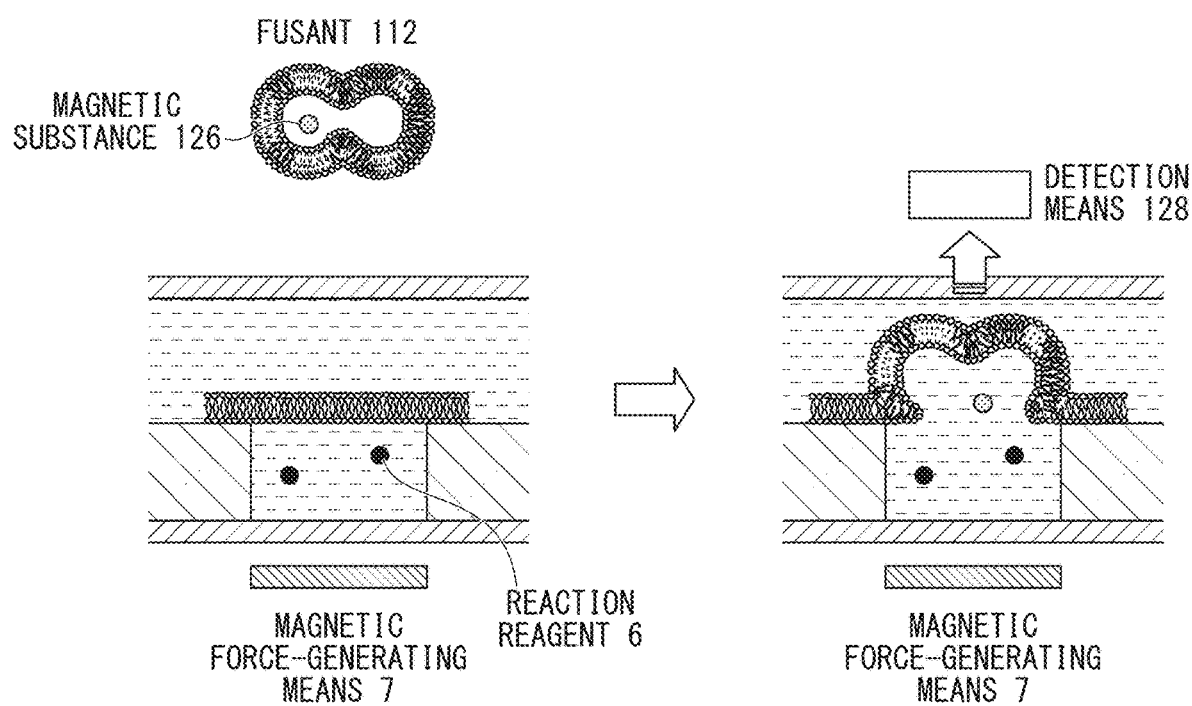
FIG. 21 is a view for illustrating a method of detecting a vesicle according to a twenty-first embodiment.

FIG. 21 is a schematic view illustrating the method of detecting a vesicle according to the twenty-first embodiment. A solution containing the magnetic substance-containing artificial vesicle 127 is mixed with a sample solution containing the extracellular vesicle 110 such that the magnetic substance-containing artificial vesicle 127 and the extracellular vesicle 110 contact each other, thereby obtaining the fusant 112. The field to which the fusant 112 is to be moved is a recess portion provided on the substrate. The magnetic force-generating means (magnetic force-generating member or magnetic force-generating device) 7 is disposed in the recess portion, and the recess portion contains the reaction reagent 6.

Then, by using the magnetic force-generating means 7, the fusant 112 containing the magnetic substance 126 is attracted. The magnetic force-generating means 7 is, for example, a permanent magnet or an electromagnet. A membrane-fusogenic lipid to be fused with a vesicle having a lipid bilayer membrane is provided such that an opening portion of the recess portion, which is formed on the substrate, on a surface of the substrate is closed, the artificial vesicle is fused with the lipid membrane structure on the substrate such that a reaction occurs between the reaction reagent 6 and a constituent of the vesicle, and the reaction or a reaction product generated by the reaction is detected.

Twenty-Second Embodiment

In the method of detecting a vesicle according to the twenty-second embodiment of the present invention, the aforementioned predetermined field is the lipid-membrane-structure-immobilization substrate 201 in which a vesicular-shaped lipid membrane structure, which contains a membrane-fusogenic lipid to be fused with a vesicle having a lipid bilayer membrane, is immobilized on a substrate, the aforementioned reaction reagent is contained in the lipid membrane structure, membrane fusion is caused between the fusant and the lipid membrane structure, a reaction is caused between the reaction reagent and a constituent of the vesicle by the membrane fusion between the fusant and the lipid membrane structure, and the reaction or a reaction product generated by the reaction is detected.

Figure 22:
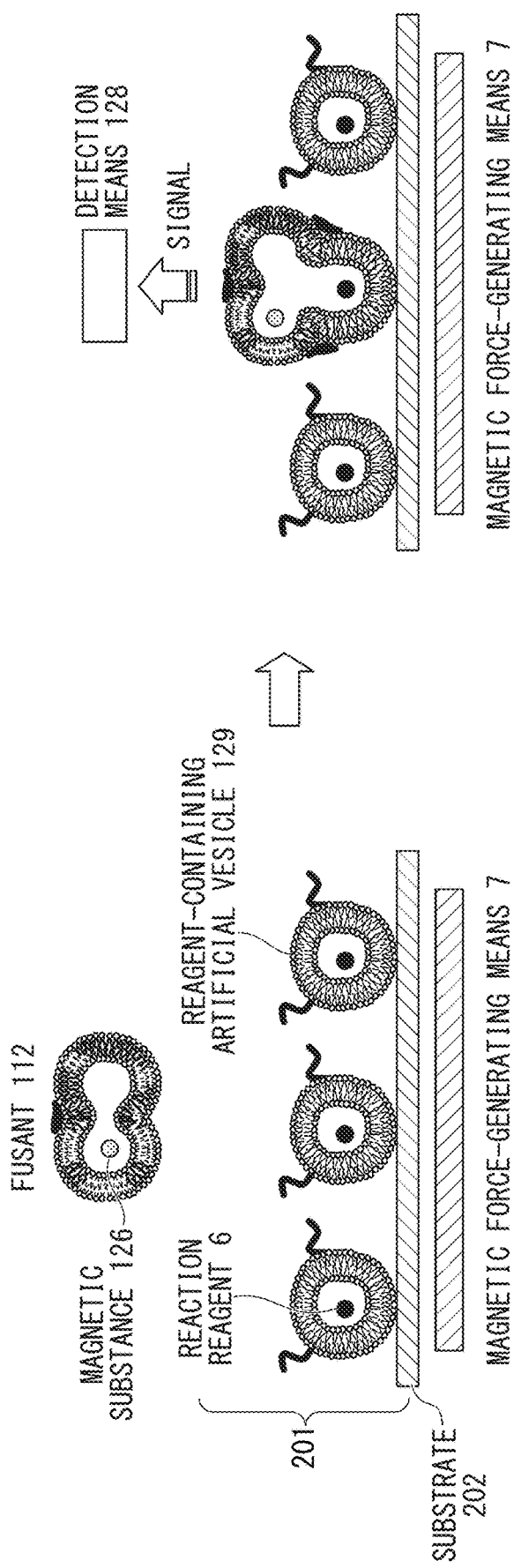
FIG. 22 is a view for illustrating a method of detecting a vesicle according to a twenty-second embodiment.

FIG. 22 is a schematic view illustrating the method of detecting a vesicle of the present embodiment. A solution containing the magnetic substance-containing artificial vesicle 127 is mixed with a sample solution containing the extracellular vesicle 110 such that the magnetic substance-containing artificial vesicle 127 and the extracellular vesicle 110 contact each other, thereby obtaining the fusant 112. The field to which the fusant 112 is to be moved is the artificial-vesicle-immobilization substrate 201 in which the artificial vesicle 127 is immobilized on a substrate. The magnetic force-generating means (magnetic force-generating member or magnetic force-generating device) 7 is disposed in the substrate, and the artificial vesicle 127 contains the reaction reagent 6. Then, by using the magnetic force-generating means 7, the fusant 112 containing the magnetic substance 126 is attracted. The magnetic force-generating means 7 is, for example, a permanent magnet or an electromagnet. By fusing the fusant 112 with the artificial vesicle 127 on the substrate, a reaction occurs between the reaction reagent 6 and a constituent of the extracellular vesicle 110, and the reaction or a reaction product generated by the reaction is detected.

Twenty-Third Embodiment

The method of detecting a vesicle according to the twenty-third embodiment of the present invention is a method of detecting a vesicle using a method of moving a lipid membrane structure, in which a vesicular-shaped lipid membrane structure, which contains a membrane-fusogenic lipid to be fused with a vesicle having a lipid bilayer membrane, a characteristic-imparting substance, and a reaction reagent, is attracted to a predetermined field by using characteristics imparted or changed by the characteristic-imparting substance contained in the lipid membrane structure. The vesicle is disposed in the predetermined field, the lipid membrane structure and the vesicle are brought into contact with each other in the predetermined field such that membrane fusion occurs between the lipid membrane structure and the vesicle, a reaction is caused between the reaction reagent and a constituent of the vesicle by the membrane fusion between the lipid membrane structure and the vesicle, and the reaction or a reaction product generated by the reaction is detected.

Figure 23:
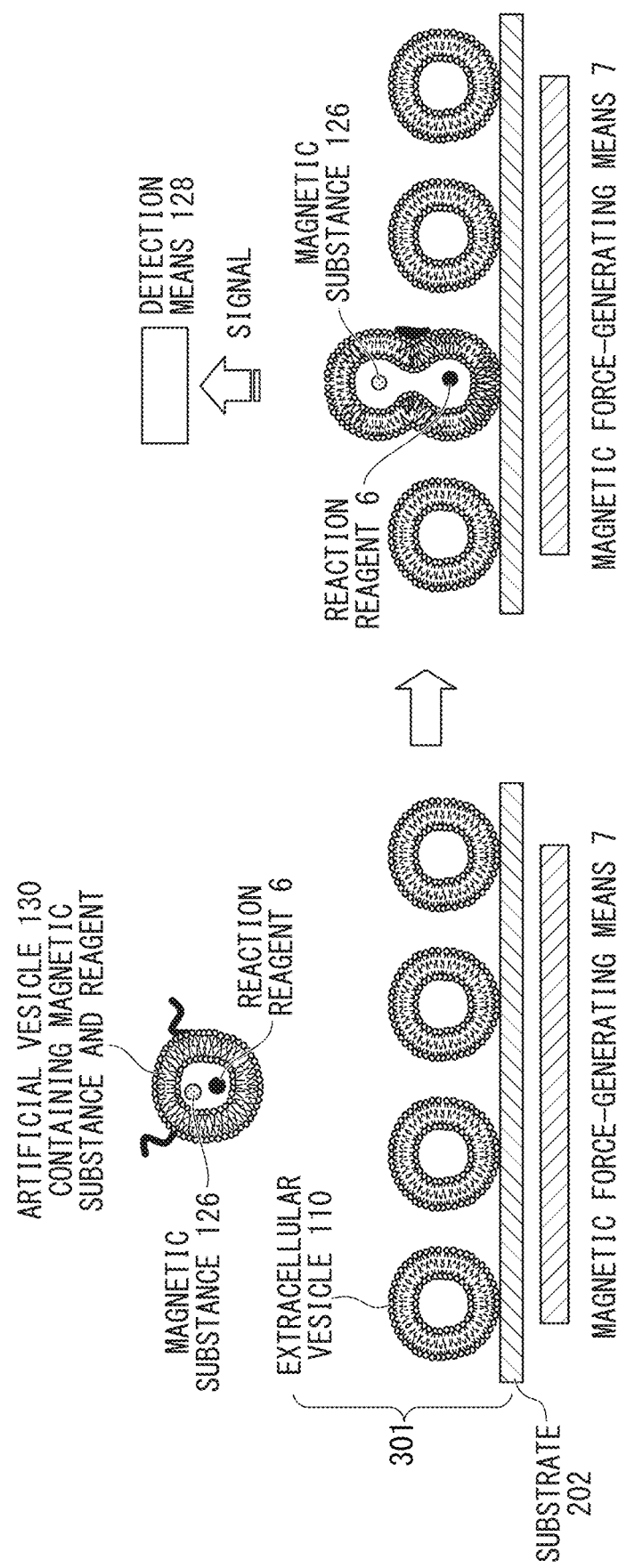
FIG. 23 is a view for illustrating a method of detecting a vesicle according to a twenty-third embodiment.

FIG. 23 is a schematic view illustrating the method of detecting a vesicle of the present embodiment. A solution containing the an artificial vesicle 130 which contains the magnetic substance 126 and the reaction reagent 6 is brought into contact with the extracellular-vesicle-immobilization substrate 301 in which the extracellular vesicle 110 is immobilized. The magnetic force-generating means (magnetic force-generating member or magnetic force-generating device) 7 is disposed in the substrate, and the artificial vesicle 130 containing the magnetic substance 126 is attracted to the substrate. Then, the artificial vesicle 130 and the extracellular vesicle 110 are brought into contact with each other such that they are fused, a reaction is caused between the reaction reagent 6 and a constituent of the extracellular vesicle 110, and the reaction or a reaction product generated by the reaction is detected.

The substrate on which the extracellular vesicle 110 is immobilized may be a substrate obtained by a conventionally known method, or a substrate obtained as a substrate, on which the vesicle (fusant) 112 derived from the extracellular vesicle 110 is immobilized, by using the method of separating a vesicle according to the eighth to thirteenth embodiments. As the substrate of the embodiments described above, it is possible to exemplify a vesicle immobilization substrate (fusant immobilization substrate) which is obtained by, as shown in the eight embodiment of <<Method of separating vesicle>>, bringing the artificial-vesicle-immobilization substrate, in which the artificial vesicle (lipid membrane structure) is immobilized on a substrate and a sample containing the extracellular vesicle (vesicle) 110 into contact with each other such that membrane fusion occurs between the lipid membrane structure and the vesicle.

As shown in the twentieth to twenty-third embodiments, by attracting the extracellular vesicle 110 or the fusant 112 to a predetermined field such as a recess portion formed on the substrate, it is possible to shorten the time taken for the step of detecting a signal generated by the reaction between the reaction reagent 6 disposed in the predetermined field and the extracellular vesicle or the fusant, and to improve the detection efficiency.

Furthermore, as shown in the twentieth to twenty-third embodiments, in a case where the lipid membrane structure of the present invention is disposed in the predetermined field, by attracting the extracellular vesicle 110 or the fusant 112 to the predetermined field such as a recess portion, it is possible to improve the efficiency of fusion between the extracellular vesicle or the fusant and a lipid membrane. In addition, it is possible to shorten the time taken for the step of detecting a signal generated by the reaction between the reaction reagent 6 disposed in the predetermined field and the extracellular vesicle or the fusant, and to improve the detection efficiency.

<<Method of Evaluating Vesicle>>

The method of evaluating a vesicle according to the twenty-fourth to twenty-seventh embodiments of the present invention will be described below.

The vesicle and the subject vesicle in the present embodiment have a lipid bilayer membrane.

Examples of the lipid constituting the lipid bilayer membrane include a phospholipid, a glycolipid, a sterol, a saturated or unsaturated fatty acid, and the like.

Examples of the phospholipid include phosphatidylcholine such as dioleoylphosphatidylcholine, dipalmitoylphosphatidylcholine, or dilauroylphosphatidylcholine; phosphatidylglycerol such as dioleoylphosphatidylglycerol, dipalmitoylphosphatidylglycerol, or dilauroylphosphatidylglycerol; phosphatidylethanolamine such as dioleoylphosphatidylethanolamine, dipalmitoylphosphatidylethanolamine, or dilauroylphosphatidylethanolamine; phosphatidylserine such as dioleoylphosphatidylserine, dipalmitoylphosphatidylserine, or dilauroylphosphatidylserine; phosphatidic acid, phosphatidylinositol, cardiolipin, sphingomyelin, egg yolk lecithin, soybean lecithin, the above phospholipids that are hydrogenated, and the like.

Examples of the glycolipid include glyceroglycolipid such as sulfoxyribosyl glyceride, diglycosyl diglyceride, or digalactosyl diglyceride; sphyngoglycolipid such as galactosyl cerebroside, lactosyl cerebroside, or ganglioside; and the like.

Examples of the sterol include animal-derived sterol such as cholesterol, cholesterol succinate, or lanosterol; a plant-derived sterol such as stigmasterol, sitosterol, or campesterol; and a microorganism-derived sterol such as zymosterol or ergosterol.

Examples of the saturated or unsaturated fatty acid include a saturated or unsaturated fatty acid having 12 to 20 carbon atoms, such as palmitic acid, oleic acid, or stearic acid.

The lipid membrane may contain any substance in addition to the lipid forming the lipid membrane, as long as the formation of the lipid membrane is not hindered. Examples of such a substance include a membrane stabilizer, a charged substance, a membrane protein, and the like. If the lipid membrane contains these substances, the membrane stability can be improved, or the charge of the membrane can be controlled.

Examples of the membrane stabilizer include a sterol, a glycerin, a fatty acid ester thereof, and the like.

Specific examples of the sterol are the same as described above. Examples of the fatty acid ester of glycerin include triolein, trioctanoin, and the like.

Examples of the charged substance that imparts a positive charge include a saturated or unsaturated aliphatic amine such as stearylamine or oleylamine; a saturated or unsaturated cationic synthetic lipid such as dioleoyl trimethylammonium propane; and the like.

Examples of the charged substance that imparts a negative charge include phosphatidic acid, phosphatidylserine, and phosphatidylinositol.

Examples of the membrane protein include a peripheral membrane protein, integral membrane protein, and the like.

The vesicle or the subject vesicle having a lipid bilayer membrane has the shape of a vesicle formed of a lipid bilayer membrane, and may be an artificially made vesicle or a natural vesicle. Examples of the natural vesicle include a cell having a lipid bilayer membrane, a unicellular organism, a microorganism, a fungus, a bacterium, a virus, an organelle, a vacuole, a membrane vesicle, a vesicle, a transport vesicle, an aggregate of these, and the like. Examples of the artificially made vesicle having a lipid bilayer membrane include a liposome, a vesicle obtained by pulverizing a natural vesicle and making again a vesicular-shaped vesicle, and the like. The vesicle having a lipid bilayer membrane may be a vesicle derived from a microsome having a lipid bilayer membrane.

As a sample containing the subject vesicle or the vesicle, for example, it is possible to use any sample such as a bio-derived sample solution such as blood, serum or urine, a solution prepared from these, or a buffer.

A carrier 108 to be used is at least one of a substrate, a film, a magnetic bead, a silica bead, a glass bead, and a polymer, and a first substance 107 should be immobilized on a surface of the carrier.

Twenty-Fourth Embodiment

Figure 26:
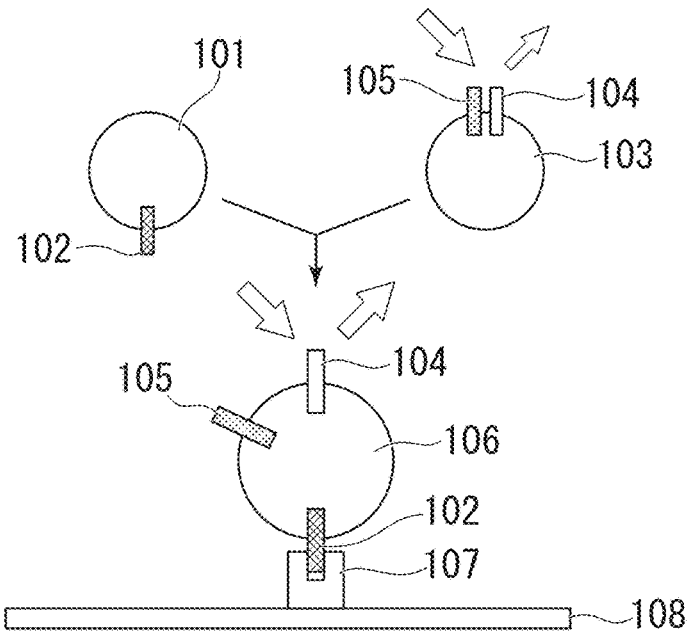
FIG. 26 is a view for illustrating a twenty-fourth embodiment of the present invention.
Figure 27:
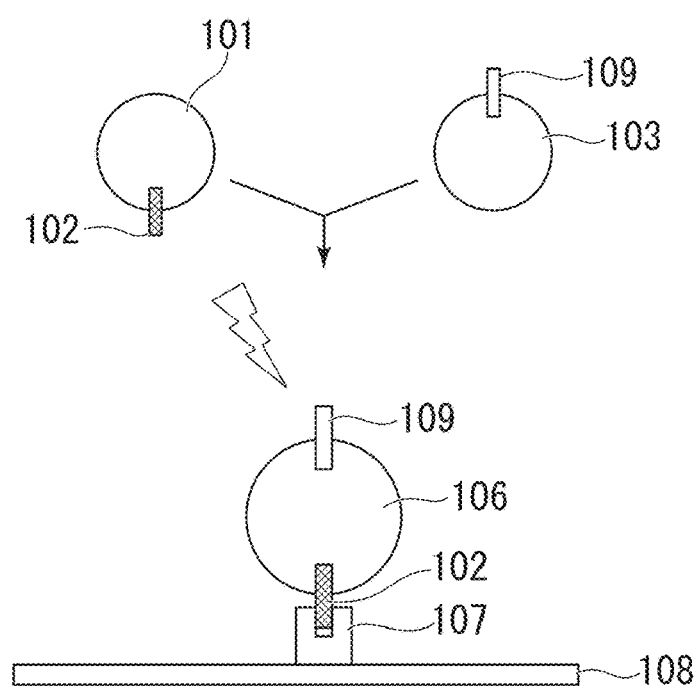
FIG. 27 is a view for illustrating a twenty-fifth embodiment of the present invention.

A membrane fusion evaluation system according to the twenty-fourth embodiment of the present invention will be described. FIG. 26 is a schematic view of the membrane fusion evaluation system according to the present embodiment.

In the twenty-fourth embodiment, the carrier 108 is a substrate, and the vesicle 103 is a lipid bilayer membrane having a first fluorescent substance 104 and a second fluorescent substance 105. A fluorescence wavelength of the first fluorescent substance 104 is close to an excitation wavelength of the second fluorescent substance 105. The subject vesicle 101 is a vesicle with a lipid bilayer membrane containing an immobilization substance 102. The subject vesicle 101 and the vesicle 103 may contain a membrane-fusogenic lipid.

After the complex 106 being formed, the complex 106 is immobilized on the carrier 108 due to the bonding between the immobilization substance 102 and a first substance 107. Due to the mixing of lipids, the first fluorescent substance 104 and the second fluorescent substance 105 become distant from each other in the complex 106, and hence the fluorescence wavelength of the first fluorescent substance 104 increases. Therefore, a fact that the subject vesicle 101 and the vesicle 103 are fused with each other can be evaluated.

As the first substance 107, at least one substance, which is selected from the group consisting of an antibody, an antibody fragment, a complete antigen, and a hapten according to the subject substance, is adopted. It is preferable that the first substance 107 exhibit high specificity with respect to the immobilization substance 102. For example, the first substance 107 is easily bonded to the immobilization substance 102 in a sample but is not easily bonded substances other than the immobilization substance 102.

It is also possible to recover a complex by breaking the bond between the immobilization substance 102 and the first substance 107.

Any substance can be used as the first fluorescent substance 104 and the second fluorescent substance 105 as long as the substance is a combination of a donor molecule and an acceptor molecule causing Fluorescence resonance energy transfer (FRET). Specifically, examples thereof include a mixture of 3,3'-dioctadecyloxycarbocyanine perchlorate (hereinafter, abbreviated to DiO) and octadecyl rhodamine B chloride (hereinafter, abbreviated to rhodamine), a mixture of 4,4-difluoro-5-octyl-4-bora-3a,4a-diaza-s-indacene-3-pentanoic acid (hereinafter, abbreviated to C8-BODIPY (R) 500/51005) and rhodamine, a mixture of nitrobenzoxadiazole (7-nitrobenz-2-oxa-1,3-diazol-4-yl) (hereinafter, abbreviated to NBD) and rhodamine B chloride, and the like. When membrane fusion occurs, fluorescent molecules of these fluorescent substances that label the membrane are diffused and diluted, and the donor molecules and the acceptor molecules become distant from each other. Accordingly, the fluorescence intensity of the donor molecules increases. The combination of the fluorescent substances in the present embodiment is not limited to the above examples.

Twenty-Fifth Embodiment

In the twenty-fifth embodiment of the present invention, detection is performed using a substance reacting with a second substance 109 in the complex 106. Examples of the substance reacting with the second substance 109 include a matrix, a chemiluminescent substance, an oxidation-reduction substance, and the like. In the present embodiment, by detecting a signal generated by the reaction between the second substance 109 and the aforementioned substance, only the complex 106 formed of the subject vesicle 101 and the vesicle 103 can be detected and evaluated. Furthermore, detection may be performed using a substance which is immobilized on the carrier 108 through the second substance 109 in the complex 106 and reacts with the immobilization substance 102.

The detection substance is at least one labeling substance selected from the group consisting of a colorimetric substance, a fluorescent substance, an oxidation-reduction substance, a nucleic acid, and an enzyme. Examples of the luminescent substance include a fluorescent molecule, a phosphorescent molecule, a chemiluminescent molecule, an enzyme conjugate molecule, and the like. Examples of the detection method at the time of using a nucleic acid as a labeling substance include a nucleic acid detection method such as immuno PCR, an Invader method, a Taqman method, or a fluorescent probe method.

Twenty-Sixth Embodiment

In the twenty-sixth embodiment of the present invention, instead of the aforementioned method in which detection and evaluation are performed by forming the complex 106 of the subject vesicle 101 and the vesicle 103 and then immobilizing the complex 106 on the carrier 108, a method can be used in which the complex 106 is formed after the subject vesicle 101 or the vesicle 103 is immobilized on the carrier 108 in advance and then detection and evaluation are performed.

Twenty-Seventh Embodiment

In the twenty-seventh embodiment of the present invention, detection and evaluation can be performed by using a color change resulting from a reaction which is caused in the vesicle by the fusion between the subject vesicle 101 containing an enzyme and the vesicle 103 containing a matrix.

Furthermore, detection and evaluation may be performed by using a color change resulting from a reaction which is caused in the vesicle by the fusion between the subject vesicle 101 containing a matrix and the vesicle 103 containing an enzyme.

EXAMPLES

Hereinafter, the present invention will be more specifically explained by describing examples, but the present invention is not limited to the following examples.

[Example 1] Membrane Fusion of Artificial Vesicles Induced by Addition of Membrane Fusion Inducer As a membrane fusion model, a membrane fusion experiment was performed using dioleoylphosphatidylcholine (DOPC) liposomes (particle size: 100 nm, Fourmular Scientific) as artificial vesicles and polyethylene glycol (PEG) (molecular weight: 6,000, Wako Pure Chemical Industries, Ltd.) as a membrane fusion inducer (additive).

Figure 24A:
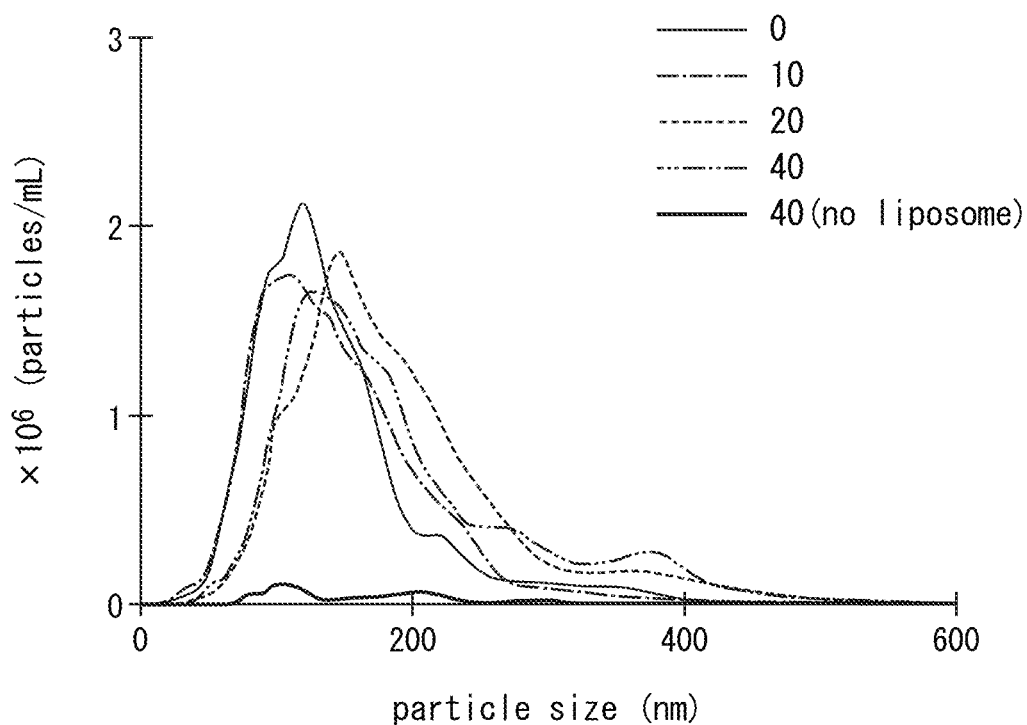
FIG. 24A is a graph showing particle sizes of liposomes measured after membrane fusion is caused between liposomes in Example 1.
Figure 24B:
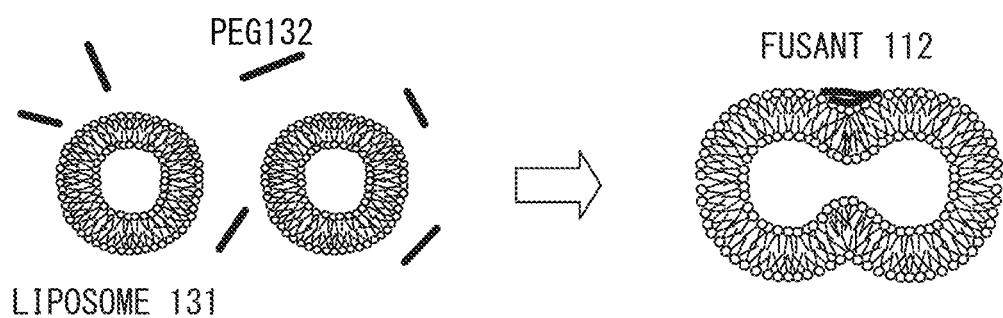
FIG. 24B is a view schematically showing the way the membrane fusion occurs between liposomes in Example 1.

PEG solutions at different concentrations (0, 10, 20, and 40 wt %) were added to a 100 μg/mL DOPC liposome solution, followed by stirring for 20 minutes, thereby causing membrane fusion of liposomes. For evaluating the membrane fusion, by using a nanoparticle size analyzer (NanoSight NS-500, Quantum Design Japan), the particle size of the DOPC liposomes after the addition of the PEG solutions at different concentrations was measured. The results are shown in FIG. 24A. FIG. 24B is a view schematically showing the way the membrane fusion of the artificial vesicles occurs in the present embodiment. It was confirmed that unlike an average particle size (153.01 nm) of the liposomes at a PEG concentration of 0 wt %, an average particle size of the liposomes to which PEG was added increased depending on the concentration of the added PEG after the addition of PEG and stirring.

[Example 2] Membrane Fusion of Fluorescence-Containing Artificial Vesicle Induced by Membrane Fusion Inducer Membrane fusion was tested using NDB-containing liposomes (molar ratio, DOPC:CHOL:NBD=54:45:1) and Rhodamine-containing liposomes (molar ratio, DOPC:CHOL:Rhodamine=54:45:1) (particle size: 100 nm, Fourmular Scientific) as fluorescence-containing vesicles and polyethylene glycol (PEG) (molecular weight: 6,000, Wako Pure Chemical Industries, Ltd.) as a membrane fusion inducer (additive).

Figure 25A:
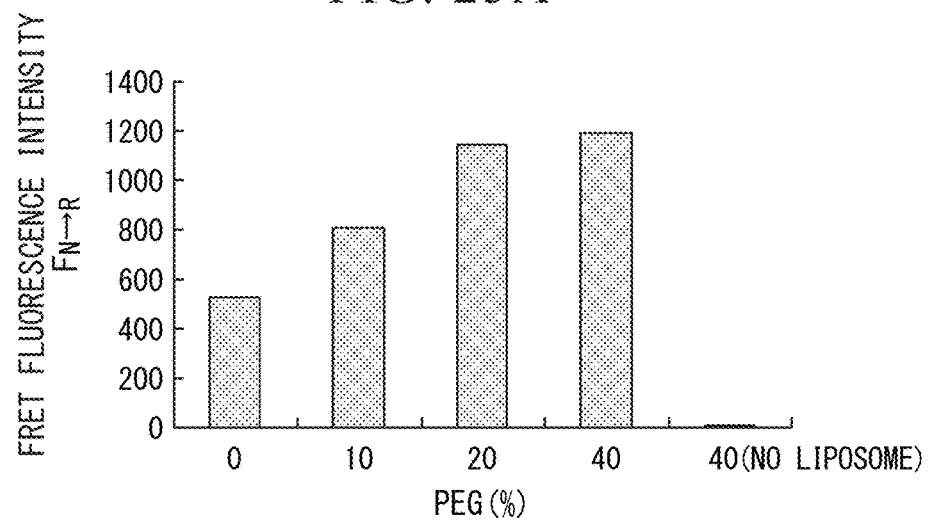
FIG. 25A is a graph showing fluorescence intensity measured after membrane fusion is caused between fluorescence-containing liposomes in Example 2.
Figure 25B:
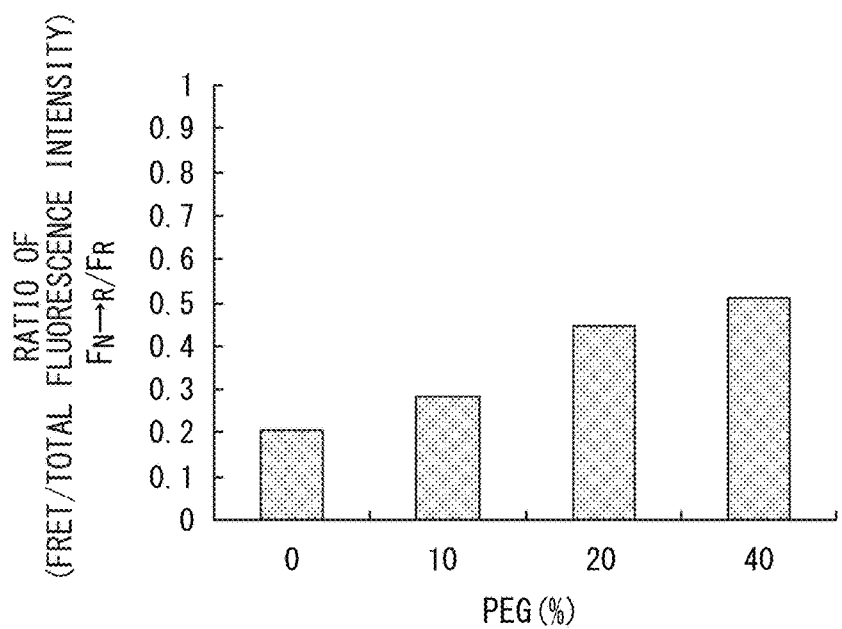
FIG. 25B is a graph showing fluorescence intensity measured after membrane fusion is caused between fluorescence-containing liposomes in Example 2.
Figure 25C:
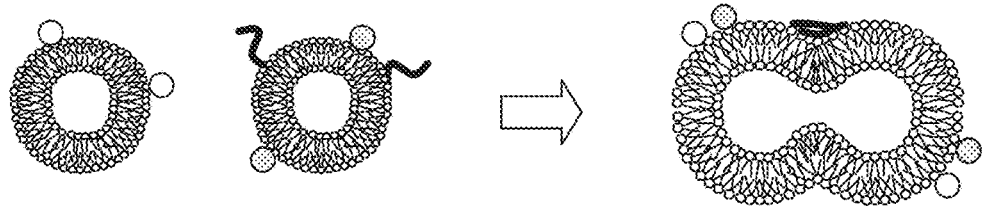
FIG. 25C is a view schematically showing the way the membrane fusion occurs between liposomes in Example 2.

PEG solutions at different concentrations (0, 10, 20, and 40 wt %) were added to a 100 μg/mL DOPC liposome solution, followed by stirring for 20 minutes, thereby causing membrane fusion of liposomes. For evaluating the membrane fusion, by using a fluorescent plate reader (Infinite M200, TECAN), FRET fluorescence intensity of the liposomes after the addition of the PEG solutions at different concentrations was measured. The results are shown in FIGS. 25A and 25B. FIG. 25C is a view schematically showing the way the membrane fusion occurs between fluorescence-containing artificial vesicles in the present example. It was confirmed that unlike a FRET fluorescence intensity at a PEG concentration of 0 wt %, a FRET fluorescence intensity of the liposomes increased depending on the concentration of added PEG after the addition of PEG and stirring.

From the above results, it was confirmed that membrane fusion occurred between liposomes. The membrane fusion between the liposomes was accelerated depending on the concentration of added PEG as a membrane fusion-inducer (additive). Furthermore, by the measurement of FRET fluorescence intensity, it was confirmed that a fusant of liposomes was formed, and the existence of the fusant could be detected.

Example 3

<Evaluation of Fusion Between Biotin-Modified Liposome and Fluorescence-Labeled Liposome>

In the present embodiment, by using a biotin-modified liposome and a fluorescence-labeled liposome as vesicles, an experiment for evaluating membrane fusion was performed. As a first substance, avidin recognizing biotin was used by being immobilized on a substrate. As a second substance, a fluorescent substance rhodamine was used.

<Preparation of Fluorescence-Labeled Liposome>

In a glass test tube, 1,2-dioleoyl-sn-glycero-3-phospho-L-serine (hereinafter, abbreviated to DOPS, manufactured by NOF CORPORATION) and Rhodamine-Phosphatidylethanolamine (hereinafter, abbreviated to Rhodamine-PE) (manufactured by Avanti Polar Lipids, Inc.) were dissolved in chloroform such that a molar ratio thereof became 100:1, thereby preparing a 10 mg/mL DOPS•Rhodamine-PE chloroform solution. The DOPS•Rhodamine-PE chloroform solution was dried under reduced pressure by using a desiccator such that the organic solvent was removed, thereby preparing a lipid thin membrane. The lipid thin membrane was mixed with 1 mL of a 25 mM MES 125 mM NaCl pH=7.4 buffer (hereinafter, abbreviated to MES buffer), and the mixture was treated with ultrasonic waves for approximately 1 minute by using a bath-type sonicator, thereby preparing fluorescence-labeled liposomes.

In order to adjust the size of the fluorescence-labeled liposomes, the liposomes were passed through a filter of Nuclepore polymembrane carbonate (manufactured by Whatman plc) having a pore size of 100 nm, thereby preparing uniform fluorescence-labeled liposomes.

<Preparation of Biotin-Modified Liposome>

DOPS (manufactured by NOF CORPORATION) and 1,2-dioleoyl-sn-glycero-3-phosphoethanolamine-N-(cap biotinyl) (hereinafter, abbreviated to DOPE-biotin, manufactured by Avanti Polar Lipids, Inc.) were dissolved in chloroform such that a molar ratio thereof became 100:1, thereby preparing a 10 mg/mL DOPS•DOPE-biotin chloroform solution. The DOPS•DOPE-biotin chloroform solution was dried under reduced pressure by using a desiccator such that the organic solvent was removed, thereby preparing a lipid thin membrane. The lipid thin membrane was mixed with 1 mL of the MES buffer, and the mixture was treated with ultrasonic waves for approximately 1 minute by using a bath-type sonicator, thereby preparing biotin-modified liposomes.

In order to adjust the size of the biotin-modified liposomes, the liposomes were passed through a filter of Nuclepore polymembrane carbonate (manufactured by Whatman plc) having a pore size of 100 nm, thereby preparing uniform biotin-modified liposomes.

<Preparation of Dichroic Fluorescence-Labeled Liposome>

In a glass test tube, DOPS, Rhodamine-PE, and NBD-Phosphatidylethanolamine (hereinafter, abbreviated to NBD-PE, manufactured by Avanti Polar Lipids, Inc.) were dissolved in chloroform such that a molar ratio thereof became 100:1:0.5, thereby preparing a 10 mg/mL DOPS•Rhodamine-PE•NBD-PE chloroform solution. The DOPS•Rhodamine-PE•NBD-PE chloroform solution was dried under reduced pressure by using a desiccator such that the organic solvent was removed, thereby preparing a lipid thin membrane. The lipid thin membrane was mixed with 1 mL of a 25 mM MES 125 mM NaCl pH=7.4 buffer (hereinafter, abbreviated to MES buffer), and the mixture was treated with ultrasonic waves for approximately 1 minute by using a bath-type sonicator, thereby preparing dichroic fluorescence-labeled liposomes.

In order to adjust the size of the dichroic fluorescence-labeled liposomes, the liposomes were passed through a filter of NUCLEPORE® polymembrane carbonate (manufactured by Whatman plc) having a pore size of 100 nm, thereby preparing uniform dichroic fluorescence-labeled liposomes.

Reference Example 1

In Reference example 1, detection was performed using the biotin-modified liposomes (DOPS/biotin), the fluorescence-labeled liposomes (DOPS/rhodamine), and a 96-well plate.

A solution obtained by mixing 10 μL of the biotin-modified liposomes (10 mg/mL) with 190 μL of a MES buffer and a solution obtained by mixing 10 μL of the fluorescence-labeled liposomes (10 mg/mL) with 190 μL of a MES buffer were incubated for 1 hour at 37° C. Then, 100 μL of a liposome solution (lipid concentration: 62.5 μg/mL) caused to react with a Streptavidin Coated Plates (HBC) Black 96-well with SUPERBLOCK® Blocking Buffer (manufactured by Thermo Fisher Scientific Inc.) washed 3 times with 300 μL of PBS was added thereto, followed by incubation for 5 hours at 25° C.

Figure 28:
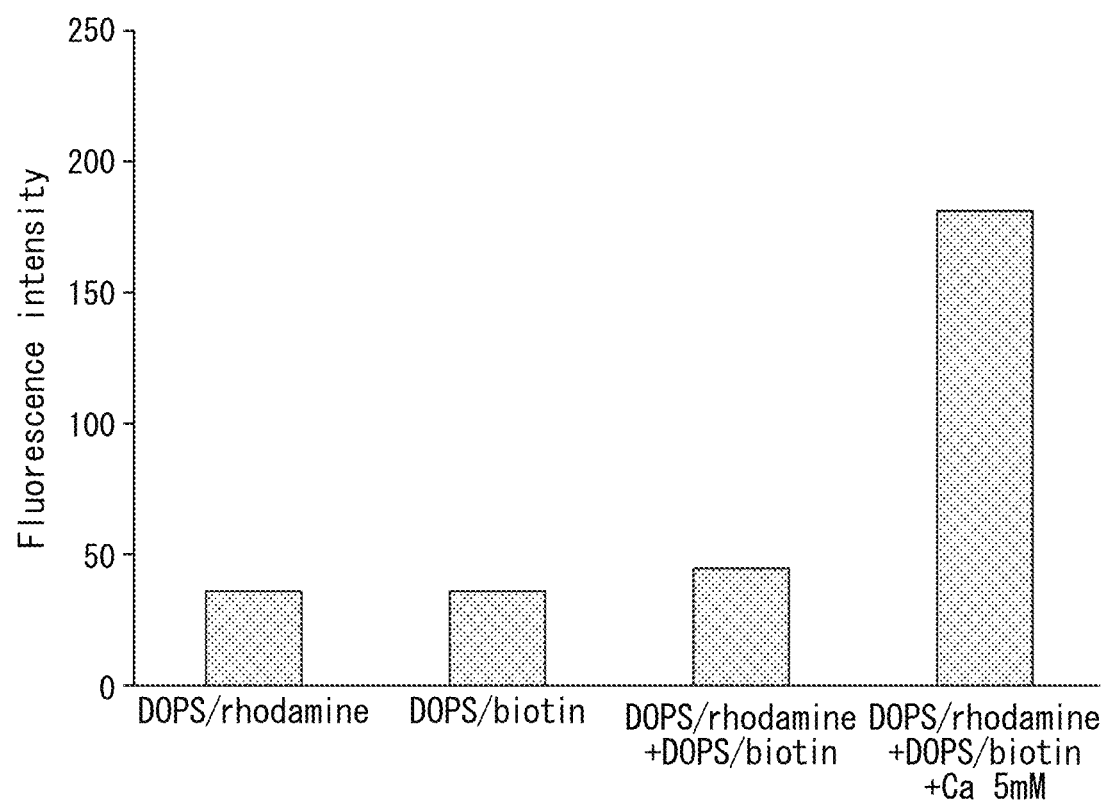
FIG. 28 is a view for showing the results of Reference example 1 and Example 4.

The resultant was washed 3 times with 300 μL of PBS, and then the fluorescence intensity of rhodamine (excitation wavelength: 560 nm, fluorescence wavelength: 580 nm) was measured using a plate reader (Infinite M200, manufactured by TECAN). The results are shown in FIG. 28.

Example 4

In Example 4, a mixed solution of the biotin-modified liposomes and the fluorescence-labeled liposomes was prepared in the same manner as in Reference example 1, and fluorescent liposomes were detected using a 96-well plate.

A solution (DOPS/rhodamine+DOPS/biotin), which was obtained by mixing 10 μL of the biotin-modified liposomes (10 mg/mL), 10 μL of the fluorescence-labeled liposomes (10 mg/mL), and 180 μL of a MES buffer together, and a solution (DOPS/rhodamine+DOPS/biotin+Ca 5 mM), which was obtained by mixing 10 μL of the biotin-modified liposomes (10 mg/mL), 10 μL of the fluorescence-labeled liposomes (10 mg/mL), a MES buffer, and 180 μL of a $CaCl_2$ solution (final concentration: 5 mM) together, were incubated for 1 hour at 37° C. Then, 100 μL of a liposome solution (lipid concentration: 62.5 μg/mL) caused to react with a Streptavidin Coated Plates (HBC) Black 96-well with SUPERBLOCK® Blocking Buffer washed 3 times with 300 μL of PBS was added thereto, followed by incubation for 5 hours at 25° C.

The resultant was washed 3 times with 300 μL of PBS, and the fluorescence intensity of rhodamine was measured using a plate reader. The results are shown in FIG. 28.

FIG. 28 shows the result obtained from the fluorescence-labeled liposomes (Reference example 1), the result obtained from the biotin-modified liposomes (Reference example 1), the result obtained from the "fluorescence-labeled liposomes+biotin-modified liposomes" (Example 4), and the result obtained from the sample (Example 4) prepared by adding 5 mM Ca to the "fluorescence-labeled liposomes+biotin-modified liposomes".

Herein, the ordinate shows the fluorescence intensity of rhodamine after washing.

As shown in FIG. 28, it was confirmed that the fluorescence intensity was different depending on whether or not fusion is caused by the addition of Ca. It was also confirmed that it was possible to evaluate the fusion of vesicles by using the biotin-modified liposomes and the fluorescence-labeled liposomes.

Example 5

<Preparation of DOPS Liposome>
In a glass test tube, DOPS (manufactured by NOF CORPORATION) was dissolved in chloroform, thereby preparing a 10 mg/mL DOPS chloroform solution. The DOPS chloroform solution was dried under reduced pressure by using a desiccator such that the organic solvent was removed, thereby preparing a lipid thin membrane. The lipid thin membrane was mixed with 1 mL of a MES buffer, and the mixture was treated with ultrasonic waves for approximately 1 minute by using a bath-type sonicator, thereby preparing DOPS liposomes.

In order to adjust the size of the DOPS liposomes, the liposomes were passed through a filter of Nuclepore polymembrane carbonate (manufactured by Whatman PLC) having a pore size of 100 nm, thereby preparing uniform DOPS liposomes.

<Testing Fusion by Ca Addition>
The following experiment was performed using the DOPS liposomes and the dichroic fluorescence-labeled liposome prepared by the method described Example 3.

A solution, which was obtained by mixing 2 μL of a mixed liquid of the DOPS liposomes (10 mg/mL) and the dichroic fluorescence-labeled liposomes (10 mg/mL) with 198 μL of a mixed liquid (final concentration: 0, 1, 3, and 5 mM) of a MES buffer and $CaCl_2$, was incubated for 1 hour at 37° C.

Figure 29:
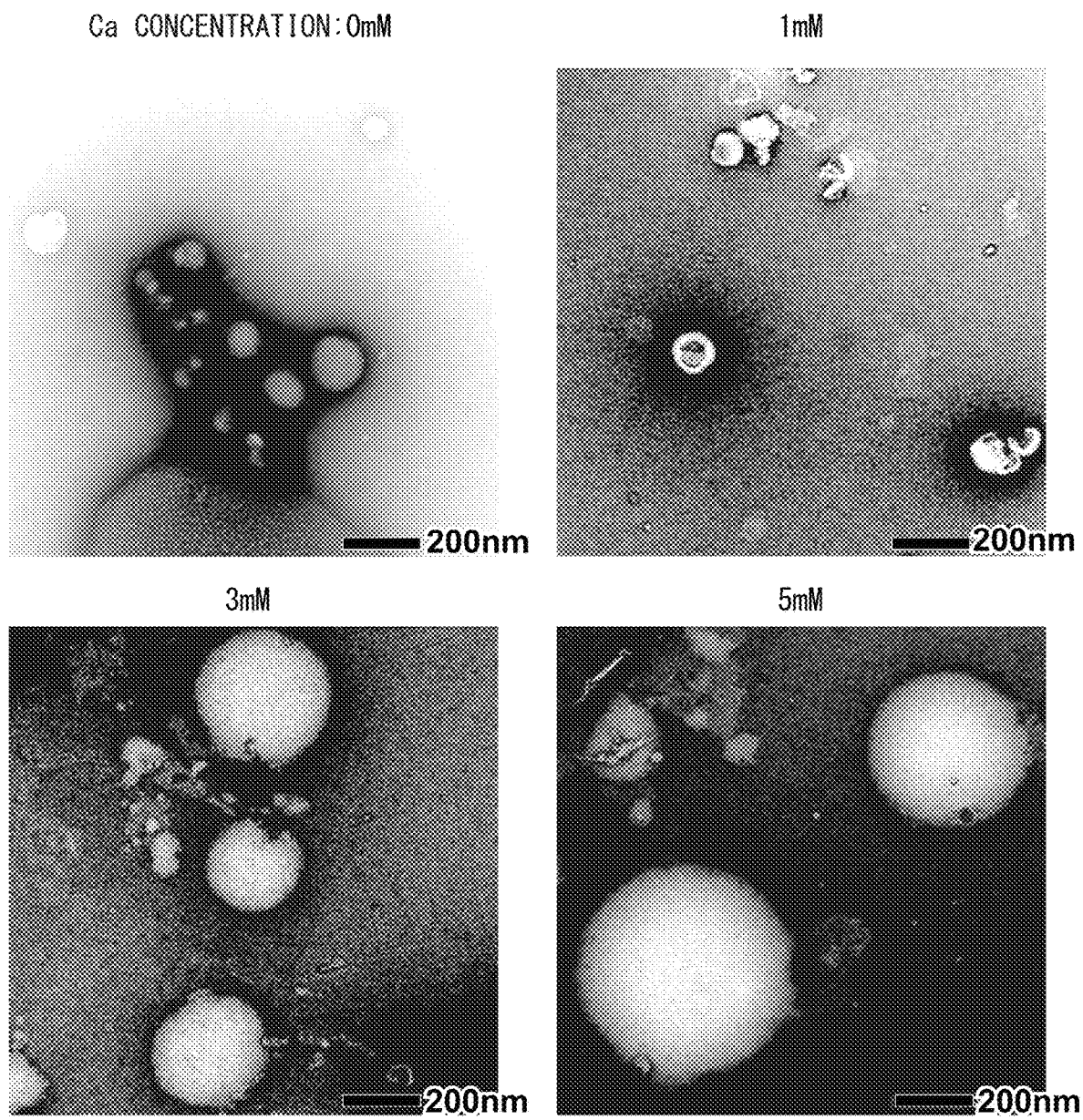
FIG. 29 shows TEM images in Example 5.

FIG. 29 shows TEM images obtained by observing fusants of the DOPS liposomes and the dichroic fluorescence-labeled liposomes that were formed in a case where the Ca concentration added to the mixed liquid of the DOPS liposomes and the dichroic fluorescence-labeled liposomes was changed to 0 mM, 1 mM, 3 mM, and 5 mM.

As shown in FIG. 29, by using TEM, it was possible to confirm that the particle size of the fusants markedly increased when the Ca concentration was equal to or higher than 3 mM.

Figure 30:
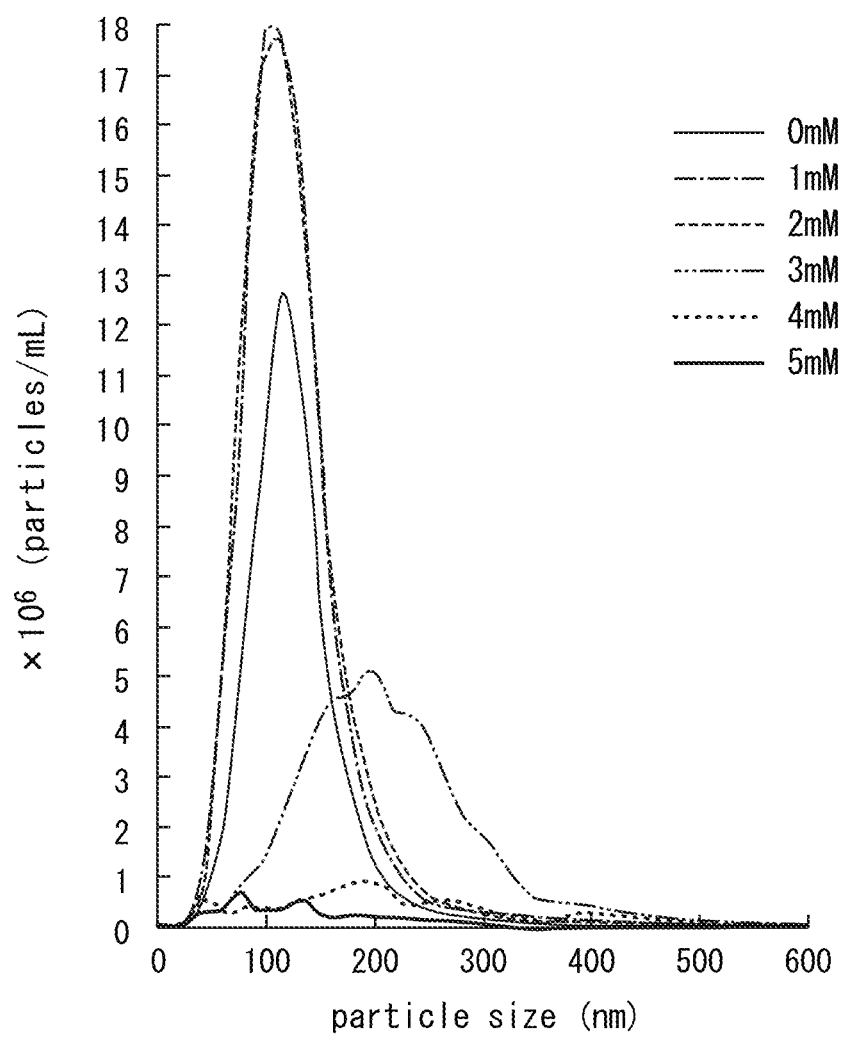
FIG. 30 shows the results of particle size distribution analysis in Example 5.

FIG. 30 shows the results of particle size distribution analysis on the fusants that were obtained in a case where the Ca concentration was changed within a range of 0 to 5 mM. For the particle size distribution analysis, a nanoparticle size analyzer (NanoSight NS-500, Quantum Design Japan) was used.

As shown in FIG. 30, it was confirmed that when the Ca concentration was equal to or higher than 3 mM, the average particle size of the fusants increased, and the number of particles resulting from the membrane fusion decreased.

Figure 31:
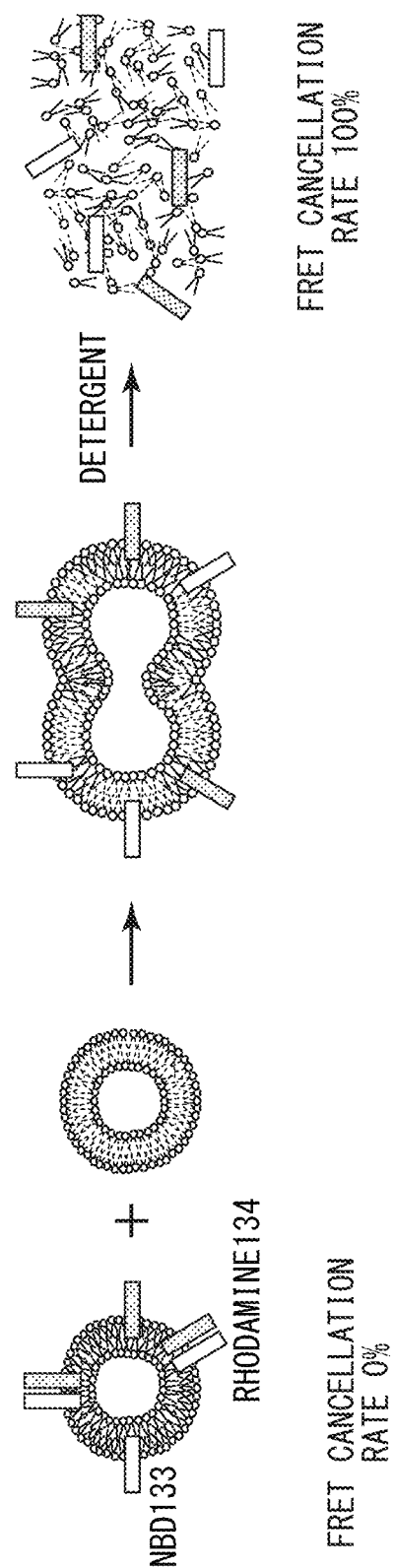
FIG. 31 is a schematic view for illustrating a vesicle fusion experiment in Example 5.

FIG. 31 is a schematic view illustrating a vesicle fusion experiment according to the present embodiment.

In the lipid membrane structure (corresponding to the dichroic fluorescence-labeled liposome) modified with NBD and rhodamine, NBD and rhodamine are adjacent to each other. Therefore, fluorescence is in a quenched state. The fluorescence intensity in the lipid membrane structure modified with NBD and rhodamine is defined as a FRET cancellation rate of 0%.

In a case where a surfactant was added to a fusant of the lipid membrane structure and a vesicle and hence the fusant burst (in a case where the fusant underwent complete disassociation), the FRET cancellation rate was defined as being 100%.

In a case where the lipid membrane structure (corresponding to the dichroic fluorescence-labeled liposome) is mixed with a vesicle (corresponding to the DOPS liposome), and membrane fusion occurs between the lipid membrane structure and the vesicle, because NBD and rhodamine become distant from each other, FRET is canceled, and an increase of fluorescence intensity is observed. By this method, the extent of membrane fusion can be evaluated based on a change of fluorescence intensity (FRET cancellation rate).

Figure 32:
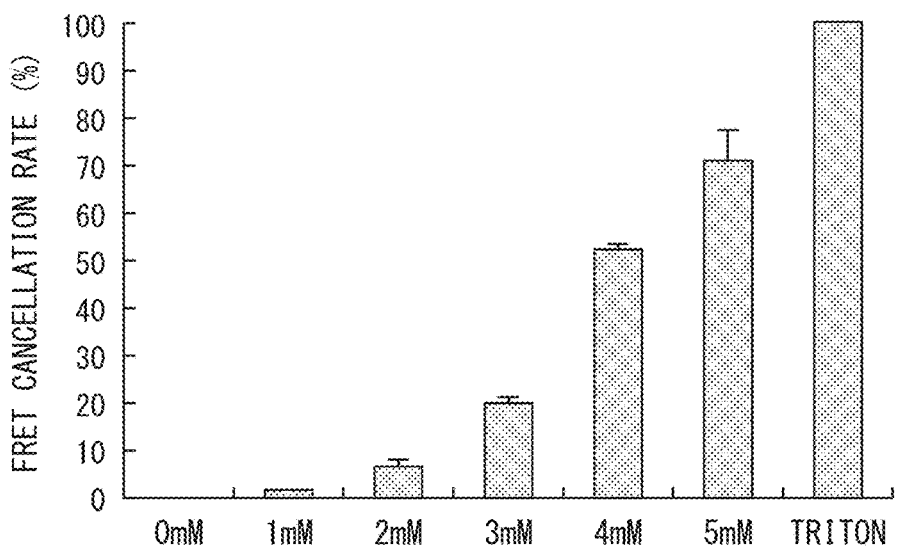
FIG. 32 is a graph showing the results of fluorescence detection in Example 5.

FIG. 32 shows a graph of the FRET cancellation rate (%) obtained in a case where the concentration of Ca added to a vesicle is changed within a range of 0 to 5 mM. FIG. 32 also shows the results obtained in a case where a fusant was burst (the fusant was underwent complete disassociation) by using a surfactant (TRITON®).

As shown in FIG. 32, the FRET cancellation rate increased (fluorescence intensity increased) when the Ca concentration was equal to or higher than 3 mM.

In the present embodiment, it was confirmed that by adding Ca as a membrane fusion-inducing additive the membrane fusion between the lipid membrane structure and a vesicle was induced.

Example 6

<Preparation of pH-Responsive Liposome and pH-Responsive Fluorescence-Labeled Liposome>

In a glass test tube, 1,2-Dioleoyl-sn-Glycero-3-Phosphoethanolamine (hereinafter, abbreviated to DOPE, manufactured by NOF CORPORATION) and Cholesteryl hemisuccinate (hereinafter, abbreviated to CHEMS) (manufactured by Avanti Polar Lipids, Inc.) were dissolved in chloroform such that a molar ratio thereof became 3:2, thereby preparing a 10 mg/mL DOPE•CHEMS chloroform solution. The DOPE•CHEMS chloroform solution was dried under reduced pressure by using a desiccator such that the organic solvent was removed, thereby preparing a lipid thin membrane. The lipid thin membrane was mixed with 1 mL of a MES buffer, and the mixture was treated with ultrasonic waves for approximately 1 minute by using a bath-type sonicator, thereby preparing pH-responsive liposomes.

Furthermore, in a glass test tube, DOPE, CHEMS, NBD-PE, and Rhodamine-PE were dissolved in chloroform such that a molar ratio thereof became 60:40:1:0.5, thereby preparing a 10 mg/mL DOPE•CHEMS•NBD-PE•Rhodamine-PE chloroform solution. The DOPE•CHEMS•NBD-PE•Rhodamine-PE chloroform solution was dried under reduced pressure by using a desiccator such that the organic solvent was removed, thereby preparing a lipid thin membrane. The lipid thin membrane was mixed with 1 mL of a MES buffer, and the mixture was treated with ultrasonic waves for approximately 1 minute by using a bath-type sonicator, thereby preparing pH-responsive fluorescence-labeled liposomes.

In order to adjust the size of the pH-responsive liposomes and the pH-responsive fluorescence-labeled liposomes, the liposomes were passed through a filter of Nuclepore polymembrane carbonate (manufactured by Whatman PLC) having a pore size of 100 nm, thereby preparing uniform pH-responsive liposomes and pH-responsive fluorescence-labeled liposomes.

<Testing pH-Responsive Fusion>

A solution, which was obtained by mixing 2 µL of a mixed liquid of the pH-responsive liposomes (10 mg/mL) and the pH-responsive fluorescence-labeled liposomes (10 mg/mL) with 198 µL of MES buffers having different pH (pH 4.5, pH 5.0, pH 5.5, pH 6.0, and pH 7.4), was incubated for 1 hour at 37° C.

Figure 33:
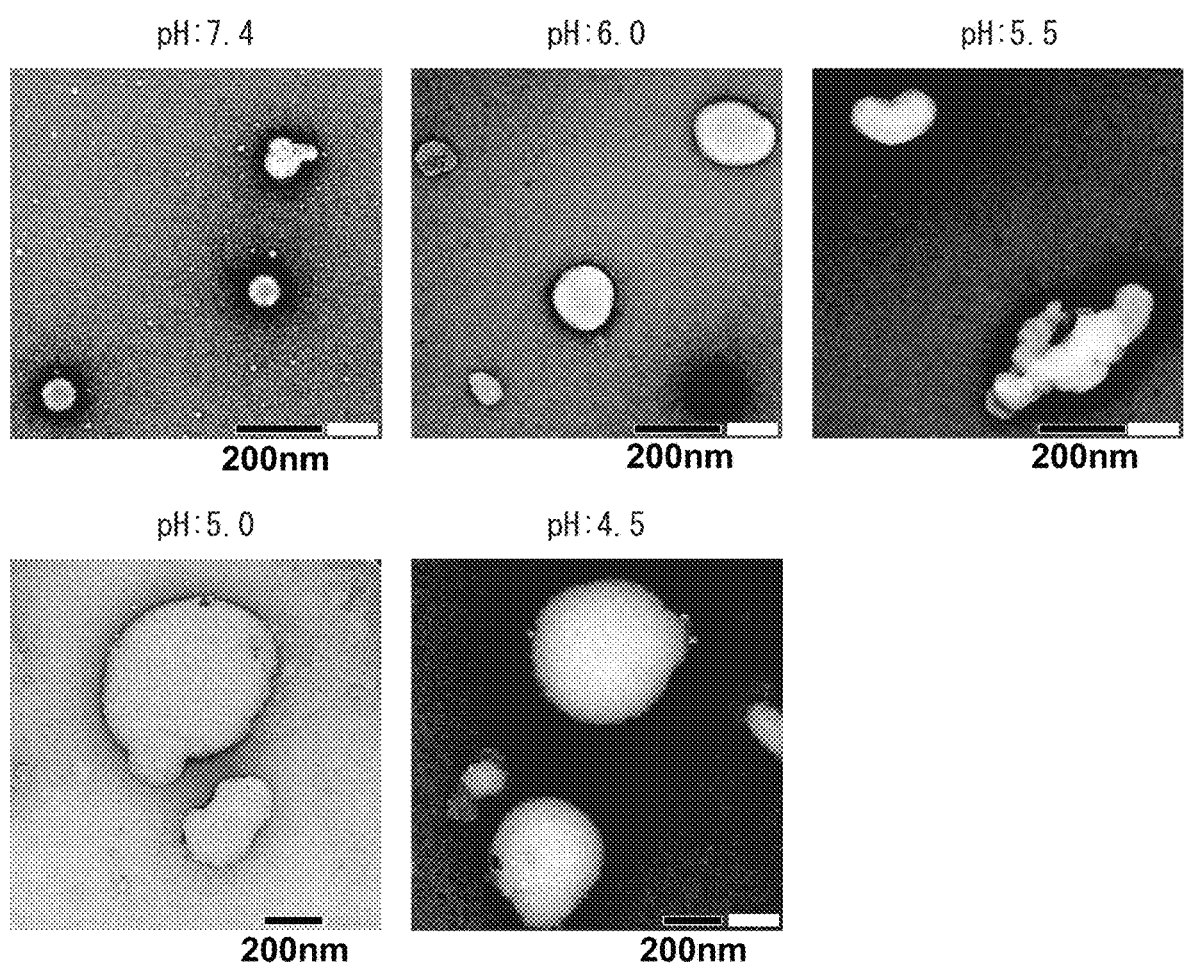
FIG. 33 shows TEM images in Example 6.

FIG. 33 shows TEM images obtained in a case where the pH in membrane fusions of the pH-responsive liposomes and the pH-responsive fluorescence-labeled liposomes was varied (pH 4.5, pH 5.0, pH 5.5, pH 6.0, and pH 7.4).

As shown in FIG. 33, by using TEM, it was possible to confirm that the particle size of fusants of the pH-responsive liposomes and the pH-responsive fluorescence-labeled liposomes markedly increased when the pH was equal to or less than 5.5.

That is, it was confirmed that the membrane fusion was accelerated when the pH was equal to or less than 5.5.

Figure 34:
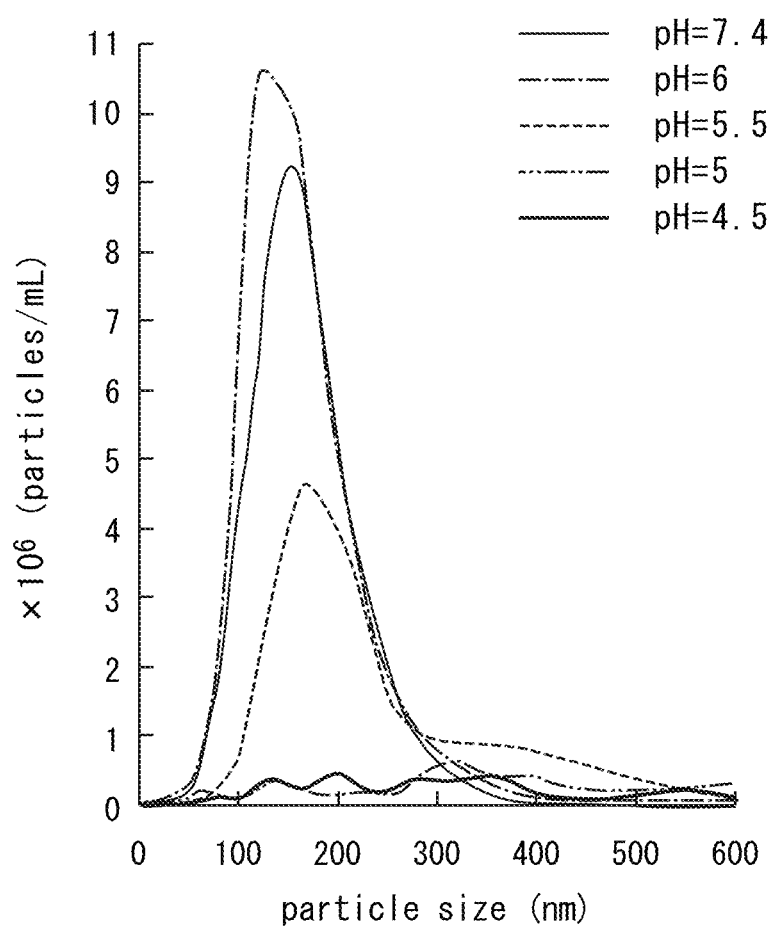
FIG. 34 shows the results of particle size distribution analysis in Example 6.

FIG. 34 shows the results of particle size distribution analysis on the fusants at a pH 4.5, a pH 5.0, a pH 5.5, a pH 6.0, and a pH 7.4. For the particle size distribution analysis, a nanoparticle size analyzer (NanoSight NS-500, Quantum Design Japan) was used.

As shown in FIG. 34, it was confirmed that when the pH was equal to or less than 5.5, an average particle size of the fusants increased, and the number of particles resulting from the membrane fusion decreased.

Figure 35:
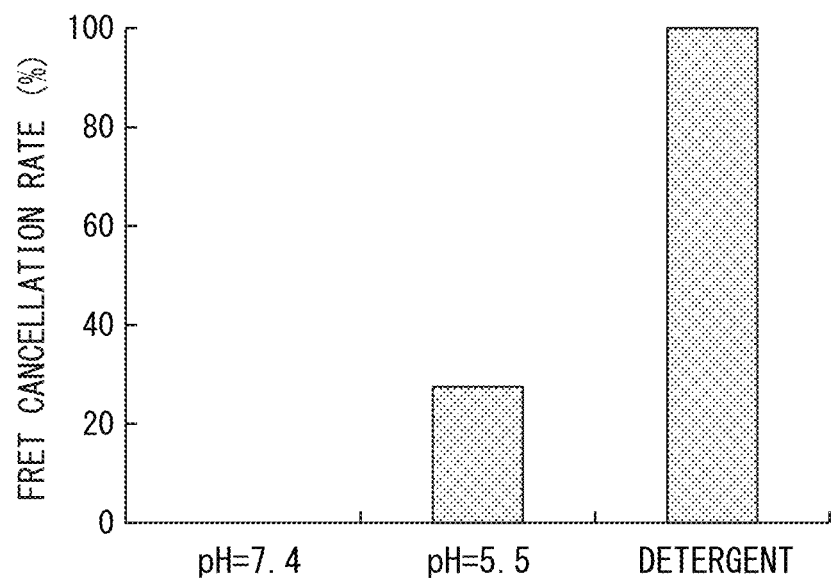
FIG. 35 is a graph showing the results of fluorescence detection in Example 6.

FIG. 35 shows a graph of a FRET cancellation rate (%) obtained when the pH of the mixed liquid of the pH-responsive liposomes and the pH-responsive fluorescence-labeled liposomes was 7.4 and 5.5. In the present embodiment, in a case where the pH was 7.4, the FRET cancellation rate was defined as being 0%.

FIG. 35 also shows the results obtained in a case where the fusant was burst by using a surfactant (TRITON®) (a case where a fusant underwent complete disassociation, and the FRET cancellation rate was 100%).

As shown in FIG. 35, the FRET cancellation rate increased (fluorescence intensity increased) when the pH was equal to or less than 5.5.

By the present example, it was confirmed that, by modifying the lipid membrane structure with a pH-responsive lipid, the membrane fusion between the lipid membrane structure and a vesicle was induced.

Example 7

Fluorescent liposomes were detected using biotin-modified liposomes, fluorescence-labeled liposomes, and a 96-well plate.

One hundred (100) µL of biotin-modified liposomes (lipid concentration: 62.5 µg/mL) were added to a Streptavidin Coated Plates (HBC) Black 96-well with SUPERBLOCK® Blocking Buffer, and the resultant was incubated for 5 hours at 25° C., thereby preparing an artificial-vesicle-immobilization substrate in which an artificial vesicle (lipid membrane structure) was immobilized on a substrate. After the substrate was washed 3 times with 300 µL of PBS, a solution (DOPS/rhodamine) obtained by mixing 10 µL. of the fluorescence-labeled liposomes (10 mg/mL) with 190 µL of a MES buffer and a solution (DOPS/rhodamine+Ca 5 mM) obtained by mixing 10 µL of the fluorescence-labeled liposomes (10 mg/mL) with 190 µL of a MES buffer-CaCl$_2$ solution (final concentration: 5 mM) were incubated for 1 hour at 37° C. The resultant was washed 3 times with 300 µL of PBS, and then the fluorescence intensity of rhodamine was measured using a plate reader.

Figure 36:
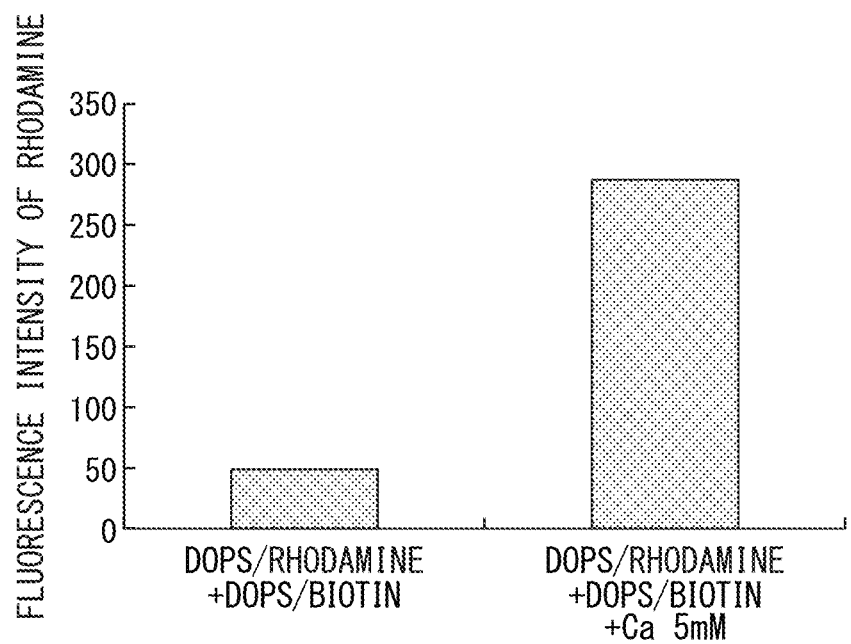
FIG. 36 is a graph showing the results of fluorescence detection in Example 7.

FIG. 36 shows a case (DOPS/rhodamine+DOPS/biotin) where fluorescent molecule-containing liposomes (DOPS/rhodamine) were added to the artificial-vesicle-immobilization substrate in which biotin-modified liposomes (DOPS/biotin) were immobilized and a case (DOPS/rhodamine+DOPS/biotin+Ca 5 mM) where fluorescent molecule-containing liposomes (DOPS/rhodamine) and Ca were added to a substrate in which a biotin-modified liposome (DOPS/biotin) was immobilized. In FIG. 36, the ordinate shows the fluorescence intensity resulting from rhodamine.

As shown in FIG. 36, it was confirmed that, even in a case where the artificial-vesicle-immobilization substrate, in which a biotin-modified liposome was immobilized, was used, by adding fluorescent molecule-containing liposomes (DOPS/rhodamine) and Ca, the membrane fusion between liposomes was accelerated.

By the present example, it was confirmed that the use of a lipid-membrane-structure-immobilization carrier (artificial-vesicle-immobilization substrate) enables vesicles to be fused with each other on a carrier (enables a lipid membrane structure and a vesicle to be fused with each other).

Furthermore, by the present example, it was confirmed that the use of a lipid-membrane-structure-immobilization carrier makes it possible to separate, move, and detect a vesicle.

Example 8

<Preparation of Magnetic Substance-Containing Liposome>

In a glass test tube, DOPS (manufactured by NOF CORPORATION) was dissolved in chloroform, thereby preparing a 10 mg/mL DOPS chloroform solution. A mixed solution of the DOPS chloroform solution and 10 mM glucose (manufactured by Wako Pure Chemical Industries, Ltd.) in methanol was dried under reduced pressure by using a desiccator such that the organic solvent was removed, thereby preparing a lipid thin membrane. The lipid thin membrane was mixed with 200 nm magnetic particles (manufactured by Tamagawa seiki Co., Ltd.) and 1 mL of a MES buffer, and the mixture was stirred for approximately 1 minute by using a Vortex mixer, thereby preparing magnetic substance-containing liposomes.

In order to adjust the size of the magnetic substance-containing liposomes, the liposomes were passed through a syringe filter of polymembrane carbonate (manufactured by Millipore Corporation) having a pore size of 3 μm, thereby preparing uniform magnetic substance-containing liposomes.

In order to remove magnetic particles not being contained in the liposomes and liposomes not containing the magnetic substance, centrifugation (20,000 G, 10 minutes), collection by a magnetic stand, and washing were repeated 3 times, thereby preparing magnetic substance-containing liposomes.

<Fluorescence-Labeled GUV Liposome>

In a glass test tube, DOPS (manufactured by NOF CORPORATION) and Rhodamine-PE (manufactured by Avanti Polar Lipids, Inc.) were dissolved in chloroform such that a molar ratio thereof became 100:1, thereby preparing a 10 mg/mL DOPS•Rhodamine-PE chloroform solution. A mixed solution of the DOPS•Rhodamine-PE chloroform solution and 10 mM glucose (manufactured by Wako Pure Chemical Industries, Ltd.) in methanol was dried under reduced pressure by using a desiccator such that the organic solvent was removed, thereby preparing a lipid thin membrane. The lipid thin membrane was mixed with 1 mL of a MES buffer, and the mixture was stirred for approximately 1 minute by using a Vortex mixer, thereby preparing fluorescence-labeled liposomes.

In order to adjust the size of the fluorescence-labeled GUV liposomes, the liposomes were passed through a syringe filter of polymembrane carbonate (manufactured by Millipore Corporation) having a pore size of 3 μm, thereby preparing uniform fluorescence-labeled liposomes.

<Testing Fusion•Magnetic Separation>

A solution, which was obtained by mixing 5 μL of the magnetic substance-containing liposomes and the fluorescence-labeled GUV liposomes, and 95 μL of a MES buffer-CaCl$_2$ solution (final concentration: 5 mM) together, was incubated for 1 hour at 37° C. Collection by a magnetic stand and washing were performed 3 times, and then the fluorescence intensity of rhodamine was measured using a plate reader.

Figure 37:
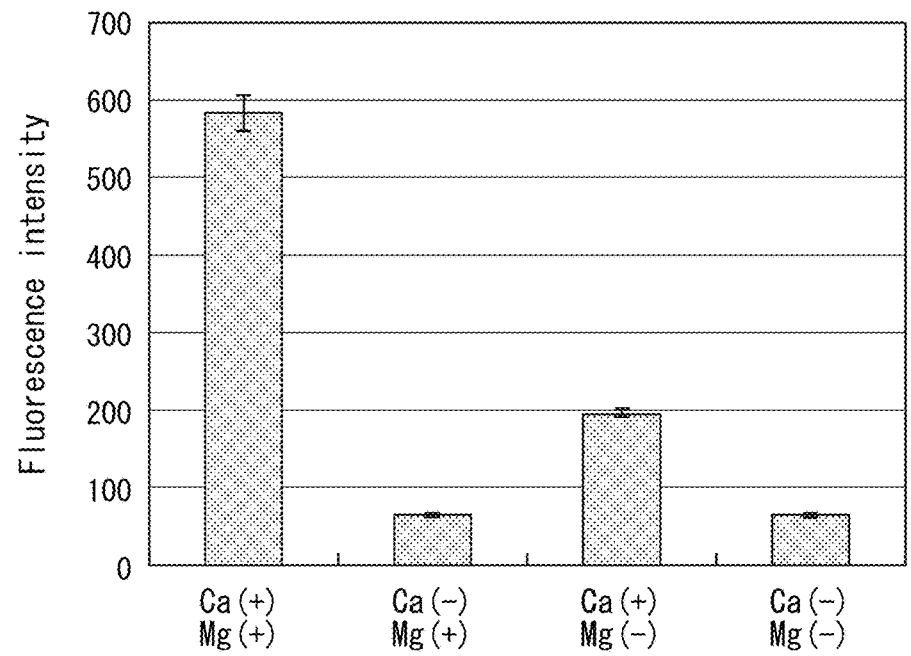
FIG. 37 is a graph showing the results of fluorescence detection in Example 8.

FIG. 37 shows the results obtained when the fusant was magnetically separated. In FIG. 37, Ca (+) represents a case where the mixed solution of the magnetic substance-containing liposomes and the fluorescent liposomes contains Ca. In a case where the mixed solution of the magnetic substance-containing liposomes and the fluorescent liposomes contains Ca, the formation of a fusant is accelerated.

In FIG. 37, Ca (−) represents a case where Ca was not added to the mixed solution.

In FIG. 37, Mg (+) represents a case where the fusant was separated using a magnetic force-generating device (magnetic stand).

In FIG. 37, Mg (−) represents a case where magnetic separation was not performed.

The ordinate in FIG. 37 shows the fluorescence intensity.

As shown in FIG. 37, in a case where Ca was added to form a fusant and magnetic separation was performed (a case of Ca (+) and Mg (+)), the fluorescence intensity more markedly increased than in a case where Ca was not added and magnetic separation was not performed.

That is, the magnetic substance-containing fusant generated by the membrane fusion caused by the addition of Ca was magnetically separated and fluorescently detected.

By the present example, it was confirmed that the fusant can be separated and moved to and detected in an arbitrary place (for example, a detection site or the like) by using magnetic force-generating means.

Example 9

<Preparation of Membrane Chamber>

A flow cell, in which micropores having a diameter of 5 μm and a depth of 3 μm were formed on glass and which is obtained by combining a CYTOP (manufactured by ASAHI GLASS CO., LTD.) chamber with glass sheet for feeding, was fed twice with 20 μL of a mixed solution of a MgCl$_2$ solution (final concentration: 1 mM), a MOPS buffer (10 mM, pH: 7.9), 1% glycerol, and Alexa 488 (final concentration: 2 μM), and then fed with 20 μL of a lipid solution which was obtained by dissolving 4 mg of 1,2-Dioleoyl-sn-glycero-3-phosphocholine (hereinafter, abbreviated to DOPC, manufactured by NOF CORPORATION) and 1,2-Dioleoyl-sn-glycero-3-phosphoglycerol (hereinafter, abbreviated to DOPG, manufactured by NOF CORPORATION) in 1 mL of hexadecane. The flow cell was then fed twice with 20 μL of a mixed solution of a MgCl$_2$ solution (final concentration: 1 mM), a MOPS buffer (10 mM, pH: 7.9), and 1% glycerol, thereby preparing a fluorescence-containing membrane chamber.

<Preparation of Fluorescence-Labeled Liposome>

In a glass test tube, DOPC, DOPE (manufactured by NOF CORPORATION), and Rhodamine-PE (manufactured by Avanti Polar Lipids, Inc.) were dissolved in chloroform such that a molar ratio thereof became 100:100:1, thereby preparing a 15 mg/mL DOPC•DOPE•Rhodamine-PE chloroform solution. A mixed solution of the DOPC•DOPE•Rhodamine-PE chloroform solution and 10 mM glucose (manufactured by Wako Pure Chemical Industries, Ltd.) in methanol was dried under reduced pressure by using a desiccator such that the organic solvent was removed, thereby preparing a lipid thin membrane. The lipid thin membrane was mixed with 1 mL of a mixed solution of a $MgCl_2$ solution (final concentration: 1 mM), a MOPS buffer (10 mM, pH: 7.9), and 1% glycerol, and the mixture was stirred for approximately 1 minute by using a Vortex mixer, thereby preparing fluorescence-labeled liposomes.

In order to adjust the size of the fluorescence-labeled liposomes, the liposomes were passed through a syringe filter of polymembrane carbonate (manufactured by Millipore Corporation) having a pore size of 3 μm, thereby preparing uniform fluorescence-labeled liposomes.

In order to remove fluorescent substances not being contained in the liposomes, collection by centrifugation (20,000 G, 10 minutes) and washing were repeated 3 times, thereby preparing fluorescence-labeled liposomes.

<Membrane Chamber•Liposome Fusion Test>

The aforementioned fluorescence-containing membrane chamber was fed with the fluorescence-labeled liposomes and 20 μL of a $CaCl_2$ solution (final concentration: 1 mM) and fed with 80 μL of a mixed solution of a $MgCl_2$ solution (final concentration: 1 mM), a MOPS buffer (10 mM, pH: 7.9), and 1% glycerol. Then, by using a fluorescence microscope BX50 (manufactured by OLYMPUS CORPORATION), fluorescence of Alexa 488 and rhodamine was observed.

Figure 38:
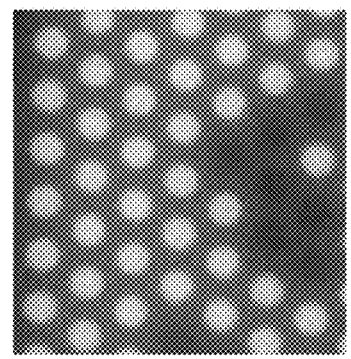
FIG. 38 is a fluorescence image in Example 9.

FIG. 38 shows a fluorescence image of the inside of the membrane of the membrane chamber in which a lipid membrane was formed in recess portions (wells) of a substrate. As shown in FIG. 38, it was confirmed that the membrane chamber was formed on the substrate.

Figure 39:
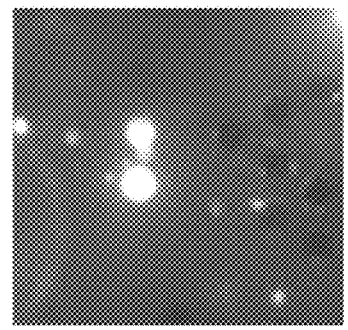
FIG. 39 is a fluorescence image in Example 9.

FIG. 39 shows a fluorescence image of the fluorescence-labeled liposomes. It was understood that, in a case where the fluorescence-labeled liposomes exist, a fluorescence image as shown in FIG. 39 is obtained.

Figure 40:
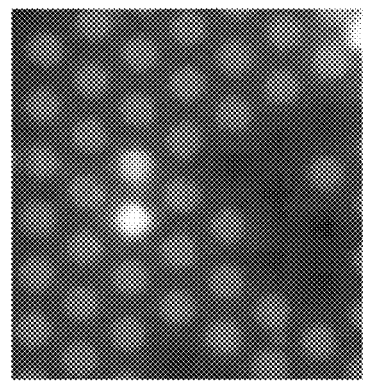
FIG. 40 is a fluorescence image in Example 9.

FIG. 40 shows a fluorescence image of a membrane chamber obtained in a case where an experiment of a membrane chamber•liposome fusion test was performed.

From the result shown in FIG. 40, an increase of fluorescence resulting from the fusion between a lipid membrane formed on the membrane chamber and the fluorescence-labeled liposome was detected.

By the present example, it was confirmed that it is possible to cause a reaction between a reaction reagent and a constituent of a vesicle by fusing an artificial vesicle with a lipid membrane structure on a substrate, and to detect the reaction or a reaction product generated by the reaction.

Example 10

<Testing Detection Reaction in Fusant>

In the present example, detection of a reaction in a fusant as shown in FIG. 15 was investigated.

<Preparation of Rhodamine-Containing Liposome and NBD-Containing Liposome>

In a glass test tube, DOPS (manufactured by NOF CORPORATION) was dissolved in chloroform, thereby preparing a 10 mg/mL DOPS chloroform solution. A mixed solution of the DOPS chloroform solution and 10 mM glucose (manufactured by Wako Pure Chemical Industries, Ltd.) in methanol was dried under reduced pressure by using a desiccator such that the organic solvent was removed, thereby preparing a lipid thin membrane. The lipid thin membrane was mixed with Rhodamine-PE (manufactured by Avanti Polar Lipids, Inc.) and 1 mL of a MES buffer, and the mixture was stirred for approximately 1 minute by using a Vortex mixer, thereby preparing fluorescence-labeled liposomes.

In order to adjust the size of the Rhodamine-containing liposomes, the fluorescence-labeled liposomes were passed through a syringe filter of polymembrane carbonate (manufactured by Millipore Corporation) having a pore size of 3 μm, thereby preparing uniform Rhodamine-labeled liposomes.

In order to remove the fluorescent substance not being containing in the liposomes, collection by centrifugation (20,000 G, 10 minutes) and washing were repeated 3 times, thereby preparing Rhodamine-containing liposomes.

In a glass test tube, DOPS (manufactured by NOF CORPORATION) was dissolved in chloroform, thereby preparing a 10 mg/mL DOPS chloroform solution. A mixed solution of the DOPS chloroform solution and 10 mM glucose (manufactured by Wako Pure Chemical Industries, Ltd.) in methanol was dried under reduced pressure by using a desiccator such that the organic solvent was removed, thereby preparing a lipid thin membrane. The lipid thin membrane was mixed with 1 mL of NBD-PE (manufactured by Avanti Polar Lipids, Inc.) and a MES buffer, and the mixture was stirred for approximately 1 minute by using a Vortex mixer, thereby preparing fluorescence-labeled liposomes.

In order to adjust the size of the NBD-containing liposomes, the liposomes were passed through a syringe filter of polymembrane carbonate (manufactured by Millipore Corporation) having a pore size of 3 μm, thereby preparing uniform NBD-labeled liposomes.

In order to remove the fluorescent substance not being contained in the liposomes, collection by centrifugation (20,000 G, 10 minutes) and washing were repeated 3 times, thereby preparing NBD-containing liposomes.

<Testing FRET in Fusant>

A solution, which was obtained by mixing 5 μL of a mixed liquid of the Rhodamine-containing liposomes and the NBD-containing liposomes with 95 μL of a MES buffer-$CaCl_2$ solution (final concentration: 5 mM), was incubated for 1 hour at 37° C., and then fluorescence intensity of FRET (excitation wavelength: 463 nm, fluorescence wavelength: 580 nm) was measured using a plate reader.

Figure 41:
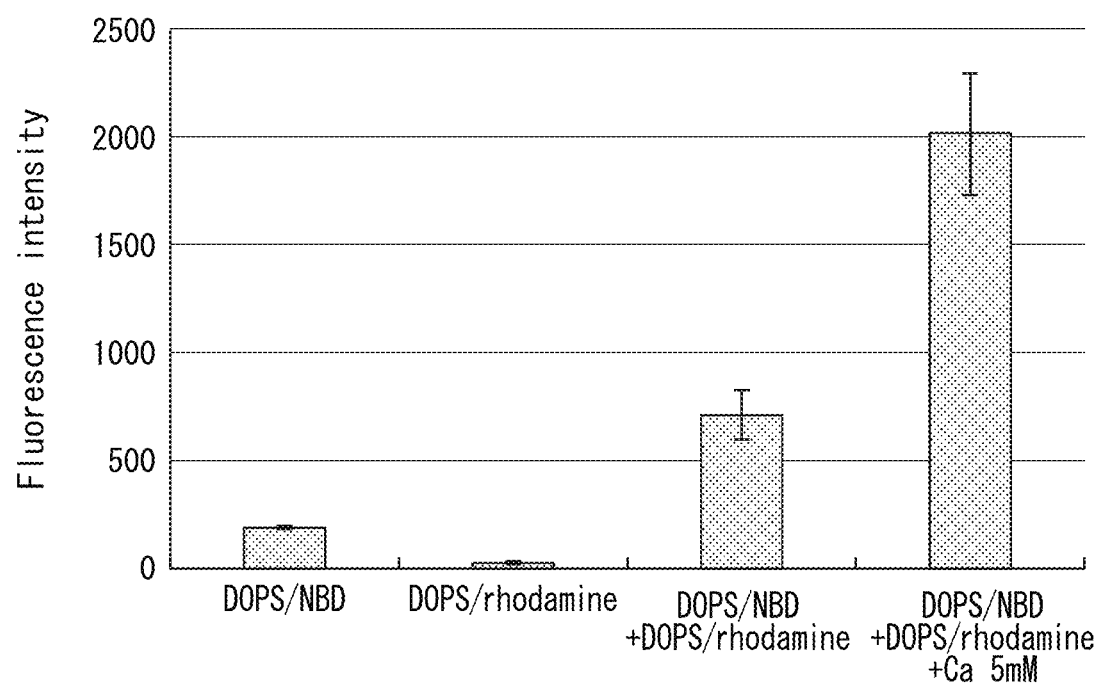
FIG. 41 is a graph showing the results of fluorescence detection in Example 10.

FIG. 41 shows the results obtained from the Rhodamine-containing liposomes (DOPS/rhodamine), the NBD-containing liposomes (DOPS/NBD), the "Rhodamine-containing liposomes+NBD-containing liposomes (DOPS/NBD+DOPS/rhodamine)", and a sample (DOPS/NBD+DOPS/rhodamine+Ca 5 mM) obtained by adding 5 mM Ca to the "Rhodamine-containing liposomes+NBD-containing liposomes".

Herein, the ordinate shows the fluorescence intensity of FRET.

As shown in FIG. 41, in a case where Ca was added, the fluorescence intensity in the fusant more markedly increased than in a case where Ca was not added.

That is, in a fusant generated by the membrane fusion caused by the addition of Ca, a FRET reaction occurs between Rhodamine and NBD, and an increase of fluorescence intensity was detected.

By the present example, it was confirmed that a reaction in a fusant can be detected using membrane fusion.

Example 11

<Testing Liposome-Exosome Fusion and Particle Size Distribution>

<Preparation of DOPC Liposome and DOPS Liposome>

In a glass test tube, DOPC or DOPS (manufactured by NOF CORPORATION) was dissolved in chloroform, thereby preparing a 10 mg/mL DOPC chloroform solution or a 10 mg/mL DOPS chloroform solution. A mixed solution of the DOPC chloroform solution or the DOPS chloroform solution and 10 mM glucose (manufactured by Wako Pure Chemical Industries, Ltd.) in methanol was dried under reduced pressure by using a desiccator such that the organic solvent was removed, thereby preparing a lipid thin membrane. The lipid thin membrane was mixed with 1 mL of a MES buffer, and the mixture was stirred for approximately 1 minute by using a Vortex mixer, thereby preparing DOPC liposomes (GUV (DOPC)) or DOPS liposomes (GUV (DOPS)).

In order to adjust the size of the DOPC liposomes or the DOPS liposomes, the liposomes were passed through a syringe filter of polymembrane carbonate (manufactured by Millipore Corporation) having a pore size of 3 μm, thereby preparing uniform DOPC liposomes or DOPS liposomes.

<Testing Liposome-Exosome Fusion>

A solution, which was obtained by mixing the DOPC liposomes or the DOPS liposomes, 4.5 μL of exosomes prepared from human serum (manufactured by Lonza), and 95.5 μL of a MES buffer together, was incubated for 1 hour at 37° C.

Figure 42:
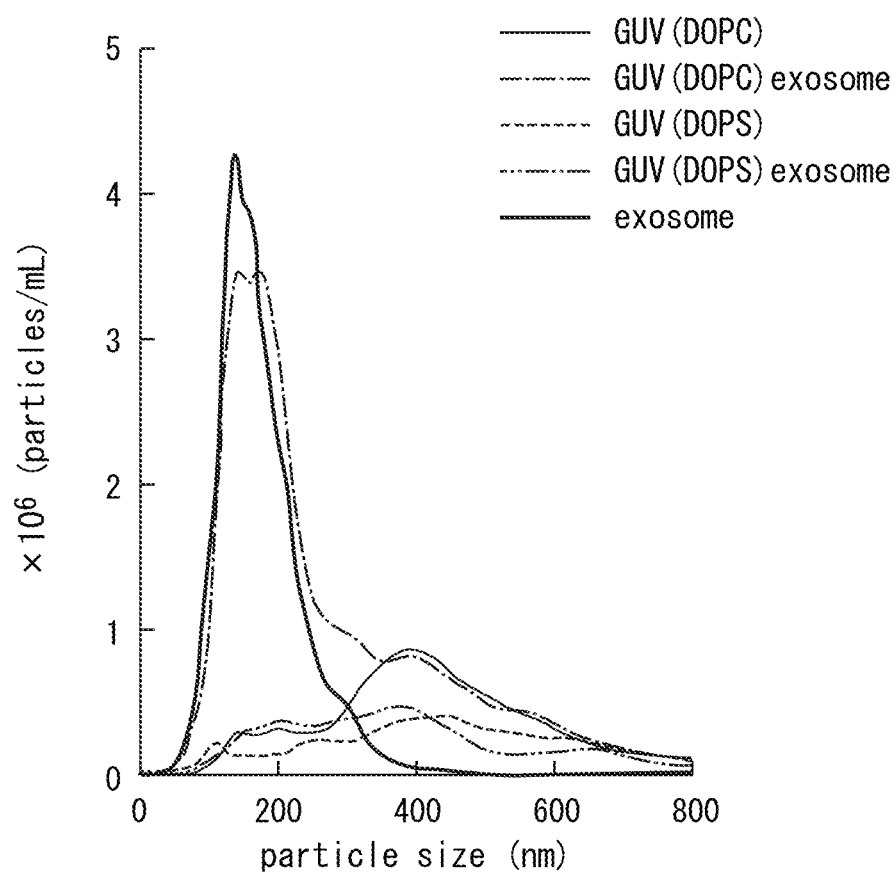
FIG. 42 is a graph showing the results of fluorescence detection in Example 11.

FIG. 42 shows the results of particle size distribution analysis performed on the DOPC liposomes (GUV (DOPC)), the DOPS liposomes (GUV (DOPS)), the exosomes, the DOPC liposomes+exosomes (GUV (DOPC) exosome), and the DOPS liposomes+exosomes (GUV (DOPS) exosome). For the particle size distribution analysis, a nanoparticle size analyzer (NanoSight NS-500, Quantum Design Japan) was used.

As shown in FIG. 42, it was confirmed that in the DOPS liposomes+exosomes, an average particle size of the exosomes increased, and the number of particles decreased.

By the present example, an interaction between the DOPS liposomes and the exosomes was confirmed.

Hitherto, embodiments of the present invention have been specifically described together with examples with reference to drawings, but the specific constitution of the present invention is not limited to the embodiments. Within a scope that does not depart from the present invention, design change and the like are also included in the present invention. Furthermore, the constituents described in each of the above embodiments can be appropriately combined.

INDUSTRIAL APPLICABILITY

By using the lipid membrane structure or the lipid-membrane-structure-immobilization carrier according to the present invention, it is possible to efficiently separate, detect, and move extracellular vesicles in a simple manner. Furthermore, according to the method of fusing vesicles, the method of separating a vesicle, the method of detecting a vesicle, and the method of moving a vesicle of the present invention, it is possible to efficiently fuse, separate, detect, and move extracellular vesicles in a simple manner. It is considered that the lipid membrane structure, the lipid-membrane-structure-immobilization carrier, and the aforementioned methods will be widespread as substitutes for a method of preparing vesicle sample, a collecting device, a detection method, and the like that have been conventionally used.

What is claimed is:

1. A method of separating a vesicle from a sample, comprising:
providing a substrate having a plurality of recess portions respectively recessed on a surface of the substrate, the substrate having a plurality of lipid membrane structures immobilized on the substrate, the plurality of lipid membrane structures containing membrane-fusogenic lipids that close, respectively, openings of the plurality of recess portions on the substrate, wherein the membrane-fusogenic lipids are capable of being fused with a vesicle having a lipid bilayer membrane;
bringing the substrate into contact with a sample having the vesicle such that a membrane fusion occurs between the lipid bilayer membrane of the vesicle and a lipid membrane structure among the plurality of lipid membrane structures to form a fused membrane; and
separating the vesicle from the sample and confining a constituent of the vesicle between:
the fused membrane formed from the lipid bilayer membrane of the vesicle and the lipid membrane structure among the plurality of lipid membrane structures, and
a recess portion corresponding to the lipid membrane structure, among the plurality of recess portions.

2. The method according to claim 1,
wherein the recess portion closed by the lipid membrane structure contains a reaction reagent, and
when the constituent is reactable with the reaction reagent, the reaction reagent is to react with the constituent of the vesicle after the membrane fusion occurs between the lipid bilayer membrane of the vesicle and the lipid membrane structure, to generate a reaction or a detectable reaction product.

3. The method according to claim 2,
wherein the reaction reagent is a reagent that generates a signal in the reaction.

4. The method according to claim 3,
wherein the signal is fluorescent signal.

5. The method according to claim 2,
wherein the constituent is a membrane protein.

6. A method of detecting a vesicle, comprising:
providing a substrate having a plurality of recess portions respectively recessed on a surface of the substrate, the substrate having a plurality of lipid membrane structures immobilized on the substrate, the plurality of lipid membrane structures containing membrane-fusogenic lipids that close, respectively, openings of the plurality of recess portions on the substrate, wherein the membrane-fusogenic lipids are capable of being fused with a vesicle having a lipid bilayer membrane;
bringing the substrate into contact with a sample having the vesicle such that a membrane fusion occurs between the lipid bilayer membrane of the vesicle and a lipid membrane structure among the plurality of lipid membrane structures to form a fused membrane;
separating the vesicle from the sample and confining a constituent of the vesicle between: the fused membrane formed from the lipid bilayer membrane of the vesicle and the lipid membrane structure among the plurality of lipid membrane structures, and a recess portion corresponding to the lipid membrane structure, among the plurality of recess portions; and detecting a fusant generated by the membrane fusion between the lipid bilayer membrane of the vesicle and the lipid membrane structure.

7. The method of claim 6,
wherein the lipid membrane structure contains a reaction reagent to react with the constituent,
the lipid membrane structure is brought into contact with the vesicle such that the membrane fusion occurs between the lipid bilayer membrane of the vesicle and the lipid membrane structure,
a reaction is caused between the reaction reagent and the constituent of the vesicle by the membrane fusion between the lipid bilayer membrane of the vesicle and the lipid membrane structure, and
the reaction or a reaction product generated by the reaction is detected.

\* \* \* \* \*